(12) United States Patent
Gordon et al.

(10) Patent No.: US 9,579,124 B2
(45) Date of Patent: Feb. 28, 2017

(54) EXPANDABLE ARTICULATING INTERVERTEBRAL IMPLANT WITH LIMITED ARTICULATION

(75) Inventors: Charles R. Gordon, Tyler, TX (US); Corey T. Harbold, Tyler, TX (US); Heather S. Hanson, San Antonio, TX (US)

(73) Assignee: Flexuspine, Inc., Tyler, TX (US)

( * ) Notice: Subject to any disclaimer, the term of this patent is extended or adjusted under 35 U.S.C. 154(b) by 375 days.

(21) Appl. No.: 13/437,604

(22) Filed: Apr. 2, 2012

(65) Prior Publication Data

US 2012/0310349 A1    Dec. 6, 2012

Related U.S. Application Data

(63) Continuation of application No. 11/134,079, filed on May 20, 2005, now Pat. No. 8,147,550, which is a
(Continued)

(51) Int. Cl.
*A61F 2/44* (2006.01)
*A61B 17/70* (2006.01)
(Continued)

(52) U.S. Cl.
CPC ........ *A61B 17/7023* (2013.01); *A61B 17/701* (2013.01); *A61B 17/7005* (2013.01); *A61B 17/7007* (2013.01); *A61B 17/7008* (2013.01); *A61B 17/7032* (2013.01); *A61F 2/4405* (2013.01); *A61F 2/4425* (2013.01); *A61F 2/4455* (2013.01); *A61F 2/4611* (2013.01); *A61B 17/7037* (2013.01); *A61B 17/7064* (2013.01); *A61B 17/80* (2013.01);
(Continued)

(58) Field of Classification Search
CPC ........ A61F 2/4425; A61F 2/44; A61F 2/4455; A61F 2002/4475; A61F 2002/448; A61F 2002/30556; A61F 2002/30579
USPC ............................. 623/17.11–17.15
See application file for complete search history.

(56) References Cited

U.S. PATENT DOCUMENTS 3,848,601 A    11/1974   Ma et al.
3,867,728 A    2/1975    Substad et al.
(Continued)

FOREIGN PATENT DOCUMENTS

EP    1090595    11/2001
FR    2716616    9/1995
(Continued)

OTHER PUBLICATIONS

U. S. P.T. O. Final Office Action for U.S. Appl. No. 11/134,055, mailed Apr. 18, 2013.
(Continued)

*Primary Examiner* — Christopher D Prone
(74) *Attorney, Agent, or Firm* — Pandiscio & Pandiscio

(57) ABSTRACT

An artificial functional spinal unit including an expandable intervertebral implant that can be inserted via a posterior surgical approach and used with one or more facet replacement devices to provide an anatomically correct range of motion is described. Lordotic and non-lordotic expandable, articulating implants and cages are described, along with embodiments of facet replacement devices and instruments for insertion. Methods of insertion are also described.

67 Claims, 45 Drawing Sheets

Related U.S. Application Data continuation of application No. 11/050,632, filed on Feb. 5, 2005, now Pat. No. 7,753,958, which is a continuation-in-part of application No. PCT/US2004/025090, filed on Aug. 4, 2004, which is a continuation-in-part of application No. 10/777,411, filed on Feb. 12, 2004, now Pat. No. 7,909,869, which is a continuation-in-part of application No. 10/660,155, filed on Sep. 11, 2003, now Pat. No. 7,316,714, which is a continuation-in-part of application No. 10/634,950, filed on Aug. 5, 2003, now Pat. No. 7,204,853.

(51) Int. Cl.
*A61F 2/46* (2006.01)
*A61B 17/80* (2006.01)
*A61B 17/86* (2006.01)
*A61F 2/30* (2006.01)
*A61F 2/28* (2006.01)

(52) U.S. Cl.
CPC ........... *A61B 17/86* (2013.01); *A61F 2/30767* (2013.01); *A61F 2002/2835* (2013.01); *A61F 2002/305* (2013.01); *A61F 2002/3023* (2013.01); *A61F 2002/3038* (2013.01); *A61F 2002/3052* (2013.01); *A61F 2002/3055* (2013.01); *A61F 2002/30092* (2013.01); *A61F 2002/30131* (2013.01); *A61F 2002/30133* (2013.01); *A61F 2002/30225* (2013.01); *A61F 2002/30235* (2013.01); *A61F 2002/30365* (2013.01); *A61F 2002/30369* (2013.01); *A61F 2002/30383* (2013.01); *A61F 2002/30462* (2013.01); *A61F 2002/30471* (2013.01); *A61F 2002/30476* (2013.01); *A61F 2002/30492* (2013.01); *A61F 2002/30505* (2013.01); *A61F 2002/30507* (2013.01); *A61F 2002/30515* (2013.01); *A61F 2002/30538* (2013.01); *A61F 2002/30556* (2013.01); *A61F 2002/30563* (2013.01); *A61F 2002/30565* (2013.01); *A61F 2002/30578* (2013.01); *A61F 2002/30579* (2013.01); *A61F 2002/30601* (2013.01); *A61F 2002/30626* (2013.01); *A61F 2002/30649* (2013.01); *A61F 2002/30662* (2013.01); *A61F 2002/30772* (2013.01); *A61F 2002/30785* (2013.01); *A61F 2002/30794* (2013.01); *A61F 2002/30841* (2013.01); *A61F 2002/30904* (2013.01); *A61F 2002/443* (2013.01); *A61F 2002/4627* (2013.01); *A61F 2002/4628* (2013.01); *A61F 2002/4629* (2013.01); *A61F 2210/0014* (2013.01); *A61F 2220/0025* (2013.01); *A61F 2220/0033* (2013.01); *A61F 2220/0075* (2013.01); *A61F 2220/0091* (2013.01); *A61F 2230/0013* (2013.01); *A61F 2230/0015* (2013.01); *A61F 2230/0069* (2013.01); *A61F 2250/0006* (2013.01); *A61F 2250/0009* (2013.01); *A61F 2310/00023* (2013.01)

(56) References Cited

U.S. PATENT DOCUMENTS

| | | |
|---|---|---|
| 4,309,777 A | 1/1982 | Patil |
| 4,349,921 A | 9/1982 | Kuntz |
| 4,611,581 A | 9/1986 | Steffee |
| 4,657,550 A | 4/1987 | Daher |
| 4,696,290 A | 9/1987 | Steffee |
| 4,743,260 A | 5/1988 | Burton |
| 4,759,766 A | 7/1988 | Buettner-Janz et al. |
| 4,759,769 A | 7/1988 | Hedman et al. |
| 4,763,644 A | 8/1988 | Webb |
| 4,772,287 A | 9/1988 | Ray et al. |
| 4,854,311 A | 8/1989 | Steffee |
| 4,863,476 A | 9/1989 | Shepperd |
| 4,863,477 A | 9/1989 | Monson |
| 4,907,577 A | 3/1990 | Wu |
| 4,911,718 A | 3/1990 | Lee et al. |
| 4,932,975 A | 6/1990 | Main et al. |
| 4,946,378 A | 8/1990 | Hirayama et al. |
| 4,946,458 A | 8/1990 | Harms et al. |
| 5,042,982 A | 8/1991 | Harms et al. |
| 5,047,055 A | 9/1991 | Bao et al. |
| 5,059,194 A | 10/1991 | Michelson |
| 5,071,437 A | 12/1991 | Steffee |
| 5,092,867 A | 3/1992 | Harms et al. |
| 5,108,438 A | 4/1992 | Stone |
| 5,123,926 A | 6/1992 | Pisharodi |
| 5,171,278 A | 12/1992 | Pisharodi |
| 5,171,281 A | 12/1992 | Parsons et al. |
| 5,180,393 A | 1/1993 | Commarmond |
| 5,192,326 A | 3/1993 | Bao et al. |
| 5,196,013 A | 3/1993 | Harms et al. |
| 5,207,678 A | 5/1993 | Harms et al. |
| 5,217,497 A | 6/1993 | Mehdian |
| 5,246,458 A | 9/1993 | Graham |
| 5,258,031 A | 11/1993 | Salib et al. |
| 5,261,909 A | 11/1993 | Sutterlin et al. |
| 5,306,307 A | 4/1994 | Senter et al. |
| 5,306,309 A | 4/1994 | Wagner et al. |
| 5,314,477 A | 5/1994 | Marnay |
| 5,320,644 A | 6/1994 | Baumgartner |
| 5,336,223 A | 8/1994 | Rogers |
| 5,370,697 A | 12/1994 | Baumgartner |
| 5,375,823 A | 12/1994 | Navas |
| 5,397,364 A | 3/1995 | Kozak et al. |
| 5,401,269 A | 3/1995 | Buttner-Janz et al. |
| 5,403,315 A | 4/1995 | Ashman |
| 5,415,661 A | 5/1995 | Holmes |
| 5,423,816 A | 6/1995 | Lin |
| 5,425,773 A | 6/1995 | Boyd et al. |
| 5,443,467 A | 8/1995 | Biedermann et al. |
| 5,458,642 A | 10/1995 | Beer et al. |
| 5,458,643 A | 10/1995 | Oka et al. |
| 5,480,401 A | 1/1996 | Navas |
| 5,496,321 A | 3/1996 | Puno et al. |
| 5,498,263 A | 3/1996 | DiNello et al. |
| 5,507,816 A | 4/1996 | Bullivant |
| 5,514,132 A | 5/1996 | Csernatony et al. |
| 5,514,180 A | 5/1996 | Heggeness et al. |
| 5,522,899 A | 6/1996 | Michelson |
| 5,527,314 A | 6/1996 | Brumfield et al. |
| 5,534,028 A | 7/1996 | Bao et al. |
| 5,534,029 A | 7/1996 | Shima |
| 5,534,030 A | 7/1996 | Navarro et al. |
| 5,540,688 A | 7/1996 | Navas |
| 5,545,165 A | 8/1996 | Biedermann et al. |
| 5,556,431 A | 9/1996 | Buttner-Janz |
| 5,562,663 A | 10/1996 | Wisnewski et al. |
| 5,562,737 A | 10/1996 | Graf |
| 5,562,738 A | 10/1996 | Boyd et al. |
| 5,571,109 A | 11/1996 | Bertagnoli |
| 5,609,635 A | 3/1997 | Michelson |
| 5,624,442 A | 4/1997 | Mellinger et al. |
| 5,645,599 A | 7/1997 | Samani |
| 5,653,763 A | 8/1997 | Errico et al. |
| 5,665,122 A | 9/1997 | Kambin |
| 5,672,175 A | 9/1997 | Martin |
| 5,672,176 A | 9/1997 | Biedermann et al. |
| 5,674,294 A | 10/1997 | Bainville et al. |
| 5,674,296 A | 10/1997 | Bryan et al. |
| 5,676,701 A | 10/1997 | Yuan et al. |
| 5,676,702 A | 10/1997 | Ratron |
| 5,683,391 A | 11/1997 | Boyd |
| 5,683,464 A | 11/1997 | Wagner et al. |
| 5,683,465 A | 11/1997 | Shinn et al. |
| 5,702,450 A | 12/1997 | Bisserie |
| 5,725,527 A | 3/1998 | Biedermann et al. |
| 5,733,284 A | 3/1998 | Martin |

(56) References Cited

U.S. PATENT DOCUMENTS

| | | | |
|---|---|---|---|
| 5,741,253 A | 4/1998 | Michelson | |
| 5,755,797 A | 5/1998 | Baumgartner | |
| 5,772,661 A | 6/1998 | Michelson | |
| 5,776,199 A | 7/1998 | Michelson | |
| 5,782,832 A | 7/1998 | Larsen et al. | |
| 5,785,647 A | 7/1998 | Tompkins et al. | |
| 5,797,909 A | 8/1998 | Michelson | |
| 5,800,549 A | 9/1998 | Bao et al. | |
| 5,800,550 A | 9/1998 | Sertich | |
| 5,810,819 A | 9/1998 | Errico et al. | |
| 5,824,093 A | 10/1998 | Ray et al. | |
| 5,824,094 A | 10/1998 | Serhan et al. | |
| 5,827,328 A | 10/1998 | Buttermann | |
| 5,860,973 A | 1/1999 | Michelson | |
| 5,861,041 A | 1/1999 | Tienboon | |
| 5,863,293 A | 1/1999 | Richelsoph | |
| 5,865,846 A | 2/1999 | Bryan et al. | |
| 5,865,848 A | 2/1999 | Baker | |
| 5,888,220 A | 3/1999 | Felt et al. | |
| 5,888,226 A | 3/1999 | Rogozinski | |
| 5,893,889 A | 4/1999 | Harrington | |
| 5,895,427 A | 4/1999 | Kuslich et al. | |
| 5,895,428 A | 4/1999 | Berry | |
| 5,899,941 A | 5/1999 | Nishijima et al. | |
| 5,928,243 A | 7/1999 | Guyer | |
| 5,935,133 A | 8/1999 | Wagner et al. | |
| 5,938,663 A | 8/1999 | Petreto | |
| 5,951,555 A | 9/1999 | Rehak et al. | |
| 5,961,518 A | 10/1999 | Errico et al. | |
| 5,961,554 A | 10/1999 | Janson et al. | |
| 5,964,769 A | 10/1999 | Wagner et al. | |
| 5,976,186 A | 11/1999 | Bao et al. | |
| 5,980,522 A | 11/1999 | Koros et al. | |
| 5,984,967 A | 11/1999 | Zdeblick et al. | |
| 5,989,250 A | 11/1999 | Wagner et al. | |
| 5,989,290 A | 11/1999 | Biedermann et al. | |
| 5,997,539 A | 12/1999 | Errico et al. | |
| 6,001,130 A | 12/1999 | Bryan et al. | |
| 6,017,344 A | 1/2000 | Errico et al. | |
| 6,019,792 A | 2/2000 | Cauthen | |
| 6,022,376 A | 2/2000 | Assell et al. | |
| 6,030,389 A | 2/2000 | Wagner et al. | |
| 6,039,763 A | 3/2000 | Shelokov | |
| 6,045,552 A | 4/2000 | Zucherman et al. | |
| 6,045,579 A | 4/2000 | Hochshuler et al. | |
| 6,053,921 A | 4/2000 | Wagner et al. | |
| 6,063,089 A | 5/2000 | Errico et al. | |
| RE36,758 E | 6/2000 | Fitz | |
| 6,080,193 A | 6/2000 | Hochshuler et al. | |
| 6,093,205 A | 7/2000 | McLeod et al. | |
| 6,096,038 A | 8/2000 | Michelson | |
| 6,099,531 A | 8/2000 | Bonutti | |
| 6,102,950 A * | 8/2000 | Vaccaro | 623/17.16 |
| 6,106,526 A | 8/2000 | Harms et al. | |
| 6,110,210 A | 8/2000 | Norton et al. | |
| 6,113,637 A | 9/2000 | Gill et al. | |
| 6,123,707 A | 9/2000 | Wagner et al. | |
| 6,126,689 A | 10/2000 | Brett | |
| 6,132,430 A | 10/2000 | Wagner et al. | |
| 6,132,464 A | 10/2000 | Martin | |
| 6,132,465 A | 10/2000 | Ray et al. | |
| 6,136,001 A | 10/2000 | Michelson | |
| 6,136,031 A | 10/2000 | Middleton | |
| 6,139,579 A | 10/2000 | Steffee et al. | |
| 6,146,421 A | 11/2000 | Gordon et al. | |
| 6,146,422 A | 11/2000 | Lawson | |
| 6,156,067 A | 12/2000 | Bryan et al. | |
| 6,159,244 A | 12/2000 | Suddaby | |
| 6,162,252 A | 12/2000 | Kuras et al. | |
| 6,165,218 A | 12/2000 | Husson et al. | |
| 6,176,882 B1 | 1/2001 | Biedermann et al. | |
| 6,179,874 B1 | 1/2001 | Cauthen | |
| 6,187,048 B1 | 2/2001 | Milner et al. | |
| 6,200,348 B1 | 3/2001 | Biedermann et al. | |
| 6,206,924 B1 | 3/2001 | Timm | |
| 6,214,049 B1 | 4/2001 | Gayer et al. | |
| 6,214,050 B1 | 4/2001 | Huene | |
| 6,217,579 B1 | 4/2001 | Koros | |
| 6,228,118 B1 | 5/2001 | Gordon | |
| 6,231,609 B1 | 5/2001 | Mehdizadeh | |
| 6,241,730 B1 | 6/2001 | Alby | |
| 6,264,656 B1 | 7/2001 | Michelson | |
| 6,290,724 B1 | 9/2001 | Marino | |
| 6,296,664 B1 | 10/2001 | Middleton | |
| 6,315,797 B1 | 11/2001 | Middleton | |
| 6,331,179 B1 | 12/2001 | Freid et al. | |
| 6,348,071 B1 | 2/2002 | Steffee et al. | |
| RE37,665 E | 4/2002 | Ralph et al. | |
| 6,368,350 B1 | 4/2002 | Erickson | |
| 6,368,351 B1 | 4/2002 | Glenn et al. | |
| 6,371,990 B1 | 4/2002 | Ferree | |
| 6,375,682 B1 | 4/2002 | Fleischmann et al. | |
| 6,375,683 B1 | 4/2002 | Crozet et al. | |
| 6,391,030 B1 | 5/2002 | Wagner et al. | |
| 6,395,032 B1 | 5/2002 | Gauchet | |
| 6,395,034 B1 | 5/2002 | Suddaby | |
| 6,402,784 B1 | 6/2002 | Wardlaw | |
| 6,402,785 B1 | 6/2002 | Zdeblick et al. | |
| 6,409,766 B1 | 6/2002 | Brett | |
| 6,413,259 B1 | 7/2002 | Lyons et al. | |
| 6,416,515 B1 | 7/2002 | Wagner et al. | |
| 6,419,703 B1 | 7/2002 | Fallin et al. | |
| 6,419,704 B1 | 7/2002 | Ferree | |
| 6,436,140 B1 | 8/2002 | Liu et al. | |
| 6,440,168 B1 | 8/2002 | Cauthen | |
| 6,442,814 B1 | 9/2002 | Landry et al. | |
| 6,443,990 B1 | 9/2002 | Aebi et al. | |
| 6,447,512 B1 | 9/2002 | Landry et al. | |
| 6,447,544 B1 | 9/2002 | Michelson | |
| 6,447,545 B1 | 9/2002 | Bagby | |
| 6,451,021 B1 | 9/2002 | Ralph et al. | |
| 6,454,769 B2 | 9/2002 | Wagner et al. | |
| 6,454,806 B1 | 9/2002 | Cohen et al. | |
| 6,454,807 B1 | 9/2002 | Jackson | |
| 6,475,218 B2 | 11/2002 | Gournay et al. | |
| 6,478,822 B1 | 11/2002 | Leroux et al. | |
| 6,478,823 B1 | 11/2002 | Michelson | |
| 6,482,207 B1 | 11/2002 | Errico | |
| 6,482,234 B1 | 11/2002 | Weber et al. | |
| 6,488,710 B2 | 12/2002 | Besselink | |
| 6,491,724 B1 | 12/2002 | Ferree | |
| 6,500,180 B1 | 12/2002 | Foley et al. | |
| 6,500,205 B1 | 12/2002 | Michelson | |
| 6,500,206 B1 | 12/2002 | Bryan | |
| 6,520,996 B1 | 2/2003 | Manasas et al. | |
| 6,524,312 B2 | 2/2003 | Landry et al. | |
| 6,533,817 B1 | 3/2003 | Norton et al. | |
| 6,533,818 B1 | 3/2003 | Weber et al. | |
| 6,537,320 B1 | 3/2003 | Michelson | |
| 6,540,748 B2 | 4/2003 | Lombardo | |
| 6,558,423 B1 | 5/2003 | Michelson | |
| 6,558,424 B2 | 5/2003 | Thalgott | |
| 6,562,040 B1 | 5/2003 | Wagner et al. | |
| 6,562,074 B2 | 5/2003 | Gerbec et al. | |
| 6,565,566 B1 | 5/2003 | Wagner et al. | |
| 6,565,605 B2 | 5/2003 | Goble et al. | |
| 6,569,442 B2 | 5/2003 | Gan et al. | |
| 6,572,653 B1 | 6/2003 | Simonson | |
| 6,576,016 B1 | 6/2003 | Hochshuler et al. | |
| 6,579,318 B2 | 6/2003 | Varga et al. | |
| 6,579,319 B2 | 6/2003 | Goble et al. | |
| 6,582,467 B1 | 6/2003 | Teitelbaum et al. | |
| 6,592,624 B1 | 7/2003 | Fraser et al. | |
| 6,595,992 B1 | 7/2003 | Wagner et al. | |
| 6,595,998 B2 | 7/2003 | Johnson et al. | |
| 6,607,530 B1 | 8/2003 | Carl et al. | |
| 6,610,091 B1 | 8/2003 | Reiley | |
| 6,610,094 B2 | 8/2003 | Husson | |
| 6,613,050 B1 | 9/2003 | Wagner et al. | |
| 6,616,671 B2 | 9/2003 | Landry et al. | |
| 6,626,904 B1 | 9/2003 | Jammet et al. | |
| 6,626,905 B1 | 9/2003 | Schmiel et al. | |
| 6,635,062 B2 | 10/2003 | Ray et al. | |
| 6,641,614 B1 | 11/2003 | Wagner et al. | |

(56) References Cited

U.S. PATENT DOCUMENTS

| | | |
|---|---|---|
| 6,648,893 B2 | 11/2003 | Dudasik |
| 6,648,915 B2 | 11/2003 | Sazy |
| 6,648,917 B2 | 11/2003 | Gerbec et al. |
| 6,666,870 B2 | 12/2003 | Dixon |
| 6,666,891 B2 | 12/2003 | Boehm et al. |
| 6,679,915 B1 | 1/2004 | Cauthen |
| 6,682,533 B1 | 1/2004 | Dinsdale et al. |
| 6,685,742 B1 | 2/2004 | Jackson |
| 6,692,495 B1 | 2/2004 | Zacouto |
| 6,706,070 B1 | 3/2004 | Wagner et al. |
| 6,712,819 B2 | 3/2004 | Zucherman et al. |
| 6,716,247 B2 | 4/2004 | Michelson |
| 6,719,796 B2 | 4/2004 | Cohen et al. |
| 6,733,531 B1 | 5/2004 | Trieu |
| 6,736,850 B2 | 5/2004 | Davis |
| 6,743,257 B2 | 6/2004 | Castro |
| 6,758,861 B2 | 7/2004 | Ralph et al. |
| 6,773,460 B2 | 8/2004 | Jackson |
| 6,802,844 B2 | 10/2004 | Ferree |
| 6,811,567 B2 | 11/2004 | Reiley |
| 6,821,298 B1 | 11/2004 | Jackson |
| 6,852,129 B2 | 2/2005 | Gerbec et al. |
| 6,863,673 B2 | 3/2005 | Gerbec et al. |
| 6,893,464 B2 | 5/2005 | Kiester |
| 6,896,680 B2 | 5/2005 | Michelson |
| 6,902,580 B2 | 6/2005 | Fallin et al. |
| 6,928,284 B2 | 8/2005 | Palat et al. |
| 6,936,070 B1 | 8/2005 | Muhanna |
| 6,936,071 B1 | 8/2005 | Marnay et al. |
| 6,953,477 B2 | 10/2005 | Berry |
| 6,962,606 B2 | 11/2005 | Michelson |
| 6,964,664 B2 | 11/2005 | Freid et al. |
| 6,966,929 B2 | 11/2005 | Mitchell |
| 6,966,930 B2 | 11/2005 | Arnin et al. |
| 6,974,478 B2 | 12/2005 | Reiley et al. |
| 6,981,989 B1 | 1/2006 | Fleischmann et al. |
| 6,991,632 B2 | 1/2006 | Ritland |
| 6,994,727 B2 | 2/2006 | Khandkar et al. |
| 6,997,929 B2 | 2/2006 | Manzi et al. |
| 7,011,685 B2 | 3/2006 | Arnin et al. |
| 7,018,415 B1 | 3/2006 | McKay |
| 7,029,475 B2 | 4/2006 | Panjabi |
| 7,060,073 B2 | 6/2006 | Frey et al. |
| 7,060,100 B2 | 6/2006 | Ferree |
| 7,083,622 B2 | 8/2006 | Simonson |
| 7,083,649 B2 | 8/2006 | Zucherman et al. |
| 7,090,698 B2 | 8/2006 | Goble et al. |
| 7,101,398 B2 | 9/2006 | Dooris et al. |
| 7,118,579 B2 | 10/2006 | Michelson |
| 7,118,580 B1 | 10/2006 | Beyersdorff et al. |
| 7,128,760 B2 | 10/2006 | Michelson |
| 7,147,664 B2 | 12/2006 | Louis et al. |
| 7,153,310 B2 | 12/2006 | Ralph et al. |
| 7,198,644 B2 | 4/2007 | Schultz et al. |
| 7,204,852 B2 | 4/2007 | Marnay et al. |
| 7,204,853 B2 | 4/2007 | Gordon et al. |
| 7,270,681 B2 | 9/2007 | Cauthen |
| 7,273,496 B2 | 9/2007 | Mitchell |
| 7,291,150 B2 | 11/2007 | Graf |
| 7,291,173 B2 | 11/2007 | Richelsoph et al. |
| 7,311,713 B2 | 12/2007 | Johnson et al. |
| 7,316,714 B2 | 1/2008 | Gordon et al. |
| 7,318,839 B2 | 1/2008 | Malberg et al. |
| 7,320,707 B2 | 1/2008 | Zucherman et al. |
| 7,326,250 B2 | 2/2008 | Beaurain et al. |
| 7,338,525 B2 | 3/2008 | Ferree |
| 7,338,527 B2 | 3/2008 | Blatt et al. |
| 7,364,589 B2 | 4/2008 | Eisermann |
| 7,473,276 B2 | 1/2009 | Aebi et al. |
| 7,476,238 B2 | 1/2009 | Panjabi |
| 7,485,146 B1 | 2/2009 | Crook et al. |
| 7,517,359 B2 | 4/2009 | Drewry et al. |
| 7,547,309 B2 | 6/2009 | Bertagnoli et al. |
| 7,550,009 B2 | 6/2009 | Arnin et al. |
| 7,556,651 B2 | 7/2009 | Humphreys et al. |
| 7,615,068 B2 | 11/2009 | Timm et al. |
| 7,635,379 B2 | 12/2009 | Callahan et al. |
| 7,682,396 B2 | 3/2010 | Beaurain et al. |
| 7,699,875 B2 | 4/2010 | Timm |
| 7,708,778 B2 | 5/2010 | Gordon et al. |
| 7,713,287 B2 | 5/2010 | Timm et al. |
| 7,713,288 B2 | 5/2010 | Timm et al. |
| 7,727,280 B2 | 6/2010 | McLuen |
| 7,753,958 B2 | 7/2010 | Gordon et al. |
| 7,771,479 B2 | 8/2010 | Humphreys et al. |
| 7,785,351 B2 | 8/2010 | Gordon et al. |
| 7,794,480 B2 | 9/2010 | Gordon et al. |
| 7,799,082 B2 | 9/2010 | Gordon et al. |
| 7,811,309 B2 | 10/2010 | Timm et al. |
| 7,819,801 B2 | 10/2010 | Miles et al. |
| 7,828,849 B2 | 11/2010 | Lim |
| 7,896,919 B2 | 3/2011 | Belliard et al. |
| 7,909,869 B2 | 3/2011 | Gordon et al. |
| 7,909,877 B2 | 3/2011 | Krueger et al. |
| 7,927,374 B2 | 4/2011 | Duggal et al. |
| 7,931,675 B2 | 4/2011 | Panjabi et al. |
| 7,942,905 B2 | 5/2011 | Lim et al. |
| 7,951,170 B2 | 5/2011 | Jackson |
| 7,959,677 B2 | 6/2011 | Landry et al. |
| 8,043,379 B2 | 10/2011 | Moumene et al. |
| 8,052,723 B2 | 11/2011 | Gordon et al. |
| 8,062,375 B2 | 11/2011 | Glerum et al. |
| 8,105,382 B2 | 1/2012 | Olmos et al. |
| 8,118,869 B2 | 2/2012 | Gordon et al. |
| 8,118,870 B2 | 2/2012 | Gordon et al. |
| 8,118,871 B2 | 2/2012 | Gordon et al. |
| 8,123,810 B2 | 2/2012 | Gordon et al. |
| 8,128,700 B2 | 3/2012 | Delurio et al. |
| 8,147,550 B2 | 4/2012 | Gordon et al. |
| 8,157,844 B2 | 4/2012 | Gimbel et al. |
| 8,162,994 B2 | 4/2012 | Gimbel et al. |
| 8,172,903 B2 | 5/2012 | Gordon et al. |
| 8,182,514 B2 | 5/2012 | Gimbel et al. |
| 8,187,330 B2 | 5/2012 | Gimbel et al. |
| 8,257,440 B2 | 9/2012 | Gordon et al. |
| 8,267,965 B2 | 9/2012 | Gimbel et al. |
| 8,303,660 B1 | 11/2012 | Abdou |
| 8,377,098 B2 | 2/2013 | Landry et al. |
| 8,388,687 B2 | 3/2013 | Gimbel et al. |
| 8,398,713 B2 | 3/2013 | Weiman |
| 8,414,652 B2 | 4/2013 | Moumene et al. |
| 8,435,298 B2 | 5/2013 | Weiman |
| 8,475,461 B2 | 7/2013 | Butler et al. |
| 8,486,148 B2 | 7/2013 | Butler et al. |
| 8,491,659 B2 | 7/2013 | Weiman |
| 8,512,407 B2 | 8/2013 | Butler et al. |
| 8,518,120 B2 | 8/2013 | Glerum et al. |
| 8,523,912 B2 | 9/2013 | Gimbel et al. |
| 8,556,979 B2 | 10/2013 | Glerum et al. |
| 8,591,553 B2 | 11/2013 | Eisermann et al. |
| 8,597,358 B2 | 12/2013 | Landry et al. |
| 8,603,168 B2 | 12/2013 | Gordon et al. |
| 8,632,595 B2 | 1/2014 | Weiman |
| 8,647,386 B2 | 2/2014 | Gordon et al. |
| 8,679,183 B2 | 3/2014 | Glerum et al. |
| 8,685,098 B2 | 4/2014 | Glerum et al. |
| 8,709,086 B2 | 4/2014 | Glerum |
| 8,753,398 B2 | 6/2014 | Gordon et al. |
| 8,940,022 B2 | 1/2015 | Landry et al. |
| 8,940,051 B2 | 1/2015 | Gimbel et al. |
| 2001/0020476 A1 | 9/2001 | Gan et al. |
| 2001/0032020 A1 | 10/2001 | Besselink |
| 2002/0040243 A1 | 4/2002 | Attalli et al. |
| 2002/0045945 A1 | 4/2002 | Liu et al. |
| 2002/0065557 A1 | 5/2002 | Goble et al. |
| 2002/0068977 A1 | 6/2002 | Jackson |
| 2002/0072801 A1 | 6/2002 | Michelson |
| 2002/0082701 A1 | 6/2002 | Zdeblick et al. |
| 2002/0091390 A1 | 7/2002 | Michelson |
| 2002/0095154 A1 | 7/2002 | Atkinson et al. |
| 2002/0123806 A1 | 9/2002 | Reiley |
| 2002/0128659 A1 | 9/2002 | Michelson |
| 2002/0128714 A1 | 9/2002 | Manasas et al. |
| 2002/0130112 A1 | 9/2002 | Manasas et al. |

(56) References Cited

U.S. PATENT DOCUMENTS

| | | |
|---|---|---|
| 2002/0138077 A1 | 9/2002 | Ferree |
| 2002/0143401 A1 | 10/2002 | Michelson |
| 2003/0028250 A1 | 2/2003 | Reiley et al. |
| 2003/0040802 A1 | 2/2003 | Errico |
| 2003/0055427 A1 | 3/2003 | Graf |
| 2003/0065396 A1* | 4/2003 | Michelson .......... A61F 2/30744 623/17.15 |
| 2003/0069643 A1 | 4/2003 | Ralph et al. |
| 2003/0074063 A1 | 4/2003 | Gerbec et al. |
| 2003/0074066 A1 | 4/2003 | Errico et al. |
| 2003/0074067 A1 | 4/2003 | Errico et al. |
| 2003/0074068 A1 | 4/2003 | Errico et al. |
| 2003/0074069 A1 | 4/2003 | Errico et al. |
| 2003/0074070 A1 | 4/2003 | Errico et al. |
| 2003/0074071 A1 | 4/2003 | Errico et al. |
| 2003/0074072 A1 | 4/2003 | Errico et al. |
| 2003/0074073 A1 | 4/2003 | Errico et al. |
| 2003/0074074 A1 | 4/2003 | Errico et al. |
| 2003/0135275 A1 | 7/2003 | Garcia et al. |
| 2003/0135277 A1 | 7/2003 | Bryan et al. |
| 2003/0139812 A1 | 7/2003 | Gacia et al. |
| 2003/0149483 A1 | 8/2003 | Michelson |
| 2003/0176923 A1 | 9/2003 | Keller et al. |
| 2003/0191470 A1 | 10/2003 | Ritland |
| 2003/0204259 A1 | 10/2003 | Goble et al. |
| 2003/0204260 A1 | 10/2003 | Ferree |
| 2003/0220643 A1 | 11/2003 | Ferree |
| 2003/0225409 A1 | 12/2003 | Freid et al. |
| 2003/0233145 A1 | 12/2003 | Landry et al. |
| 2004/0006391 A1 | 1/2004 | Reiley |
| 2004/0019353 A1 | 1/2004 | Freid et al. |
| 2004/0030387 A1 | 2/2004 | Landry et al. |
| 2004/0030389 A1 | 2/2004 | Ferree |
| 2004/0039448 A1 | 2/2004 | Pisharodi |
| 2004/0044411 A1 | 3/2004 | Suddaby |
| 2004/0049190 A1 | 3/2004 | Biedermann et al. |
| 2004/0049271 A1 | 3/2004 | Biedermann et al. |
| 2004/0049272 A1 | 3/2004 | Reiley |
| 2004/0049273 A1 | 3/2004 | Reiley |
| 2004/0049274 A1 | 3/2004 | Reiley |
| 2004/0049275 A1 | 3/2004 | Reiley |
| 2004/0049276 A1 | 3/2004 | Reiley |
| 2004/0049277 A1 | 3/2004 | Reiley |
| 2004/0049278 A1 | 3/2004 | Reiley |
| 2004/0049280 A1 | 3/2004 | Cauthen |
| 2004/0049281 A1 | 3/2004 | Reiley |
| 2004/0087947 A1 | 5/2004 | Lim et al. |
| 2004/0093083 A1 | 5/2004 | Branch et al. |
| 2004/0102774 A1 | 5/2004 | Trieu |
| 2004/0106997 A1 | 6/2004 | Lieberson |
| 2004/0117020 A1 | 6/2004 | Frey et al. |
| 2004/0127989 A1 | 7/2004 | Dooris et al. |
| 2004/0133278 A1 | 7/2004 | Marino et al. |
| 2004/0133281 A1 | 7/2004 | Khandkar et al. |
| 2004/0138662 A1 | 7/2004 | Landry et al. |
| 2004/0138749 A1 | 7/2004 | Zucherman |
| 2004/0143265 A1 | 7/2004 | Landry et al. |
| 2004/0143332 A1 | 7/2004 | Krueger et al. |
| 2004/0147928 A1 | 7/2004 | Landry et al. |
| 2004/0153065 A1 | 8/2004 | Lim |
| 2004/0167626 A1 | 8/2004 | Geremakis et al. |
| 2004/0181223 A1 | 9/2004 | Ritland |
| 2004/0181284 A1 | 9/2004 | Simonson |
| 2004/0220567 A1 | 11/2004 | Eisermann et al. |
| 2004/0236327 A1 | 11/2004 | Paul et al. |
| 2004/0236329 A1 | 11/2004 | Panjabi |
| 2004/0243240 A1 | 12/2004 | Beaurain et al. |
| 2004/0254643 A1 | 12/2004 | Jackson |
| 2004/0254644 A1 | 12/2004 | Taylor |
| 2004/0267364 A1 | 12/2004 | Carli et al. |
| 2004/0267369 A1 | 12/2004 | Lyons et al. |
| 2005/0010295 A1 | 1/2005 | Michelson |
| 2005/0015146 A1 | 1/2005 | Louis et al. |
| 2005/0015149 A1 | 1/2005 | Michelson |
| 2005/0021144 A1 | 1/2005 | Malberg et al. |
| 2005/0027361 A1 | 2/2005 | Reiley |
| 2005/0033431 A1 | 2/2005 | Gordon et al. |
| 2005/0033432 A1 | 2/2005 | Gordon et al. |
| 2005/0033437 A1 | 2/2005 | Bao et al. |
| 2005/0033439 A1 | 2/2005 | Gordon et al. |
| 2005/0043800 A1 | 2/2005 | Paul et al. |
| 2005/0060034 A1 | 3/2005 | Berry |
| 2005/0085815 A1 | 4/2005 | Harms et al. |
| 2005/0107881 A1 | 5/2005 | Alleyne et al. |
| 2005/0113927 A1 | 5/2005 | Malek |
| 2005/0117725 A1 | 6/2005 | Baker |
| 2005/0124991 A1 | 6/2005 | Jahng |
| 2005/0125061 A1 | 6/2005 | Zucherman et al. |
| 2005/0125062 A1 | 6/2005 | Biedermann et al. |
| 2005/0131406 A1 | 6/2005 | Reiley |
| 2005/0143818 A1 | 6/2005 | Yuan et al. |
| 2005/0149020 A1 | 7/2005 | Jahng |
| 2005/0149023 A1 | 7/2005 | Ritland |
| 2005/0154461 A1 | 7/2005 | Humphreys et al. |
| 2005/0154462 A1 | 7/2005 | Zucherman et al. |
| 2005/0154465 A1 | 7/2005 | Hodges et al. |
| 2005/0154466 A1 | 7/2005 | Humphreys et al. |
| 2005/0159818 A1 | 7/2005 | Blain |
| 2005/0171543 A1 | 8/2005 | Timm et al. |
| 2005/0171608 A1 | 8/2005 | Peterman et al. |
| 2005/0171610 A1 | 8/2005 | Humphreys et al. |
| 2005/0177156 A1 | 8/2005 | Timm et al. |
| 2005/0177157 A1 | 8/2005 | Jahng |
| 2005/0177164 A1 | 8/2005 | Walters et al. |
| 2005/0177166 A1 | 8/2005 | Timm et al. |
| 2005/0182401 A1 | 8/2005 | Timm et al. |
| 2005/0182409 A1 | 8/2005 | Callahan et al. |
| 2005/0203517 A1 | 9/2005 | Jahng et al. |
| 2005/0209697 A1 | 9/2005 | Paponneau et al. |
| 2005/0209698 A1 | 9/2005 | Gordon et al. |
| 2005/0222569 A1 | 10/2005 | Panjabi |
| 2005/0228500 A1 | 10/2005 | Kim et al. |
| 2005/0245930 A1 | 11/2005 | Timm et al. |
| 2005/0251261 A1 | 11/2005 | Peterman |
| 2005/0256578 A1 | 11/2005 | Blatt et al. |
| 2005/0261771 A1 | 11/2005 | Paul et al. |
| 2005/0273167 A1 | 12/2005 | Triplett et al. |
| 2005/0273171 A1 | 12/2005 | Gordon et al. |
| 2005/0273173 A1 | 12/2005 | Gordon et al. |
| 2005/0273174 A1 | 12/2005 | Gordon et al. |
| 2005/0273175 A1 | 12/2005 | Gordon et al. |
| 2005/0278026 A1 | 12/2005 | Gordon et al. |
| 2005/0283244 A1 | 12/2005 | Gordon et al. |
| 2005/0283245 A1 | 12/2005 | Gordon et al. |
| 2005/0283247 A1 | 12/2005 | Gordon et al. |
| 2005/0283248 A1 | 12/2005 | Gordon et al. |
| 2005/0288670 A1 | 12/2005 | Panjabi et al. |
| 2006/0009768 A1 | 1/2006 | Ritland |
| 2006/0009850 A1 | 1/2006 | Frigg et al. |
| 2006/0015100 A1 | 1/2006 | Panjabi et al. |
| 2006/0036240 A1 | 2/2006 | Colleran |
| 2006/0036245 A1 | 2/2006 | Stern |
| 2006/0084986 A1 | 4/2006 | Grinberg et al. |
| 2006/0089717 A1 | 4/2006 | Krishna et al. |
| 2006/0095132 A1 | 5/2006 | Kirschman |
| 2006/0122701 A1 | 6/2006 | Kiester |
| 2006/0129244 A1 | 6/2006 | Ensign |
| 2006/0142759 A1 | 6/2006 | Arnin et al. |
| 2006/0149228 A1 | 7/2006 | Schlapfer et al. |
| 2006/0149229 A1 | 7/2006 | Kwak et al. |
| 2006/0149278 A1 | 7/2006 | Abdou |
| 2006/0149372 A1 | 7/2006 | Paxson et al. |
| 2006/0149383 A1 | 7/2006 | Arnin et al. |
| 2006/0149385 A1 | 7/2006 | McKay |
| 2006/0155377 A1 | 7/2006 | Beaurain et al. |
| 2006/0167547 A1 | 7/2006 | Suddaby |
| 2006/0189983 A1 | 8/2006 | Fallin et al. |
| 2006/0195114 A1 | 8/2006 | Bertagnoli |
| 2006/0195191 A1 | 8/2006 | Sweeney et al. |
| 2006/0195192 A1 | 8/2006 | Gordon et al. |
| 2006/0217712 A1 | 9/2006 | Mueller et al. |
| 2006/0229729 A1 | 10/2006 | Gordon et al. |
| 2006/0241642 A1 | 10/2006 | Arnin et al. |
| 2006/0241769 A1 | 10/2006 | Gordon et al. |

(56) References Cited

U.S. PATENT DOCUMENTS

| | | |
|---|---|---|
| 2006/0241770 A1 | 10/2006 | Rhoda et al. |
| 2006/0241771 A1 | 10/2006 | Gordon et al. |
| 2006/0247635 A1 | 11/2006 | Gordon et al. |
| 2006/0247779 A1 | 11/2006 | Gordon et al. |
| 2006/0260483 A1 | 11/2006 | Hartmann et al. |
| 2006/0264937 A1 | 11/2006 | White |
| 2006/0265068 A1 | 11/2006 | Schwab |
| 2006/0265074 A1 | 11/2006 | Krishna |
| 2007/0010886 A1 | 1/2007 | Banick |
| 2007/0073405 A1 | 3/2007 | Verhulst et al. |
| 2007/0073406 A1 | 3/2007 | Gordon et al. |
| 2007/0093828 A1 | 4/2007 | Abdou |
| 2007/0093846 A1 | 4/2007 | Frigg et al. |
| 2007/0162137 A1 | 7/2007 | Kloss et al. |
| 2007/0213720 A1 | 9/2007 | Gordon et al. |
| 2007/0213821 A1 | 9/2007 | Kwak et al. |
| 2007/0225814 A1 | 9/2007 | Atkinson et al. |
| 2007/0239279 A1 | 10/2007 | Francis |
| 2007/0270814 A1 | 11/2007 | Lim et al. |
| 2007/0270838 A1 | 11/2007 | Bruneau et al. |
| 2007/0270972 A1 | 11/2007 | Gordon et al. |
| 2007/0288094 A1 | 12/2007 | Krishna et al. |
| 2008/0015702 A1 | 1/2008 | Lakin et al. |
| 2008/0021285 A1 | 1/2008 | Drzyzga et al. |
| 2008/0027547 A1 | 1/2008 | Yu et al. |
| 2008/0033562 A1 | 2/2008 | Krishna |
| 2008/0065079 A1 | 3/2008 | Bruneau et al. |
| 2008/0133013 A1 | 6/2008 | Duggal et al. |
| 2008/0161853 A1 | 7/2008 | Arnold et al. |
| 2008/0177310 A1 | 7/2008 | Reiley |
| 2008/0183204 A1 | 7/2008 | Greenhalgh et al. |
| 2008/0234732 A1 | 9/2008 | Landry et al. |
| 2008/0234740 A1 | 9/2008 | Landry et al. |
| 2008/0234741 A1 | 9/2008 | Landry et al. |
| 2008/0234764 A1 | 9/2008 | Landry et al. |
| 2008/0234823 A1 | 9/2008 | Landry et al. |
| 2008/0300685 A1 | 12/2008 | Carls et al. |
| 2008/0312692 A1 | 12/2008 | Brennan et al. |
| 2009/0005817 A1 | 1/2009 | Friedrich et al. |
| 2009/0076549 A1 | 3/2009 | Lim et al. |
| 2009/0093846 A1 | 4/2009 | Hestad |
| 2009/0105757 A1 | 4/2009 | Gimbel et al. |
| 2009/0105758 A1 | 4/2009 | Gimbel et al. |
| 2009/0105759 A1 | 4/2009 | Gimbel et al. |
| 2009/0105764 A1 | 4/2009 | Jackson |
| 2009/0105820 A1 | 4/2009 | Jackson |
| 2009/0105827 A1 | 4/2009 | Gimbel et al. |
| 2009/0105828 A1 | 4/2009 | Gimbel et al. |
| 2009/0105829 A1 | 4/2009 | Gimbel et al. |
| 2009/0143862 A1 | 6/2009 | Trieu |
| 2009/0177196 A1 | 7/2009 | Zlock et al. |
| 2009/0270870 A1 | 10/2009 | Zubok et al. |
| 2010/0030336 A1 | 2/2010 | Cope |
| 2010/0082109 A1 | 4/2010 | Greenhalgh et al. |
| 2010/0174317 A1 | 7/2010 | Timm et al. |
| 2010/0191336 A1 | 7/2010 | Greenhalgh |
| 2010/0204795 A1 | 8/2010 | Greenhalgh |
| 2010/0211176 A1 | 8/2010 | Greenhalgh |
| 2010/0222819 A1 | 9/2010 | Timm et al. |
| 2010/0222884 A1 | 9/2010 | Greenhalgh |
| 2010/0292796 A1 | 11/2010 | Greenhalgh et al. |
| 2010/0298941 A1 | 11/2010 | Hes et al. |
| 2010/0331985 A1 | 12/2010 | Gordon et al. |
| 2011/0015742 A1 | 1/2011 | Hong |
| 2011/0196428 A1 | 8/2011 | Panjabi et al. |
| 2011/0319997 A1 | 12/2011 | Glerum et al. |
| 2012/0035729 A1 | 2/2012 | Glerum et al. |
| 2012/0143254 A1 | 6/2012 | Gimbel et al. |
| 2012/0245689 A1 | 9/2012 | Gimbel et al. |
| 2012/0265309 A1 | 10/2012 | Glerum et al. |
| 2012/0310349 A1 | 12/2012 | Gordon et al. |
| 2013/0023994 A1 | 1/2013 | Glerum |
| 2013/0158667 A1 | 6/2013 | Tabor et al. |
| 2013/0158669 A1 | 6/2013 | Sungarian et al. |
| 2013/0245769 A1 | 9/2013 | Gimbel et al. |
| 2014/0067071 A1 | 3/2014 | Weiman et al. |

FOREIGN PATENT DOCUMENTS

| | | |
|---|---|---|
| FR | 2718946 | 10/1995 |
| FR | 2735351 | 12/1996 |
| FR | 2745706 | 9/1997 |
| FR | 2799949 | 4/2001 |
| RU | 2085145 | 7/1997 |
| WO | 9848739 | 11/1998 |
| WO | 0004851 | 2/2000 |
| WO | 0074606 | 12/2000 |
| WO | 0101893 | 1/2001 |
| WO | 0156513 | 8/2001 |
| WO | 0245625 | 6/2002 |
| WO | 2004019762 | 3/2004 |
| WO | 2004019828 | 3/2004 |
| WO | 2004019830 | 3/2004 |
| WO | 2004024011 | 3/2004 |
| WO | 2004026188 | 4/2004 |
| WO | 2004041129 | 5/2004 |
| WO | 2004054479 | 7/2004 |
| WO | 2005016194 | 2/2005 |
| WO | 2005067824 | 7/2005 |
| WO | 2005070349 | 8/2005 |
| WO | 2005117725 | 12/2005 |
| WO | 2006002359 | 1/2006 |
| WO | 2006047587 | 5/2006 |
| WO | 2006057698 | 6/2006 |
| WO | 2006066198 | 6/2006 |
| WO | 2006116851 | 11/2006 |
| WO | 2006119447 | 11/2006 |
| WO | 2007104024 | 9/2007 |
| WO | 2008089350 | 7/2008 |
| WO | 2012134980 | 10/2012 |

OTHER PUBLICATIONS

E.P.O. Communication Pursuant to Article 94(3) for European Application No. 07 758 171.8 mailed on Feb. 26, 2013.

U. S. P.T. O. Non-Final Office Action for U.S. Appl. No. 13/437,604, mailed Jul. 2, 2014.

U. S. P.T. O. Advisory Action for U.S. Appl. No. 12/841,792, mailed Jul. 19, 2012.

U. S. P. T. O. Final Office Action for U.S. Appl. No. 11/345,602, mailed Aug. 13, 2012.

U. S. P. T. O. Final Office Action for U.S. Appl. No. 11/655,724, mailed Aug. 24, 2012.

U. S. P.T. O. Non-Final Office Action for U.S. Appl. No. 13/306,535, mailed Aug. 24, 2012.

Co-pending U.S. Appl. No. 13/306,535 entitled "Posterior Stabilization Systems With Shared, Dual Dampener Systems" to Gimbel et al., filed Nov. 29, 2011.

Co-pending U.S. Appl. No. 13/072,511 entitled "Instrumentation for Artificial Functional Spinal Unit System" to Gimbel et al., filed Mar. 25, 2012.

Co-pending U.S. Appl. No. 13/437,604 entitled "Method of Inserting an Expandable Intervertebral Implant Without Overdistraction" to Gordon et al., filed Apr. 2, 2012.

U. S. P.T. O. Advisory Action for U.S. Appl. No. 11/134,055, mailed Jul. 8, 2013.

U. S. P.T. O. Final Office Action for U.S. Appl. No. 13/306,535, mailed Jul. 18, 2013.

U. S. P.T. O. Advisory Action for U.S. Appl. No. 13/306,535, mailed Sep. 9, 2013.

Co-pending U.S. Appl. No. 13/967,776 entitled "Expandable Intervertebral Implant" to Gordon et al., filed Aug. 15, 2013.

E.P. Communication Pursuant to Article 94(3) EPC for Application No. 08713804.6-2310 mailed Dec. 5, 2013.

International Preliminary Report on Patentability for International Application No. PCT/US2012/030248 mailed Oct. 23, 2012, 11 pages.

(56) References Cited

OTHER PUBLICATIONS

U. S. P.T. O. Non-Final Office Action for U.S. Appl. No. 11/655,737, mailed Mar. 15, 2013.
U. S. P.T. O. Notice of Allowance for U.S. Appl. No. 11/975,916, mailed Jan. 28, 2013.
Co-pending U.S. Appl. No. 13/784,224 entitled "Interbody Device Insertion Systems and Methods" to Gimbel et al., filed Mar. 4, 2013.
E.P. Communication Pursuant to Article 94(3) EPC for Application No. 08713804.6-2310 mailed Jan. 22, 2013.
J.P. Notice of Reason for Refusal for Japanese Application No. 2009-546510 mailed on Oct. 9, 2012.
U. S. P. T. O. Non-Final Office Action for U.S. Appl. No. 11/655,724, mailed Feb. 17, 2012.
U. S. P.T. O. Notice of Allowance for U.S. Appl. No. 11/975,918, mailed Jan. 19, 2012.
U. S. P.T. O. Notice of Allowance for U.S. Appl. No. 11/975,917, mailed Feb. 1, 2012.
U. S. P.T. O. Final Office Action for U.S. Appl. No. 11/975,919, mailed Jan. 27, 2012.
U. S. P.T. O. Final Office Action for U.S. Appl. No. 11/134,091, mailed Feb. 10, 2012.
U. S. P.T. O. Notice of Allowance for U.S. Appl. No. 11/134,082, mailed Jan. 11, 2012.
U. S. P.T. O. Advisory Action for U.S. Appl. No. 11/134,055, mailed Feb. 15, 2012.
J.P. Notice of Reason for Refusal for Japanese Application No. 2008-558536 considered by Examiner on Jan. 12, 2012.
U. S. P.T. O. Notice of Allowance for U.S. Appl. No. 11/134,091, mailed May 4, 2012.
U. S. P.T. O. Final Office Action for U.S. Appl. No. 12/841,792, mailed Mar. 23, 2012.
U. S. P.T. O. Non-Final Office Action for U.S. Appl. No. 11/345,602, mailed Mar. 5, 2012.
U. S. P.T. O. Non-Final Office Action for U.S. Appl. No. 11/371,376, mailed Mar. 23, 2012.
U. S. P.T. O. Notice of Allowance for U.S. Appl. No. 11/975,919, mailed May 11, 2012.
U. S. P. T. O. Non-Final Office Action for U.S. Appl. No. 13/306,535, mailed May 24, 2012.
E.P.O. Report of Deficiencies for European Application No. 07 758 171.8-2310 mailed on Feb. 13, 2012.
J.P. Notice of Reason for Refusal for Japanese Application No. 2009-546510 mailed on Mar. 6, 2012.
U. S. P. T. O. Non-Final Office Action for U.S. Appl. No. 10/634,950, mailed Dec. 1, 2005.
U. S. P.T. O. Non-Final Office Action for U.S. Appl. No. 11/655,787, mailed May 20, 2014.
U. S. P.T. O. Notice of Allowance for U.S. Appl. No. 11/134,055, mailed Feb. 19, 2014.
U. S. P.T. O. Notice of Allowance for U.S. Appl. No. 11/134,055, mailed May 5, 2014.
E.P.O. Notice of Intent to Grant for European Application No. 07 758 171.8 mailed on Feb. 26, 2013.
U. S. P.T. O. Final Office Action for U.S. Appl. No. 11/371,376, mailed Oct. 16, 2012.
U. S. P. T. O. Notice of Allowance for U.S. Appl. No. 11/655,724, mailed Oct. 4, 2012.
U. S. P.T. O. Non-Final Office Action for U.S. Appl. No. 11/134,055, mailed Nov. 8, 2012.
E.P.O. Communication Pursuant to Article 94(3) for European Application No. 07 758 171.8-2310 mailed on Oct. 11, 2012.
J.P. Final Decision of Rejection for Japanese Application No. 2008-558536 considered by Examiner on Sep. 4, 2012.
U. S. Patent and Trademark Office "Communication" for U.S. Appl. No. 11/371,190, mailed Nov. 7, 2008.
U. S. Patent and Trademark Office "Communication" for U.S. Appl. No. 11/371,190, mailed Oct. 29, 2009.
U. S. Patent and Trademark Office "Communication" for U.S. Appl. No. 11/371,170, mailed Nov. 4, 2009.
U. S. Patent and Trademark Office "Communication" for U.S. Appl. No. 10/777,411, mailed Oct. 1, 2009.
U. S. Patent and Trademark Office "Communication" for U.S. Appl. No. 11/371,376, mailed Nov. 4, 2009.
U. S. Patent and Trademark Office "Communication" for U.S. Appl. No. 11/655,724, mailed Nov. 23, 2009.
U. S. Patent and Trademark Office "Communication" for U.S. Appl. No. 11/655,787, mailed Nov. 23, 2009.
U. S. Patent and Trademark Office "Communication" for U.S. Appl. No. 11/655,737, mailed Nov. 23, 2009.
U. S. Patent and Trademark Office "Communication" for U.S. Appl. No. 11/655,723, mailed Nov. 24, 2009.
U. S. Patent and Trademark Office "Communication" for U.S. Appl. No. 11/371,328, mailed Dec. 30, 2009.
U. S. Patent and Trademark Office "Communication" for U.S. Appl. No. 11/134,069, mailed Dec. 30, 2009.
U. S. Patent and Trademark Office "Communication" for U.S. Appl. No. 11/134,055, mailed Jan. 19, 2010.
U. S. Patent and Trademark Office "Communication" for U.S. Appl. No. 11/134,073, mailed Jan. 27, 2010.
U. S. Patent and Trademark Office "Communication" for U.S. Appl. No. 11/134,091, mailed Jan. 26, 2010.
U. S. Patent and Trademark Office "Communication" for U.S. Appl. No. 11/371,182, mailed Feb. 8, 2010.
U. S. Patent and Trademark Office "Communication" for U.S. Appl. No. 11/134,066, mailed Feb. 18, 2010.
U. S. Patent and Trademark Office "Communication" for U.S. Appl. No. 11/134,079, mailed Feb. 19, 2010.
U. S. Patent and Trademark Office "Communication" for U.S. Appl. No. 11/134,067, mailed Feb. 18, 2010.
U. S. Patent and Trademark Office "Communication" for U.S. Appl. No. 10/777,411, mailed Mar. 5, 2010.
U. S. Patent and Trademark Office "Communication" for U.S. Appl. No. 11/050,632, mailed Mar. 2, 2010.
U. S. Patent and Trademark Office "Communication" for U.S. Appl. No. 11/371,190, mailed Feb. 26, 2010.
U. S. Patent and Trademark Office "Communication" for U.S. Appl. No. 11/134,082, mailed Mar. 12, 2010.
U. S. Patent and Trademark Office "Communication" for U.S. Appl. No. 11/655,790, mailed Mar. 15, 2010.
U. S. Patent and Trademark Office "Communication" for U.S. Appl. No. 11/134,069, mailed Apr. 19, 2010.
U. S. Patent and Trademark Office "Communication" for U.S. Appl. No. 11/371,188, mailed Apr. 28, 2010.
U. S. Patent and Trademark Office "Communication" for U.S. Appl. No. 11/371,170, mailed May 4, 2010.
U. S. Patent and Trademark Office "Communication" for U.S. Appl. No. 11/371,376, mailed May 26, 2010.
U. S. Patent and Trademark Office "Communication" for U.S. Appl. No. 11/526,849, mailed Jun. 1, 2010.
U. S. Patent and Trademark Office "Communication" for U.S. Appl. No. 11/134,082, mailed May 25, 2010.
U. S. Patent and Trademark Office "Communication" for U.S. Appl. No. 10/777,411, mailed Jun. 9, 2010.
U. S. Patent and Trademark Office "Communication" for U.S. Appl. No. 11/371,328, mailed Jun. 17, 2010.
U. S. Patent and Trademark Office "Communication" for U.S. Appl. No. 11/371,188, mailed Jun. 15, 2010.
U. S. Patent and Trademark Office "Communication" for U.S. Appl. No. 11/371,182, mailed Jun. 8, 2010.
U. S. Patent and Trademark Office "Communication" for U.S. Appl. No. 11/371,376, mailed Jul. 29, 2010.
U. S. Patent and Trademark Office "Communication" for U.S. Appl. No. 11/371,190, mailed Aug. 11, 2010.
U. S. Patent and Trademark Office "Communication" for U.S. Appl. No. 11/134,091, mailed Aug. 4, 2010.
U. S. Patent and Trademark Office "Communication" for U.S. Appl. No. 11/975,916, mailed Aug. 4, 2010.
U. S. Patent and Trademark Office "Communication" for U.S. Appl. No. 11/975,917, mailed Aug. 17, 2010.
U. S. Patent and Trademark Office "Communication" for U.S. Appl. No. 11/975,919, mailed Aug. 19, 2010.

(56) References Cited

OTHER PUBLICATIONS

U. S. Patent and Trademark Office "Communication" for U.S. Appl. No. 11/371,182, mailed Aug. 25, 2010.
U. S. Patent and Trademark Office "Communication" for U.S. Appl. No. 11/371,188, mailed Sep. 1, 2010.
U. S. Patent and Trademark Office "Communication" for U.S. Appl. No. 10/777,411, mailed Oct. 15, 2010.
U. S. Patent and Trademark Office "Communication" for U.S. Appl. No. 11/371,170, mailed Jul. 12, 2010.
U. S. Patent and Trademark Office "Communication" for U.S. Appl. No. 11/526,849, mailed Dec. 6, 2010.
U. S. Patent and Trademark Office "Communication" for U.S. Appl. No. 11/371,328, mailed Jan. 6, 2011.
U. S. Patent and Trademark Office "Communication" for U.S. Appl. No. 11/371,170, mailed Jan. 28, 2011.
U. S. Patent and Trademark Office "Communication" for U.S. Appl. No. 11/975,916, mailed Feb. 9, 2011.
U. S. Patent and Trademark Office "Communication" for U.S. Appl. No. 11/975,917, mailed Feb. 4, 2011.
U. S. Patent and Trademark Office "Communication" for U.S. Appl. No. 11/975,919, mailed Feb. 4, 2011.
U. S. Patent and Trademark Office "Communication" for U.S. Appl. No. 11/526,849, mailed Feb. 23, 2011.
Co-pending U.S. Appl. No. 13/072,511 entitled "Interbody Device Insertion Systems and Methods" to Gimbel et al. filed Mar. 25, 2011.
U. S. Patent and Trademark Office "Communication" for U.S. Appl. No. 11/371,170, mailed May 6, 2011.
U. S. P.T. O. Non-Final Office Action for U.S. Appl. No. 11/975,920, mailed Jun. 7, 2011.
U. S. P.T. O. Non-Final Office Action for U.S. Appl. No. 11/975,921, mailed Jun. 9, 2011.
U. S. P.T. O. Non-Final Office Action for U.S. Appl. No. 11/134,055, mailed Jun. 9, 2011.
U. S. P.T. O. Notice of Allowance for U.S. Appl. No. 11/371,328, mailed Jun. 23, 2011.
U. S. P.T. O. Non-Final Office Action for U.S. Appl. No. 11/975,919, mailed Jul. 21, 2011.
U. S. P.T. O. Advisory Action for U.S. Appl. No. 11/371,170, mailed Aug. 5, 2011.
U. S. P.T. O. Notice of Allowance for U.S. Appl. No. 11/655,790, mailed Feb. 4, 2011.
U. S. P.T. O. Non-Final Office Action for U.S. Appl. No. 11/975,918, mailed Aug. 15, 2011.
U. S. P.T. O. Final Office Action for U.S. Appl. No. 11/975,916, mailed Sep. 6, 2011.
U. S. P.T. O. Non-Final Office Action for U.S. Appl. No. 11/975,917, mailed Aug. 3, 2011.
U. S. P.T. O. Non-Final Office Action for U.S. Appl. No. 11/134,091, mailed Aug. 12, 2011.
U. S. P.T. O. Notice of Allowance for U.S. Appl. No. 11/134,069, mailed Oct. 13, 2011.
U. S. P.T. O. Final Office Action for U.S. Appl. No. 11/134,055, mailed Nov. 14, 2011.
U. S. P.T. O. Non-Final Office Action for U.S. Appl. No. 12/841,792, mailed Oct. 20, 2011.
U. S. P.T. O. Notice of Allowance for U.S. Appl. No. 11/134,073, mailed Oct. 13, 2011.
U. S. P.T. O. Notice of Allowance for U.S. Appl. No. 11/134,079, mailed Nov. 25, 2011.
U. S. P.T. O. Notice of Allowance for U.S. Appl. No. 11/134,067, mailed Oct. 03, 2011.
U. S. P.T. O. Notice of Allowance for U.S. Appl. No. 11/371,170, mailed Oct. 12, 2011.
U. S. P.T. O. Notice of Allowance for U.S. Appl. No. 11/975,921, mailed Dec. 14, 2011.
U. S. P.T. O. Notice of Allowance for U.S. Appl. No. 11/975,920, mailed Nov. 16, 2011.
U. S. P.T. O. Non-Final Office Action for U.S. Appl. No. 11/655,723, mailed May 20, 2014.

Co-pending U.S. Appl. No. 14/185,561 entitled "Expandable Fusion Device for Positioning Between Adjacent Vertebral Bodies" to Wagner, filed Feb. 20, 2014.
U. S. P. T. O. Notice of Allowance for U.S. Appl. No. 11/655,787, mailed Sep. 26, 2014.
U. S. P.T. O. Final Office Action for U.S. Appl. No. 11/655,723, mailed Dec. 26, 2014.
U. S. P.T. O. Notice of Allowance for U. S. Appl. No. 13/784,224 mailed Sep. 18, 2014.
PCT Search Report and Written Opinion for PCT/US2004/025090 mailed on Apr. 11, 2005 (23 pages).
Humphreys et al., "Biomechanics of the KENTI (TM) Total Joint Replacement", Presented at the Global Symposium on Motion Preservation Technology, May 9-13, 2006; 3 pages.
Hodges et al., "Biomechanics of the KENTI (TM) Total Joint Replacement", Presented at the Global Symposium on Motion Preservation Technology, May 9-13, 2006; 1 page.
Patel et al., "Changes in Kinematics following Single Level fusion, Single and Bi-Level Charite disc replacement in the Lumbar Spine" Presented at the Global Symposium on Motion Preservation Technology, May 9-13, 2006; 1 page.
Serhan et al. "Biomechanics of the posterior lumbar articulating elements," Neurosurg Focus 2007, 22(1):E1, 6 pages.
Khoueir et al. "Classification of posterior dynamic stabilization devices," Neurosurg Focus, 2007, 22(1):E1, 8 pages.
PCT Search Report and Written Opinion for International Application No. PCT/US2007/063595 mailed Dec. 11, 2007, 15 pages.
International Preliminary Report on Patentability for International Application No. PCT/US2008/051346 mailed Mar. 27, 2009, 23 pages.
International Search Report and Written Opinion for International Application No. PCT/US2008/051346 mailed Sep. 9, 2008, 20 pages.
E.P.O. Decision to Grant for European Application No. 07 758 171.8 mailed on May 30, 2014.
U.S. Patent and Trademark Office "Communication" for U.S. Appl. No. 11/343,933 mailed Nov. 19, 2007.
U.S. Patent and Trademark Office "Communication" for U.S. Appl. No. 11/134,091 mailed Feb. 21, 2008.
U.S. Patent and Trademark Office "Communication" for U.S. Appl. No. 11/134,092 mailed Feb. 21, 2008.
U.S. Patent and Trademark Office "Communication" for U.S. Appl. No. 10/777,411 mailed Mar. 20, 2008.
U.S. Patent and Trademark Office "Communication" for U.S. Appl. No. 11/134,055 mailed Aug. 25, 2008.
U.S. Patent and Trademark Office "Communication" for U.S. Appl. No. 11/343,933 mailed Jun. 30, 2008.
U.S. Patent and Trademark Office "Communication" for U.S. Appl. No. 10/777,411 mailed Mar. 19, 2007.
U.S. Patent and Trademark Office "Communication" for U.S. Appl. No. 10/777,411 mailed Sep. 24, 2007.
U.S. Patent and Trademark Office "Communication" for U.S. Appl. No. 10/777,411 mailed Aug. 29, 2008.
U.S. Patent and Trademark Office "Communication" for U.S. Appl. No. 10/777,411 mailed Dec. 23, 2008.
U.S. Patent and Trademark Office "Communication" for U.S. Appl. No. 11/050,632 mailed Sep. 24, 2008.
U.S. Patent and Trademark Office "Communication" for U.S. Appl. No. 11/050,632 mailed Apr. 16, 2009.
U.S. Patent and Trademark Office "Communication" for U.S. Appl. No. 11/134,066 mailed Dec. 4, 2008.
U.S. Patent and Trademark Office "Communication" for U.S. Appl. No. 11/134,091 mailed Dec. 24, 2008.
U.S. Patent and Trademark Office "Communication" for U.S. Appl. No. 11/134,069 mailed Dec. 24, 2008.
U.S. Patent and Trademark Office "Communication" for U.S. Appl. No. 11/134,069 mailed Jun. 5, 2009.
U.S. Patent and Trademark Office "Communication" for U.S. Appl. No. 11/134,082 mailed Dec. 3, 2008.
U.S. Patent and Trademark Office "Communication" for U.S. Appl. No. 11/345,602 mailed Mar. 31, 2009.
U. S. Patent and Trademark Office "Communication" for U.S. Appl. No. 10/777,411, mailed Jul. 17, 2009.

(56) References Cited

OTHER PUBLICATIONS

U. S. Patent and Trademark Office "Communication" for U.S. Appl. No. 11/134,073, mailed Jul. 22, 2009.
U. S. Patent and Trademark Office "Communication" for U.S. Appl. No. 11/134,079, mailed Aug. 14, 2009.
U. S. Patent and Trademark Office "Communication" for U.S. Appl. No. 11/134,082, mailed Aug. 14, 2009.
U. S. Patent and Trademark Office "Communication" for U.S. Appl. No. 11/134,067, mailed Aug. 14, 2009.
U. S. Patent and Trademark Office "Communication" for U.S. Appl. No. 11/050,632, mailed Aug. 25, 2009.
U. S. Patent and Trademark Office "Communication" for U.S. Appl. No. 11/134,066, mailed Sep. 9, 2009.
U. S. Patent and Trademark Office "Communication" for U.S. Appl. No. 11/345,602, mailed Oct. 13, 2009.
U. S. Patent and Trademark Office "Communication" for U.S. Appl. No. 11/371,190, mailed Oct. 11, 2007.
U. S. Patent and Trademark Office "Communication" for U.S. Appl. No. 11/371,181, mailed Oct. 11, 2007.
U. S. Patent and Trademark Office "Communication" for U.S. Appl. No. 11/371,376, mailed Nov. 29, 2007.
U. S. Patent and Trademark Office "Communication" for U.S. Appl. No. 11/371,190, mailed Apr. 17, 2008.
U. S. Patent and Trademark Office "Communication" for U.S. Appl. No. 11/371,188, mailed Mar. 17, 2009.
U. S. Patent and Trademark Office "Communication" for U.S. Appl. No. 11/371,182, mailed Oct. 11, 2007.
U. S. Patent and Trademark Office "Communication" for U.S. Appl. No. 11/371,182, mailed Jun. 9, 2008.
U. S. Patent and Trademark Office "Communication" for U.S. Appl. No. 11/371,182, mailed Dec. 12, 2008.
U. S. Patent and Trademark Office "Communication" for U.S. Appl. No. 11/371,182, mailed Mar. 25, 2009.
U. S. Patent and Trademark Office "Communication" for U.S. Appl. No. 11/371,182, mailed Apr. 24, 2009.
U. S. Patent and Trademark Office "Communication" for U.S. Appl. No. 11/371,376, mailed Apr. 20, 2009.
U. S. Patent and Trademark Office "Communication" for U.S. Appl. No. 11/371,328, mailed Mar. 17, 2009.
U. S. Patent and Trademark Office "Communication" for U.S. Appl. No. 11/371,190, mailed Aug. 11, 2008.
U. S. Patent and Trademark Office "Communication" for U.S. Appl. No. 11/655,724, mailed May 27, 2009.
U. S. Patent and Trademark Office "Communication" for U.S. Appl. No. 11/655,787, mailed May 27, 2009.
U. S. Patent and Trademark Office "Communication" for U.S. Appl. No. 11/655,737, mailed May 27, 2009.
U. S. Patent and Trademark Office "Communication" for U.S. Appl. No. 11/655,723, mailed May 27, 2009.
U. S. Patent and Trademark Office "Communication" for U.S. Appl. No. 11/655,790, mailed Jun. 4, 2009.
U. S. Patent and Trademark Office "Communication" for U.S. Appl. No. 11/371,182, mailed Jul. 21, 2009.
U. S. Patent and Trademark Office "Communication" for U.S. Appl. No. 11/371,376, mailed Aug. 28, 2009.
U. S. Patent and Trademark Office "Communication" for U.S. Appl. No. 11/371,328, mailed Sep. 28, 2009.
U. S. Patent and Trademark Office "Communication" for U.S. Appl. No. 11/371,188, mailed Sep. 25, 2009.
U. S. Patent and Trademark Office "Communication" for U.S. Appl. No. 11/371,190, mailed Apr. 29, 2009.
U. S. Patent and Trademark Office "Communication" for U.S. Appl. No. 11/371,182, mailed Oct. 14, 2009.
Petition for Inter Partes Review of U.S. Pat. No. 7,204,853 filed Aug. 17, 2015. Petitioner: *Globus Medical, Inc.* v. Patent Owner: *Flexuspine, Inc.* Case IPR2015-01749.
Case IPR2015-01749. EX1013: Blumenthal SL, Ohnmeiss DD. Intervertebral cages for degenerative spinal diseases. Spine J. Jul.-Aug. 2003;3(4):301-309.
Case IPR2015-01749. EX1014: Dooris AP, Goel VK, Grosland NM, Gilbertson LG, Wilder DG. Load-sharing between anterior and posterior elements in a lumbar motion segment implanted with an artificial disc. Spine (Phila Pa 1976). 2001;26(6):E122-129.
Case IPR2015-01749. EX1015: Mayer HM, Wiechert K, Korge A, Qose I. Minimally invasive total disc replacement: surgical technique and preliminary clinical results. Eur Spine J. Oct. 2002;11 Supp12:S124-30.
Case IPR2015-01749. EX1016: Foley KT, Holly LT, Schwender JD. Minimally invasive lumbar fusion. Spine (Phila Pa 1976). Aug. 1, 2003;28(15 Suppl):S26-35.
Case IPR2015-01749. EX1017: Tropiano P, Huang RC, Girardi FP, Mamay T. Lumbar disc replacement: preliminary results with ProDisc II after a minimum follow-up period of 1 year. J Spinal Disord Tech. Aug. 2003;16(4):362-8.
Case IPR2015-01749. EX1018: Folman Y, Lee S-H, Silvera JR, Gepstein R. Posterior Lumbar Interbody Fusion for Degenerative Disc Disease Using a Minimally Invasive B-Twin Expandable Spinal Spacer: a multicenter study. J Spinal Disord Tech .. 2003; 16(5):455-460.
Case IPR2015-01749. EX1019: Wagner PC, Bagby GW, Grant BD, Gallina A, Ratzlaff M, SandeR. Surgical stabilization of the equine cervical spine. Vet Surg 1979 8:7-12.
Case IPR2015-01749. EX1020: Weiner BK, Fraser RD. Spine update lumbar interbody cages. Spine. Mar. 1, 1998; 23(5):634-40.
Case IPR2015-01749. EX1021: Zeegers WS, Bohnen LM, Laaper M, Verhaegen MJ. Artificial disc replacement with the modular type SB Charite III: 2-year results in 50 prospectively studied patients. Eur Spine J. 1999;8(3):210-217.
Petition for Inter Partes Review of U.S. Pat. No. 7,316,714 filed Aug. 14, 2015. Petitioner: *Globus Medical, Inc.* v. Patent Owner: *Flexuspine, Inc.* Case IPR2015-01721.
Petition for Inter Partes Review of U.S. Pat. No. 7,909,869 filed Aug. 18, 2015. Petitioner: *Globus Medical, Inc.* v. Patent Owner: *Flexuspine, Inc.* Case IPR2015-01755.
Petition for Inter Partes Review of U.S. Pat. No. 8,647,386 filed Aug. 24, 2015. Petitioner: *Globus Medical, Inc.* v. Patent Owner: *Flexuspine, Inc.* Case IPR2015-01795.
Petition for Inter Partes Review of U.S. Pat. No. 8,123,810 filed Aug. 27, 2015. Petitioner: *Globus Medical, Inc.* v. Patent Owner: *Flexuspine, Inc.* Case IPR2015-01830.
U. S. P.T. O. Non-Final Office Action for U.S. Appl. No. 14/185,561, mailed May 5, 2015.
U. S. P.T. O. Notice of Allowance for U.S. Appl. No. 11/655,723, mailed Dec. 26, 2014.

\* cited by examiner

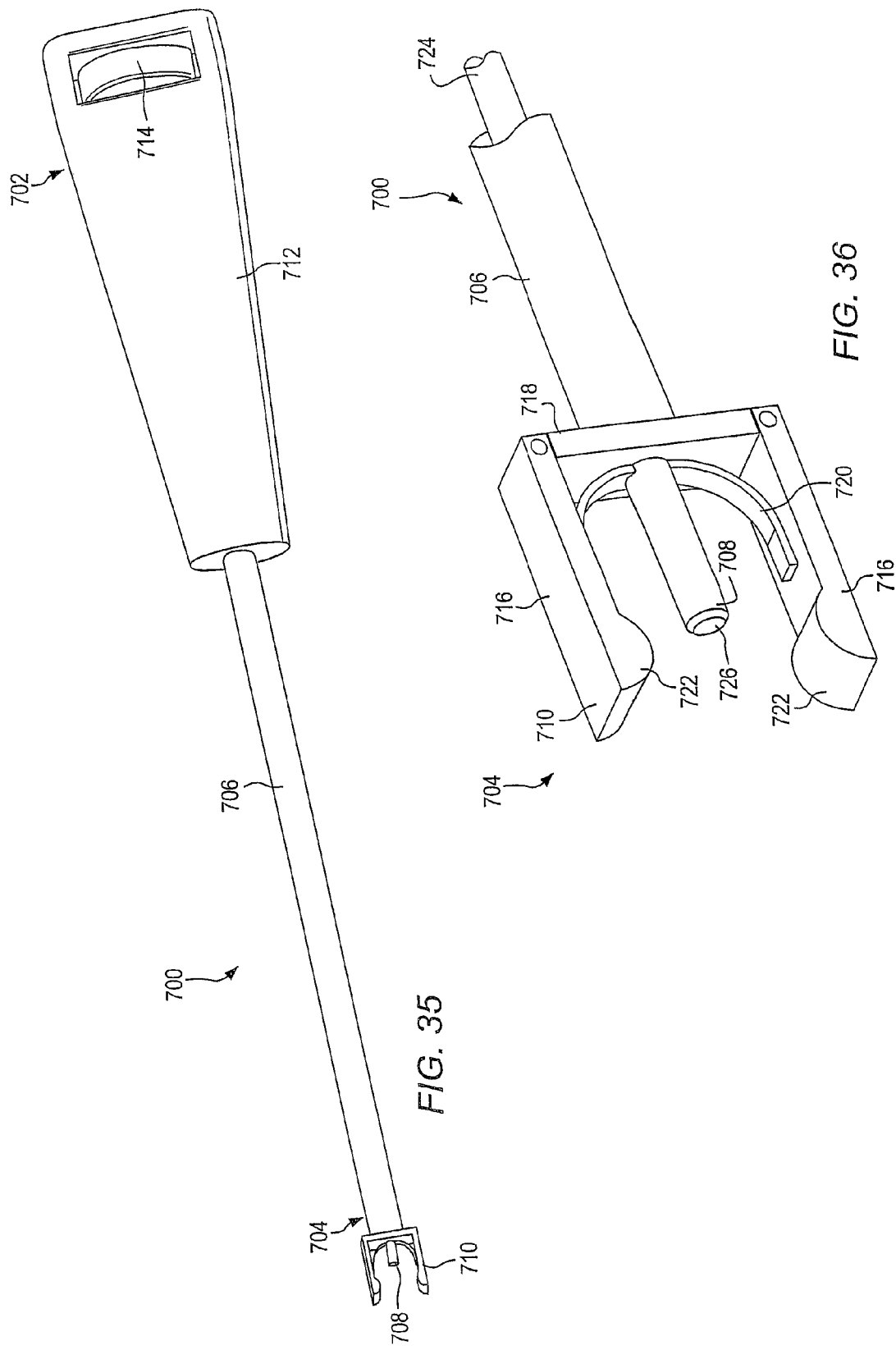

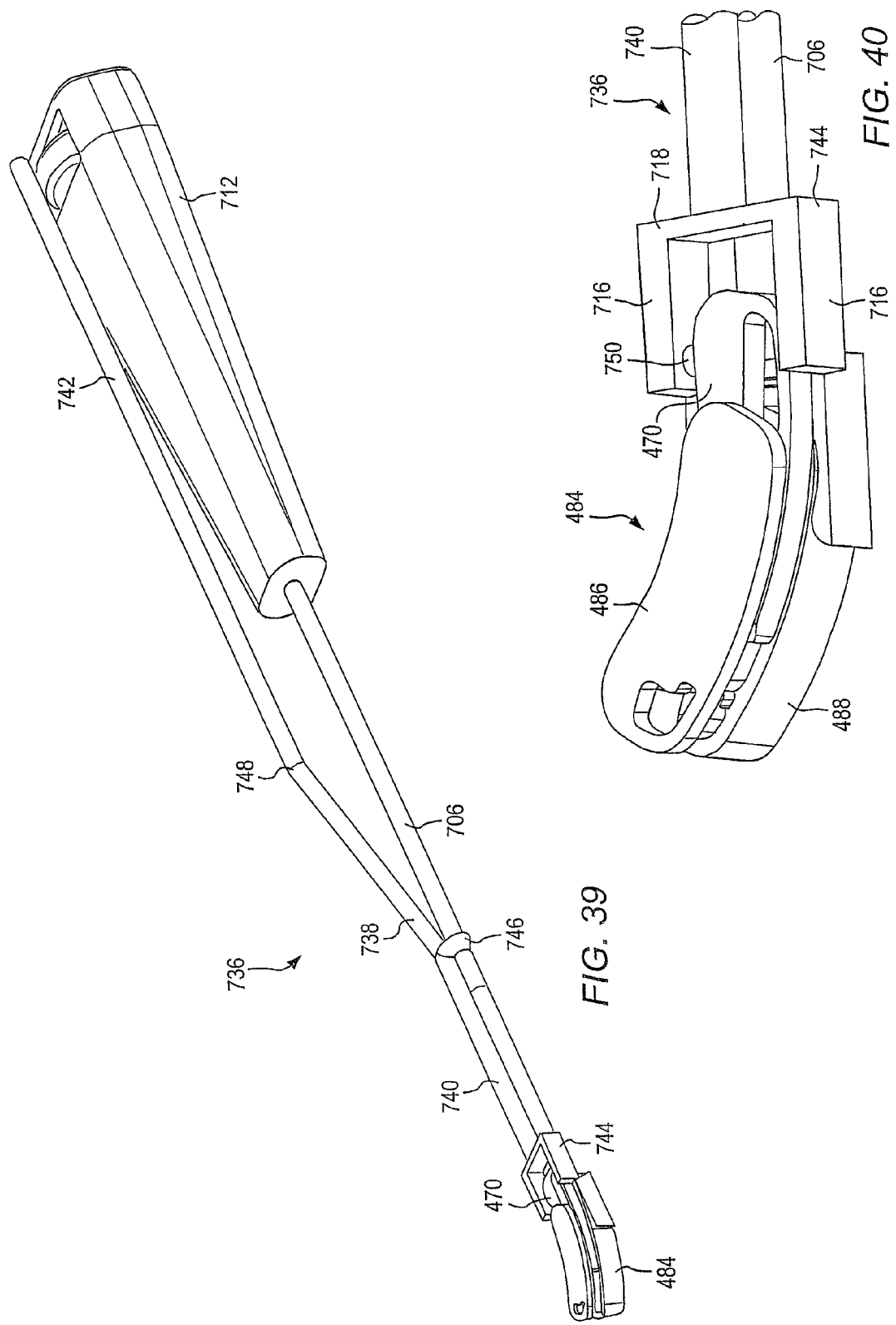

EXPANDABLE ARTICULATING INTERVERTEBRAL IMPLANT WITH LIMITED ARTICULATION

PRIORITY

This application is a continuation of U.S. Pat. No. 8,147,550 entitled "Expandable Articulating Intervertebral Implant with Limited Articulation" filed May 20, 2005 which is a continuation of U.S. Pat. No. 7,753,958 entitled "Functional Spinal Units" to Charles R. Gordon, Corey T. Harbold, and Heather S. Hanson, issued on Jul. 13, 2010 which is a continuation-in-part of PCT Application No. US2004/025090 entitled "Artificial Spinal Unit Assemblies" to Charles Gordon and Corey Harbold, filed on Aug. 4, 2004 which is a continuation-in-part of U.S. Pat. No. 7,909,869 entitled "Artificial Spinal Unit Assemblies" to Charles Gordon and Corey Harbold, issued on Mar. 22, 2011 which is a continuation-in-part of U.S. Pat. No. 7,316,714 entitled "Artificial Functional Spinal Unit Assemblies" to Charles Gordon and Corey Harbold, issued on Jan. 8, 2008, which is a continuation-in-part of U.S. Pat. No. 7,204,853 entitled "Artificial Functional Spinal Unit Assemblies" to Charles Gordon and Corey Harbold issued on Apr. 17, 2007.

BACKGROUND

1. Field of the Invention

Embodiments of the invention generally relate to functional spinal implant assemblies for insertion into an intervertebral space between adjacent vertebrae of a human spine, and reconstruction of the posterior elements to provide stability, flexibility, and proper biomechanical motion. More specifically, embodiments of the invention relate to artificial functional spinal units including an expandable artificial intervertebral implant that can be inserted via a posterior surgical approach and used in conjunction with one or more facet replacement devices to approach an anatomically correct range of motion. Embodiments of the invention may also be inserted via an anterior surgical approach.

2. Description of Related Art

The human spine is a complex mechanical structure including alternating bony vertebrae and fibrocartilaginous discs that are connected by strong ligaments and supported by musculature that extends from the skull to the pelvis and provides axial support to the body. The intervertebral discs provide mechanical cushion between adjacent vertebral segments of the spinal column and generally include three basic components: the nucleus pulposus, the annulus fibrosis, and two vertebral end plates. The end plates are made of thin cartilage overlying a thin layer of hard cortical bone that attaches to the spongy, cancellous bone of the vertebral body. The annulus fibrosis forms the disc's perimeter and is a tough outer ring that binds adjacent vertebrae together. The vertebrae generally include a vertebral foramen bounded by the anterior vertebral body and the neural arch, which consists of two pedicles and two laminae that are united posteriorly. The spinous and transverse processes protrude from the neural arch. The superior and inferior articular facets lie at the root of the transverse process.

The human spine is a highly flexible structure capable of a high degree of curvature and twist in nearly every direction. However, genetic or developmental irregularities, trauma, chronic stress, and degenerative wear can result in spinal pathologies for which surgical intervention may be necessary. In cases of deterioration, disease, or injury, a spinal disc may be removed from a human spine. A disc may become damaged or diseased, reducing intervertebral separation. Reduction of the intervertebral separation may reduce a height of the disc nucleus, which may cause the annulus to buckle in areas where the laminated plies are loosely bonded. As the overlapping laminated plies of the annulus begin to buckle and separate, circumferential or radial annular tears may occur. Such disruption to the natural intervertebral separation may produce pain, which may be alleviated by removal of the disc and maintenance of the natural separation distance. In cases of chronic back pain resulting from a degenerated or herniated disc, removal of the disc becomes medically necessary.

In some cases, a damaged disc may be replaced with a disc prosthesis intended to duplicate the function of a natural spinal disc. U.S. Pat. No. 4,863,477 to Monson, which is incorporated herein by reference, discloses a resilient spinal disc prosthesis intended to replace the resilience of a natural human spinal disc. U.S. Pat. No. 5,192,326 to Bao et al., which is incorporated herein by reference, describes a prosthetic nucleus for replacing just the nucleus portion of a human spinal disc. U.S. Patent Application Publication No. 2005/0021144 to Malberg et al., which is incorporated herein by reference, describes an expandable spinal implant.

In other cases, it may be desirable to fuse adjacent vertebrae of a human spine together after removal of a disc. This procedure is generally referred to as "intervertebral fusion" or "interbody fusion." Intervertebral fusion has been accomplished with a variety of techniques and instruments. It is generally known that the strongest intervertebral fusion is the interbody fusion (between the lumbar bodies), which may be augmented by a posterior or facet fusion. In cases of intervertebral fusion, either structural bone or an interbody fusion cage filled with bone graft material (e.g., morselized bone) is placed within the space where the spinal disc once resided. Multiple cages or bony grafts may be used within that space.

Cages of the prior art have been generally successful in promoting fusion and approximating proper disc height. Cages inserted from the posterior approach, however, are limited in size by the interval between the nerve roots. Therefore, a fusion implant assembly that could be expanded from within the intervertebral space could reduce potential trauma to the nerve roots and yet still allow restoration of disc space height. It should be noted, however, that fusion limits overall flexibility of the spinal column and artificially constrains the natural motion of the patient. This constraint may cause collateral injury to the patient's spine as additional stresses of motion, normally borne by the now-fused joint, are transferred onto the nearby facet joints and intervertebral discs. Thus, an implant assembly that mimics the biomechanical action of the natural disc cartilage, thereby permitting continued normal motion and stress distribution, would be advantageous.

A challenge of instrumenting a disc posteriorly is that a device large enough to contact the end plates and slightly expand the space must be inserted through a limited space. This challenge is often further heightened by the presence of posterior osteophytes, which may cause "fish mouthing" of the posterior end plates and result in very limited access to the disc. A further challenge in degenerative disc spaces is the tendency of the disc space to assume a lenticular shape, which requires a relatively larger implant than often is easily introduced without causing trauma to the nerve roots. The size of rigid devices that may safely be introduced into the disc space is thereby limited.

The anterior approach poses significant challenges as well. Though the surgeon may gain very wide access to the interbody space from the anterior approach, this approach has its own set of complications. The retroperitoneal approach usually requires the assistance of a surgeon skilled in dealing with the visceral contents and the great vessels, and the spine surgeon has extremely limited access to the nerve roots. Complications of the anterior approach that are approach-specific include retrograde ejaculation, ureteral injury, and great vessel injury. Injury to the great vessels may result in massive blood loss, postoperative venous stasis, limb loss, and intraoperative death. The anterior approach is more difficult in patients with significant obesity and may be virtually impossible in the face of previous retroperitoneal surgery.

Despite its difficulties, the anterior approach does allow for the wide exposure needed to place a large device. In accessing the spine anteriorly, one of the major structural ligaments, the anterior longitudinal ligament, must be completely divided. A large amount of anterior annulus must also be removed along with the entire nucleus. Once these structures have been resected, the vertebral bodies are over distracted in order to place the device within the disc and restore disc space height. Failure to adequately tension the posterior annulus and ligaments increases the risk of device failure and migration. Yet in the process of placing these devices, the ligaments are overstretched while the devices are forced into the disc space under tension. This over distraction can damage the ligaments and the nerve roots. The anterior disc replacement devices currently available or in clinical trials may be too large to be placed posteriorly, and may require over distraction during insertion in order to allow the ligaments to hold them in position.

SUMMARY

In an embodiment, an intervertebral implant may include first and second members having outer surfaces that engage vertebrae of a human spine. The implant may include an insert positioned between inner surfaces of the first and second members before insertion of the implant between the vertebrae. The implant may include an expansion member that increases a separation distance between the first member and the second member. A portion of the expansion member may engage the insert to increase a range of angular motion between the first and second members after insertion of the implant between the vertebrae. In one embodiment, the insert includes a convex spherical surface that contacts the inner surface of the first or second member. In another embodiment, the insert includes a convex ellipsoidal surface that contacts the inner surface of the first or second member.

In an embodiment, an insert for an intervertebral implant may be rotatable. The insert may include protrusions, such as radial arms. In certain embodiments, the protrusions may be generally aligned along a longitudinal axis of the implant. The implant may further include an expansion member that engages at least one of the protrusions to rotate the insert. Rotation of the insert may increase a height of the implant. In some embodiments, an implant may provide for a functional spinal unit (e.g., an implant having a first member that articulates relative to a second member). In other embodiments, an implant may provide for fusion of the vertebrae.

In some embodiments, the insert may have an inclined surface that engages the first or second member. In one embodiment, the insert includes a plurality of cam ramps. In certain embodiments, the insert may comprise platforms. Engagement of the platforms with the first or second member may maintain the implant at an increased height. In other embodiments, one or both of the first and second members may include an inclined surface that engages a portion of an insert. In some embodiments, the inclined portions are angled such that an anterior height of the implant differs from a posterior height of the implant after rotation of the insert.

In an embodiment, an implant may include a spacer that is inserted between the first and second members. The spacer may maintain the implant at a desired height. In some embodiments, the spacer may include a lip that facilitates insertion (e.g., guides the spacer into position in the implant). In certain embodiments, the spacer may include a protrusion that engages a portion of the implant to provide a tactile sensation when the spacer is fully installed.

An implant may include aligning elements to maintain alignment of a first member and a second member during use. In certain embodiments, an implant may include stabilizers coupled to a first member that engage a second member to inhibit separation of the first member from the second member. In certain embodiments, the stabilizers may be angled with respect to a top surface of the first member.

In an embodiment, an implant may include a rotating insert whose axis of rotation is generally aligned along a longitudinal axis of the implant. The insert may include a spiral cam. In one embodiment, the spiral cam is lockable to maintain an expanded height of the implant.

In an embodiment, a facet replacement device may include two or more pedicle screws and an elongated member. The elongated member may include retaining portions that inhibit translation of at least one end of the rod during use. In certain embodiments, the retaining portions may include rings placed over the elongated member. In one embodiment, the elongated member includes a reduced diameter portion at a junction between the elongated member and a pedicle screw. The retaining portions may allow a limited range of translation and/or angulation of the elongated member with respect to the pedicle screws.

In some embodiments, resilient members may be provided between retaining portions on an elongated member and pedicle screws. The resilient members may cushion engagement between the retaining portions and the screws. In one embodiment, the resilient members are O-rings that partially reside in a head of a pedicle screw.

In another embodiment, a facet replacement device may include pedicle screws having head posts and an elongated member having apertures for receiving the posts. The apertures may allow a limited range of motion of the pedicle screws relative to the elongated member. In one embodiment, the elongated member may be a flat plate. In another embodiment, the elongated member may have a T-shaped cross section. In certain embodiments, resilient members may be provided in the apertures to cushion engagement between the elongated member and the screws.

In an embodiment, a surgical instrument may include a shaft and a driver rotatably coupled to the shaft. The driver may engage an insert of the implant while the implant is between two vertebrae of a human spine. The driver may be operable to actuate the insert to spread two or more endplate engaging members of the implant apart while the implant is between the vertebrae. The driver may be operated using a thumbwheel or similar device. In certain embodiments, the instrument may include a protector that protects portions of the driver and/or the thumbwheel from damage during use.

In some embodiments, an instrument may include an inserter that can be movably coupled to a shaft for an implant holder or expansion driver. The inserter may be used to insert a spacer between endplate engaging members of the implant. Engagement of the inserter on the shaft may guide the spacer to a desired location for insertion between the endplate engaging members.

In an embodiment, a holding device may be used to hold an implant or a spacer. The holding device may include a pair of opposing holding arms that engage surfaces of the implant or spacer. In some embodiments, a holding device may inhibit movement of an implant while a driver is actuated to expand the implant. In certain embodiments, a holding device may be operated using a control member, such as a thumbwheel or lever. In one embodiment, a holding device may include a shape memory alloy portion that allows release of the holding device when the device reaches a certain temperature. In another embodiment, an instrument may include a slide that is selectively positioned to inhibit release of the holding device.

In an embodiment, a method of performing a minimally invasive surgical procedure may include removing a portion of a disc between two vertebrae of a human spine, placing an implant in a disc space between the vertebrae using a posterior approach, spreading end plate engaging members of the implant in the disc space until the implant reaches an expanded height, and fixing the height of the implant at the expanded height. The maximum disc space height between the vertebrae at any time during the procedure may be less than or equal to the expanded height of the implant. In some embodiments, fixing the height of the implant may include inserting one or more spacers between the end plate engaging members.

BRIEF DESCRIPTION OF THE DRAWINGS

Advantages of the present invention will become apparent to those skilled in the art with the benefit of the following detailed description and upon reference to the accompanying drawings in which:

FIG. 35 is a perspective view of an instrument for installing and expanding an implant.

FIG. 36 is a detail view of a distal end of an instrument for installing and expanding an implant.

FIG. 39 is a perspective view of an instrument for installing an expandable implant including a spacer.

FIG. 40 is a perspective top view of an expandable implant held by an instrument with a partially inserted spacer.

Figure 1:
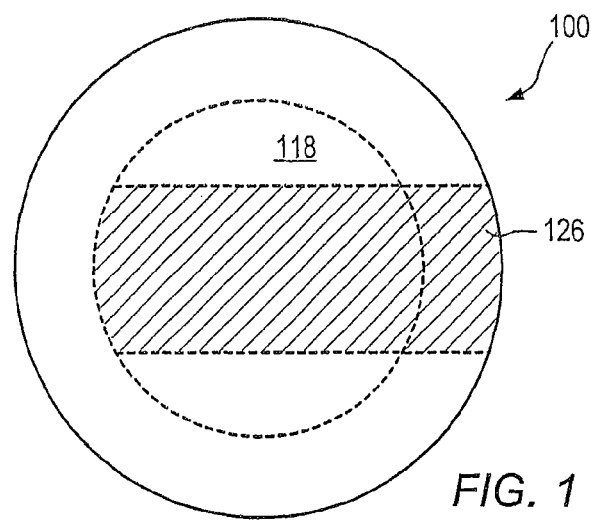
FIG. 1 depicts a top view of an embodiment of a cylindrical, expandable implant.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION

As used herein, "implant" generally refers to an artificial intervertebral implant or cage. The shape and/or size of an implant or other device disclosed herein may be chosen according to factors including, but not limited to, the surgical approach employed for insertion (e.g., anterior or posterior), the intended position in the spine (e.g., cervical or lumbar), and a size of the patient. For example, cervical implants may range from about 6 mm to about 11 mm in height, and lumbar implants may range from about 10 mm to about 18 mm in height. Heights outside these ranges may be used as required by a patient's anatomy. In general, implants with a substantially round cross section may range from about 14 mm to about 26 mm in diameter, and implants with a substantially square cross section may range from a size of about 14 mm square to a size of about 26 mm square. Implants that are substantially rectangular or trapezoidal may range from about 8 mm to about 12 mm along short side of the implant to about 24 mm to about 30 mm along a long side of the implant. As used herein, "c-shaped" implants generally refer to implants with an arcuate shape. Some c-shaped implants may be slightly curved (e.g., "banana-shaped"), while other c-shaped implants may have a higher degree of curvature (e.g., more closely approximating a "c").

It is to be understood that implants described herein may include features not necessarily depicted in each figure. In some embodiments, an endplate engaging surface of any implant may have regularly or irregularly spaced protrusions of uniform or various shapes and sizes to facilitate retention of the implant in a desired position between vertebrae. For example, an endplate engaging surface of an implant may include teeth or ridges. In some embodiments, members of an implant may include one or more openings to accommodate packing of bone graft material and/or to allow for bone ingrowth. In certain embodiments, one or more surfaces of an implant may include material, such as osteoconductive scaffolding, to enhance integration of the implant in a patient's spine. In some embodiments, a substance to be delivered to a patient's body may be included in a portion of the implant for delivery to the insertion site. In certain embodiments, implants depicted herein may include features allowing the implant to provide a desired lordotic angle (e.g., up to about 15°) between vertebrae.

As used herein, an "expandable" implant generally refers to an implant designed such that a height of the implant and/or a separation distance between two parts of the implant may be increased. In some embodiments, an implant may be expanded after insertion of the implant in a human spine. In certain embodiments, a height of an implant may be decreased after the implant has been expanded during insertion in a human spine. In other embodiments, expansion of an implant may be substantially irreversible after insertion in a human spine.

As used herein, an "articulating" implant generally refers to an implant designed such that at least two members of the implant are capable of undergoing rotational motion with respect to each other in at least one direction after insertion in a human spine. In some embodiments, one or more members of an articulating implant may be capable of rotating in more than one direction with respect one or more other members of the implant after insertion in a human spine to allow, for example, anterior-posterior rotation and/or lateral bending. In some embodiments, rotation may occur about fixed axes. In certain embodiments, an axis of rotation may change as one member of an implant rotates relative to another member of the implant. In some embodiments, one or more members of an articulating implant may be capable of translating with respect to one or more other members of the implant. As used herein, an articulating implant may also be described as "functional" or "dynamic".

Implant embodiments depicted herein may be expandable and/or articulating. In certain embodiments, expansion of an implant after insertion in a human spine may allow articulation of the implant. That is, the implant may not display articulating motion before expansion of the implant in a human spine. In other embodiments, expansion of an implant after insertion in a human spine may allow an increased range of motion (increased articulation) between at least two members of the implant. As used herein, "insertion" of an implant in a human spine may refer to assembly, insertion, positioning, and/or expansion of the implant.

As used herein "facet replacement device" generally refers to a facet replacement device. For simplicity, a portion of a facet replacement device may generally be referred to as a facet replacement device. The facet replacement devices disclosed herein generally allow for rotational and/or translational motion of one or more portions of the facet replacement device including, but not limited to, a plate or elongated member (e.g., rod, bar, rail). Pedicle screws of facet replacement devices disclosed herein may retain multi-axial character after insertion of the facet replacement device. As used herein, "pedicle screw" refers to a portion of a facet replacement device that couples to bone. As used herein, "pedicle screw head" refers to a portion of a facet replacement device that accepts an elongated member. As used herein, "pedicle screw" and "pedicle screw head" may be separate components that may be assembled for use in a facet replacement device.

As used herein, "coupled" includes a direct or indirect coupling unless expressly stated otherwise. For example, a control member may be directly coupled to a driver or indirectly coupled by way of an intermediate shaft. As used herein, "member" includes an individual member or a combination of two or more individual members. A "member" may be straight, curved, flexible, rigid, or a combination thereof. A member may have any of various regular and irregular forms including, but not limited to, a rod, a plate, a disk, a cylinder, a disk, or a bar.

An implant may be constructed of one or more biocompatible metals having a non-porous quality (e.g., titanium) and a smooth finish. In some embodiments, an implant may be constructed of ceramic and/or one or more other suitable biocompatible materials, such as biocompatible polymers. Biocompatible polymers include, but are not limited to, polyetheretherketone resin ("PEEK"). In certain embodiments, an implant may be constructed of a combination of one or more biocompatible metals and one or more ceramic and/or polymeric materials. For example, an implant may be constructed of a combination of biocompatible materials including titanium and PEEK.

Figure 2A:
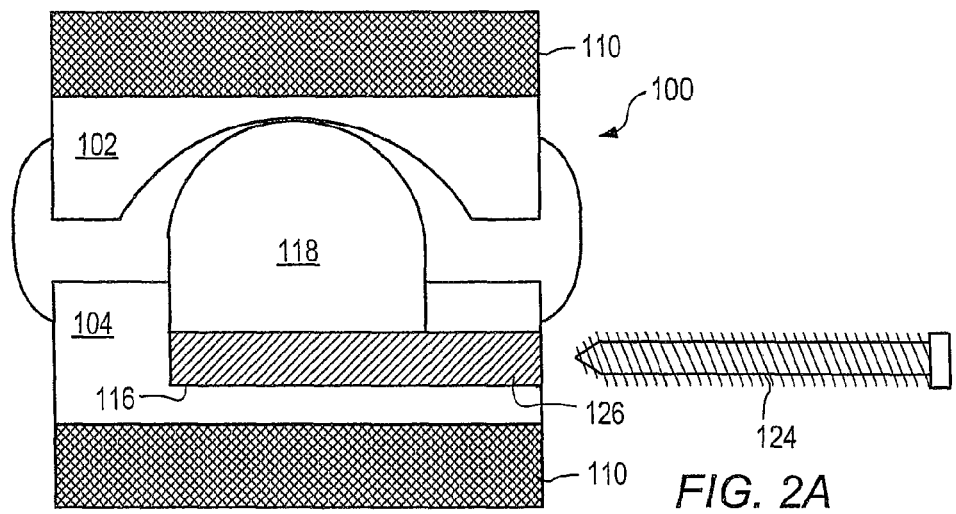
FIG. 2A is a side cross-sectional view of the embodiment depicted in FIG. 1.
Figure 2B:
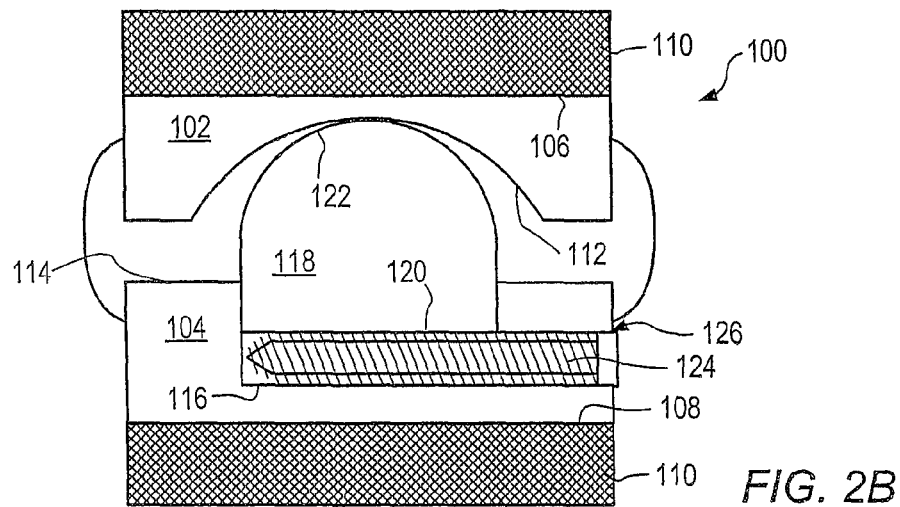
FIG. 2B is a side cross-sectional view of the implant embodiment depicted in FIG. 1.

FIG. 1 depicts a top view of an embodiment of an expandable, articulating implant. Implant 100 may be substantially cylindrical. FIGS. 2A and 2B depict a side cross-sectional view of implant 100. In some embodiments, implant 100 may include upper body 102 and lower body 104. As used herein, "body" may be of unitary construction or may include two or more members. References to "upper body" and "lower body" are chosen for convenience of description of the figures. In some embodiments, an implant may be inserted in a human spine with the "upper body" superior to the "lower body". In some embodiments, an implant may be inserted in a human spine with the "lower body" superior to the "upper body". In certain embodiments, upper and lower bodies of an implant may be substantially interchangeable. Similarly, "inferior" and "superior" surfaces are also named for convenience of description and may assume "superior" and "inferior" positions, respectively, upon insertion.

Implant 100 may include upper body 102 and lower body 104 in a substantially planar configuration. In some embodiments, superior surface 106 of upper body 102 and inferior surface 108 of lower body 104 may include (e.g., be coupled to) osteoconductive scaffolding 110 (e.g., an osteoconductive mesh structure). Vertebral bone from a patient's spine may grow through osteoconductive scaffolding 110 after insertion of implant 100. In some embodiments, osteoconductive scaffolding 110 may include spines and/or barbs that project into and secure against the bony endplates of the adjacent vertebral bodies upon expansion of the implant, reducing the possibility of subluxation and/or dislocation.

In some embodiments, a shape of recess 116 and insert 118 may be substantially the same as a shape of upper body 102 and/or lower body 104. In certain embodiments, a shape of insert 118 may be different from a shape of upper body 102 and/or lower body 104. For example, a shape of insert 118 may be oval or round, and upper body 102 and/or lower body 104 may be c-shaped. Implant 100 may include expansion member 124. Expansion member 124 may be inserted into opening 126 to elevate insert 118 from recess 116.

In some embodiments, at least a portion of inferior surface 112 of upper body 102 may be concave. In certain embodiments, superior surface 114 of lower body 104 may include recess 116. Recess 116 may include, but is not limited to, a channel or groove. In some embodiments, recess 116 may have a rectangular cross section that extends along lower body 104 in the medial-lateral direction. In certain embodiments, a shape of recess 116 may be substantially the same as a shape of upper body 102 and/or lower body 104. Insert 118 may be positioned in recess 116 on superior surface 114 of lower body 104. In some embodiments, inferior surface 120 of insert 118 may be substantially flat. In some embodiments, at least a portion of superior surface 122 of insert 118 may be convex. A convex portion of superior surface 122 of insert 118 may articulate with a concave portion of inferior surface 112 of upper body 102, allowing rotation of upper body 102 with respect to lower body 104.

In some embodiments, one or more expansion members may be used to increase a height of an implant and/or increase a separation distance between two or more members of an implant by engaging a portion (e.g., an insert) of the implant. In some embodiments, an expansion member may be a part of the implant. That is, the expansion member may remain coupled to the implant after insertion of the implant in a human spine. For example, expansion members may include, but are not limited to, screws, plates, wedges, and/or a combination of two or more of these elements. In some embodiments, an expansion member may be a tool, instrument, or driver that is used to expand the implant during insertion but does not remain as part of the implant following insertion. In certain embodiments, an expansion member may be used to elevate an insert with respect to the lower body of the implant, thereby increasing a height of the implant and/or increasing a separation distance between two or more members of the implant. In certain embodiments, an expansion member may be used to translate and/or rotate an insert with respect to a body of the implant (e.g., upper body, lower body), thereby increasing a height of the implant and/or increasing a separation distance between two or more members of the implant.

As depicted in FIGS. 2A and 2B, expansion member 124 may be a screw. Expansion member 124 may be inserted through opening 126 and below insert 118 to elevate the insert from lower body 104. In some embodiments, opening 126 may be threaded to accept a threaded expansion member. In certain embodiments, opening 126 may include features (e.g., notches) to allow stepwise insertion of an expansion member. For example, an expansion member may enter opening 126 in a ratcheting motion. In some embodiments, a void space may be created between insert 118 and the bottom of recess 116 adjacent to the expansion member.

Figure 3A:
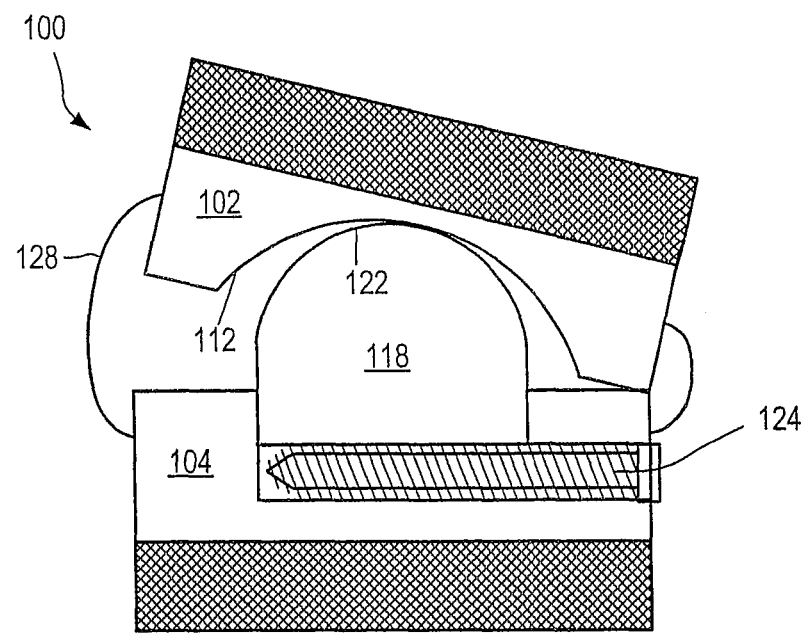
FIG. 3A is a cross-sectional view of an embodiment of an expandable implant in extension.
Figure 3B:
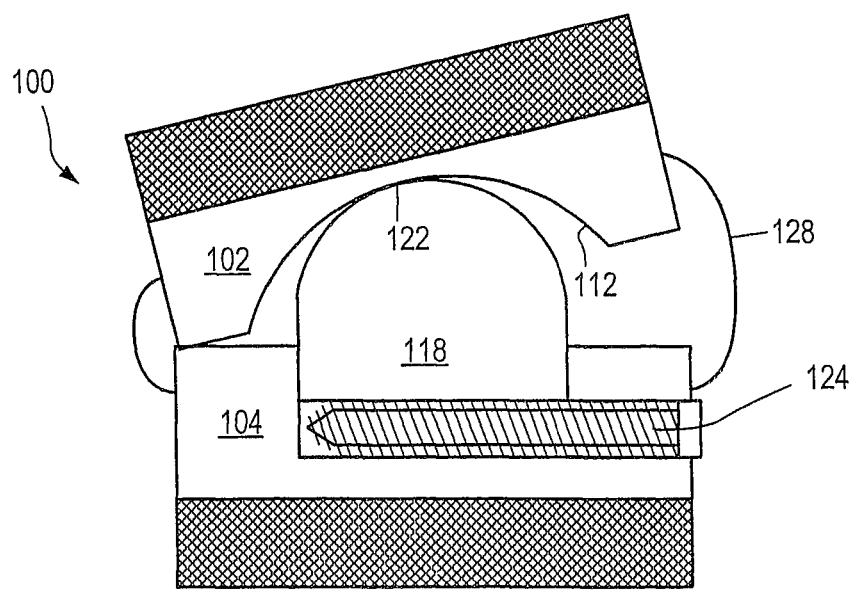
FIG. 3B is a cross-sectional view of an embodiment of an expandable implant in flexion.

FIGS. 3A and 3B depict side cross-sectional views of implant 100 after insertion of expansion member 124 (e.g., after expansion of the implant) such that concave inferior surface 112 of upper body 102 is able to articulate with convex superior surface 122 of insert 118. FIG. 3A depicts implant 100 with upper body 102 rotated with respect to lower body 104 to undergo extension. FIG. 3B depicts implant 100 with upper body 102 rotated with respect to lower body 104 to undergo flexion. In some embodiments, stabilizers 128 may be used to maintain alignment of upper body 102 and lower body 104 during insertion, expansion, and/or articulation of implant 100. Stabilizers 128 may include, but are not limited to, cables, retaining pegs, elastomeric bands, springs, and/or combinations thereof.

Figure 4A:
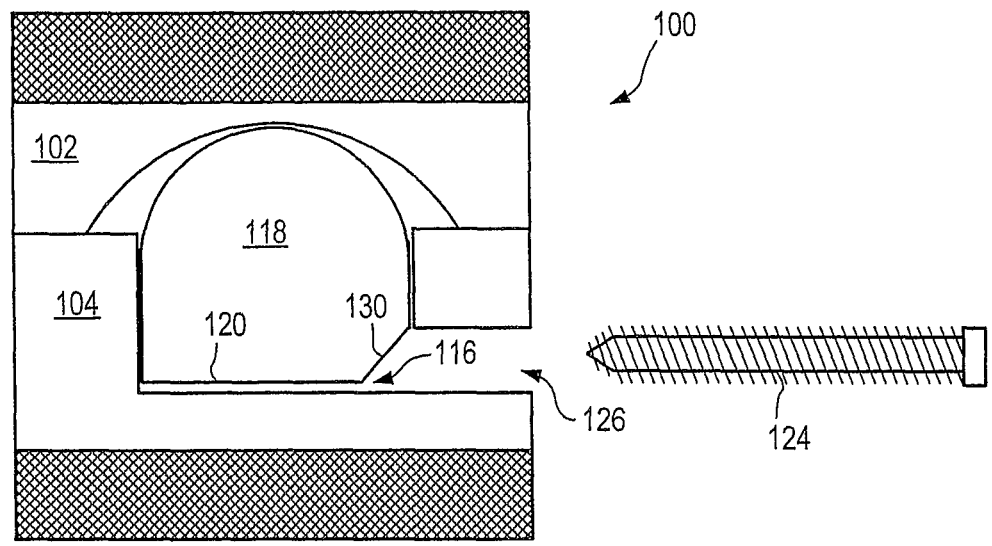
FIG. 4A is a cross-sectional view of an embodiment of an expandable implant prior to expansion.
Figure 4B:
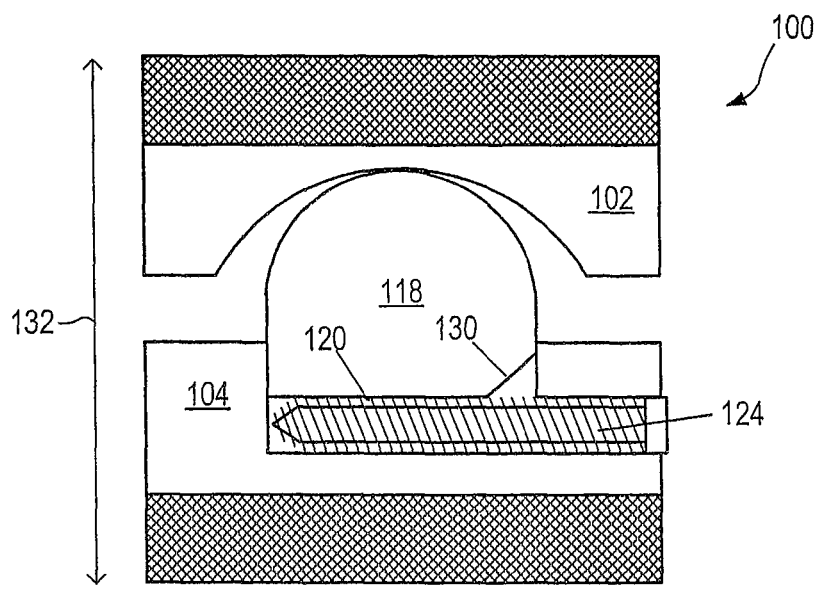
FIG. 4B is a cross-sectional view of an embodiment of an expandable implant following expansion.

FIGS. 4A and 4B illustrate the expansion of implant 100 in more detail. As shown in FIG. 4A, prior to expansion of implant 100, upper body 102 may rest upon lower body 104. Inferior surface 120 of insert 118 may rest upon the bottom of recess 116, which extends along a portion of lower body 104. In some embodiments, a surface of insert 118 may have angled portion 130. In some embodiments, an angled portion may be a wedge-shaped portion. In certain embodiments, an angled portion may include a curved surface or other surface to facilitate elevation of insert 118 from lower body 104. Angled portion 130 may facilitate the lifting of insert 118, allowing expansion member 124 to engage inferior surface 120 of insert 118. Following insertion of expansion member 124 (e.g., following expansion to a desired intervertebral disc height 132), inferior surface 120 of insert 118 may rest upon the expansion member with upper body 102 raised above lower body 104, as depicted in FIG. 4B.

Figure 4C:
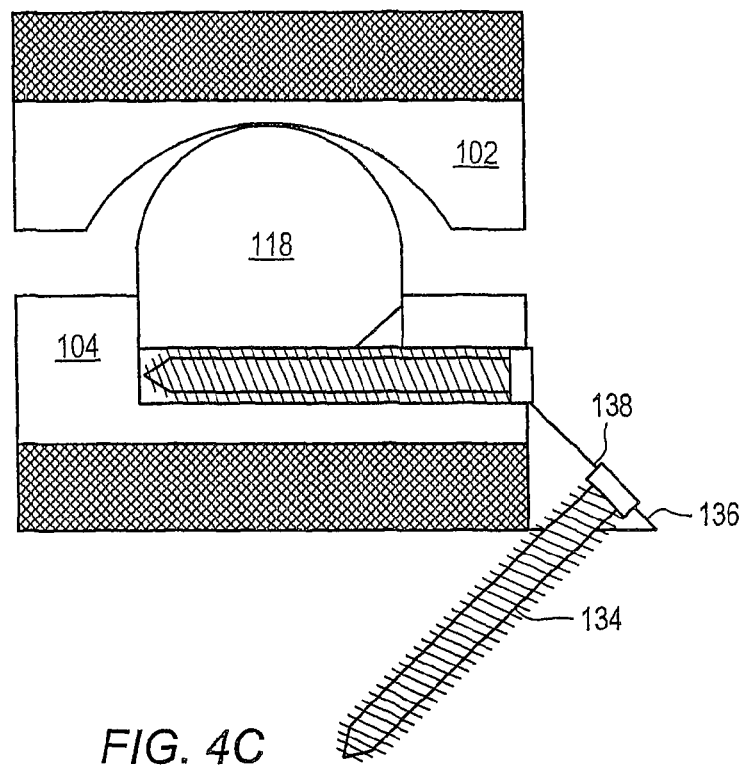
FIG. 4C is a cross-sectional view of an embodiment of an expandable implant employing buttress screws to secure the device between vertebrae.

After expansion of implant 100, the implant may be secured in place in a human spine with one or more fasteners (e.g., one or more buttress screws). FIG. 4C illustrates an embodiment utilizing fastener 134. Lower body 104 may include portion 136 with one or more openings 138 defined therethrough. One or more fasteners 134 may be inserted through portion 136 and secured into a vertebral body. In some embodiments, fastener 134 may be a screw (e.g., a buttress screw).

Figure 4D:
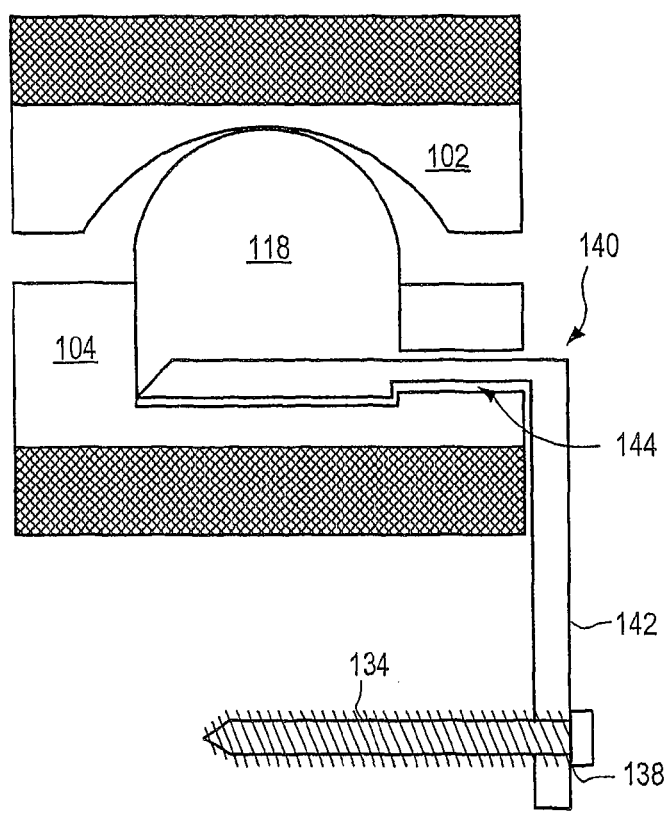
FIG. 4D is a cross-sectional view of an embodiment of an expandable implant employing an expansion plate with a securing keel to secure the device between vertebrae.

In some embodiments, an implant may be secured in place with a portion of an expansion member. As shown in FIG. 4D, expansion member 140 may include portion 142 with one or more openings 138 defined therethrough. In some embodiments, portion 142 may be a keel. After expansion member 140 is impacted into place, one or more screws 134 may be inserted through portion 142 and secured into a vertebral body. Expansion member 140 and lower body 104 may also include complementary engaging portion 144 to secure expansion member 140 with lower body 104.

Figure 4E:
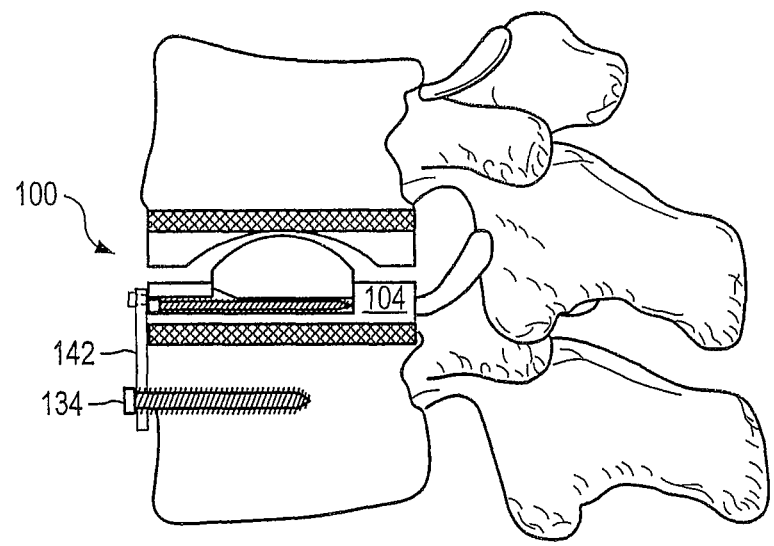
FIG. 4E is a side perspective of an embodiment of an expandable implant employing a securing keel.
Figure 5:
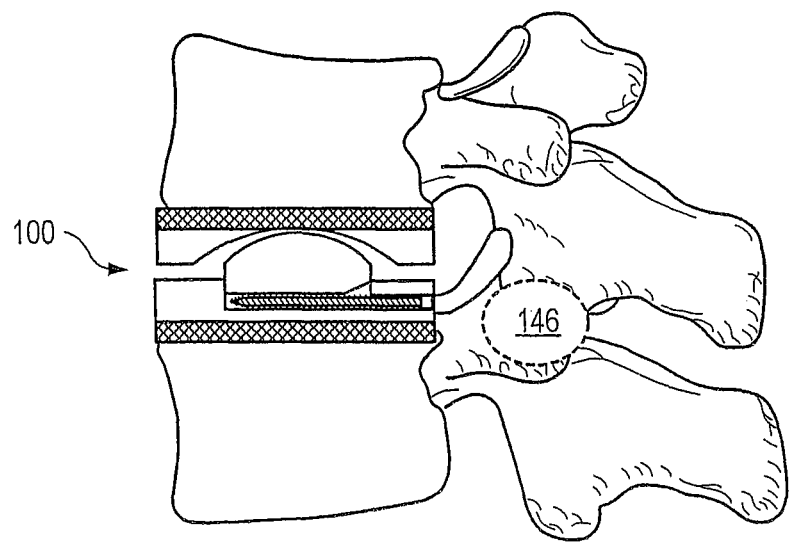
FIG. 5 is a side perspective view illustrating placement of an expandable implant in an intervertebral space.

FIG. 4E illustrates implant 100 secured between vertebrae of a human spine. One end of portion 142 may be secured onto lower body 104 of implant 100. Portion 142 may be rotated after placement of the device in the intervertebral space. After rotation of portion 142, the portion is secured to the vertebral body above or below implant 100 with one or more fasteners 134 (e.g., screws). FIG. 5 depicts implant 100 following insertion in a spinal column. In some embodiments, implant 100 may be posteriorly inserted and expanded through void space 146 created by removal of a facet joint.

Figure 6A:
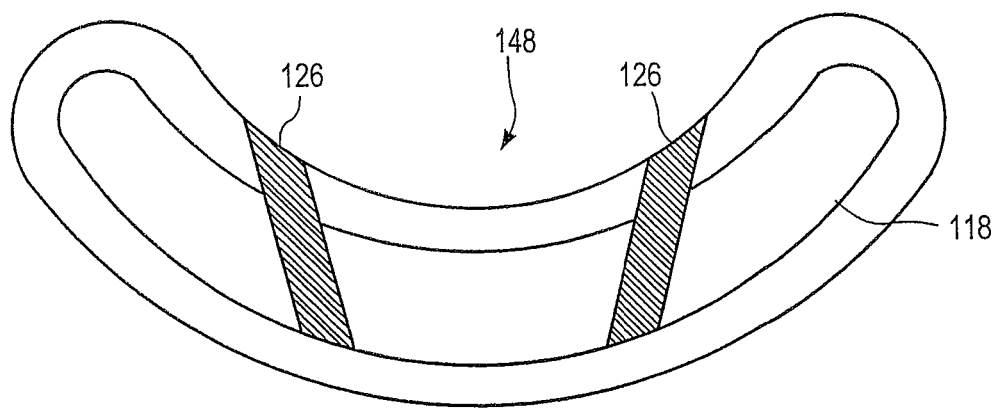
FIG. 6A depicts a top view of an embodiment of a c-shaped, expandable implant.

FIG. 6A depicts a top view of an embodiment of a c-shaped expandable implant. Implant 148 may include insert 118. In some embodiments, insert 118 may be substantially the same as a shape of an upper body and/or lower body of implant 148. In certain embodiments, a shape of insert 118 may be different from a shape of upper body 102 and/or lower body 104. For example, a shape of insert 118 may be oval or round, and upper body 102 and/or lower body 104 may be c-shaped. Implant 148 may include two or more expansion members 124. Expansion members 124 may be inserted into openings 126 to elevate insert 118 from recess 116.

Figure 6B:
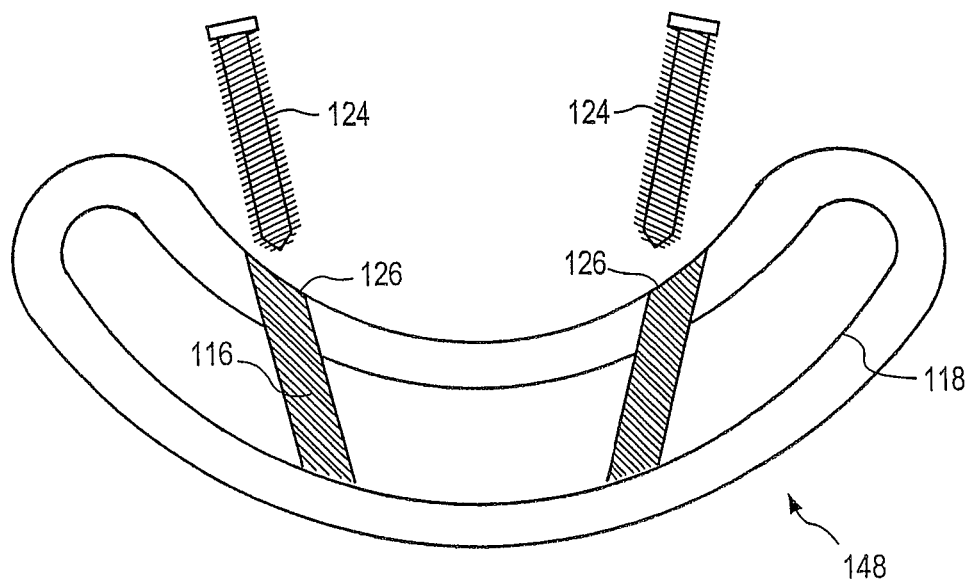
FIG. 6B is a top view of an embodiment of a c-shaped expandable implant, illustrating insertion of expansion screws to expand the implant.
Figure 6C:
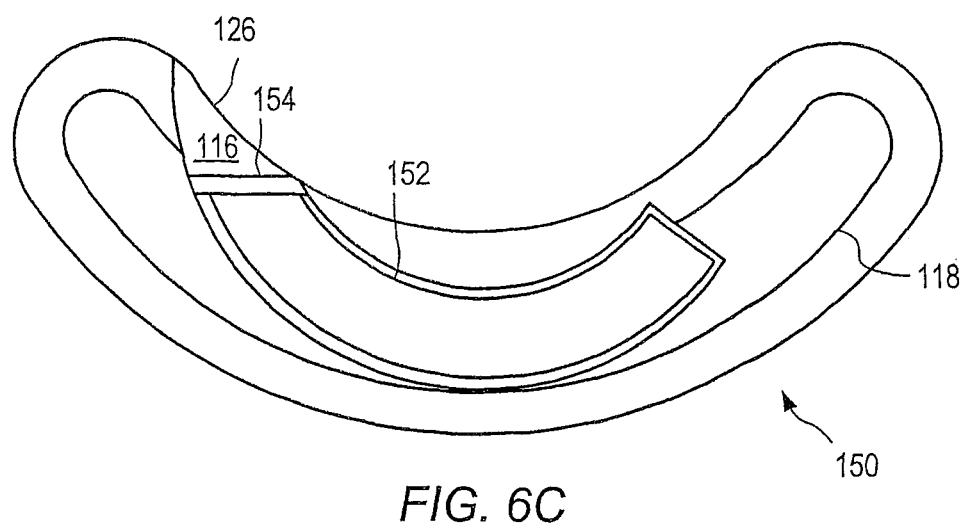
FIG. 6C is a top view of an embodiment of a c-shaped, expandable implant, illustrating insertion of a non-threaded expansion member to expand the implant.

FIGS. 6B and 6C illustrate the insertion of expansion members into c-shaped implants. In the embodiment depicted in FIG. 6B, expansion members 124 for implant 148 may be screws. One or more expansion members 124 may be inserted through one or more openings 126. In some embodiments, one or more openings 126 may be threaded. In certain embodiments, as shown in FIG. 6C, implant 150 may include expansion member 152. Expansion member 152 may be an elongated or curved member sized and/or shaped for insertion through opening 126. In some embodiments, expansion member 152 may have an angled or wedge portion. Opening 126 may be non-threaded. Expansion member 152 may be impacted or driven through opening 126 into recess 116 to engage insert 118. Recess 116 may be an arcuate channel or a groove shaped and/or sized to facilitate insertion of expansion member 152 before or after implant 150 has been positioned between vertebrae of a human spine. A shape of expansion member 152 may be complementary to a shape of recess 116. Engaging insert 118 with expansion member 152 may elevate the insert from the lower body of implant 150, increasing a separation distance between the upper body and the lower body of the implant. In some embodiments, member 154 may be used to retain expansion member 152 in recess 116. Member 154 may be, for example, a cap or set screw that fits through opening 126 into a portion (e.g., a threaded portion) of recess 116.

Figure 6D:
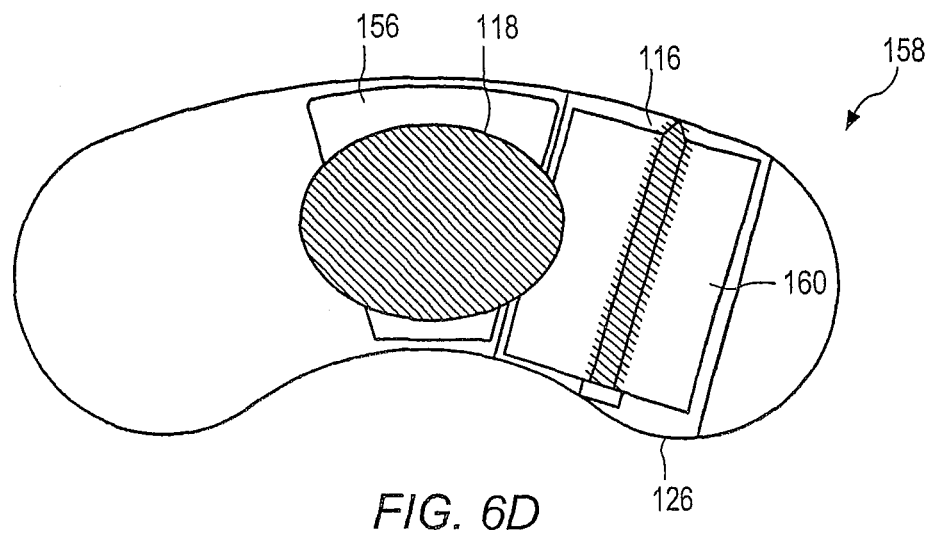
FIG. 6D is a top view of an embodiment of a c-shaped, expandable implant with a posteriorly positioned expansion opening.

FIG. 6D depicts an alternative embodiment for posteriorly securing an expansion member in a c-shaped implant. Expansion member 156 may be an expansion plate. Expansion member 156 may be inserted through opening 126 of implant 158. Expansion member 156 may be inserted posteriorly through opening 126 to slidingly engage insert 118 in implant 158 in the medial-lateral direction. After expansion, member 160 may be inserted in recess 116. In some embodiments, member 160 may be a retainer plate. In some embodiments, member 160 may substantially fill recess 116. In certain embodiments, member 160 may include a securing device such as, for example, a screw.

Figure 7A:
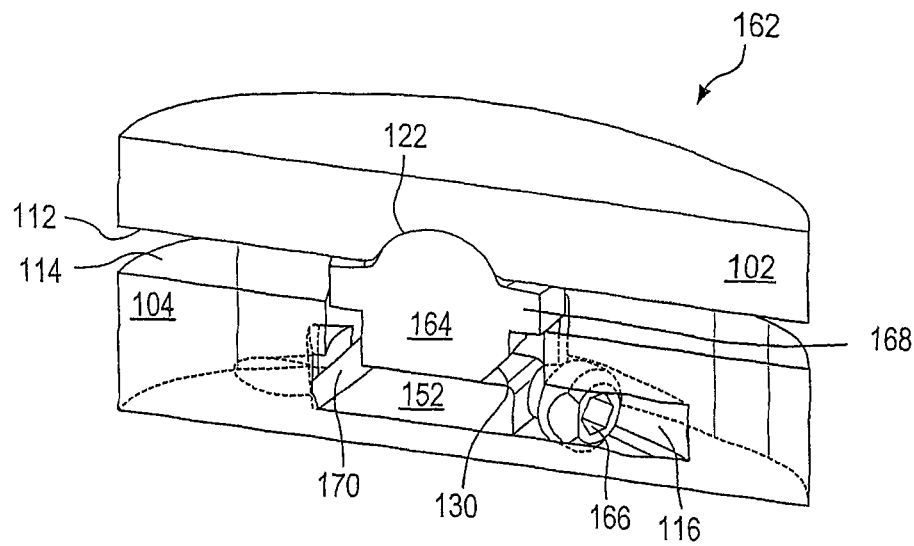
FIG. 7A is a cross-sectional view of an embodiment of an expandable, articulating implant including an insert with stops.
Figure 7B:
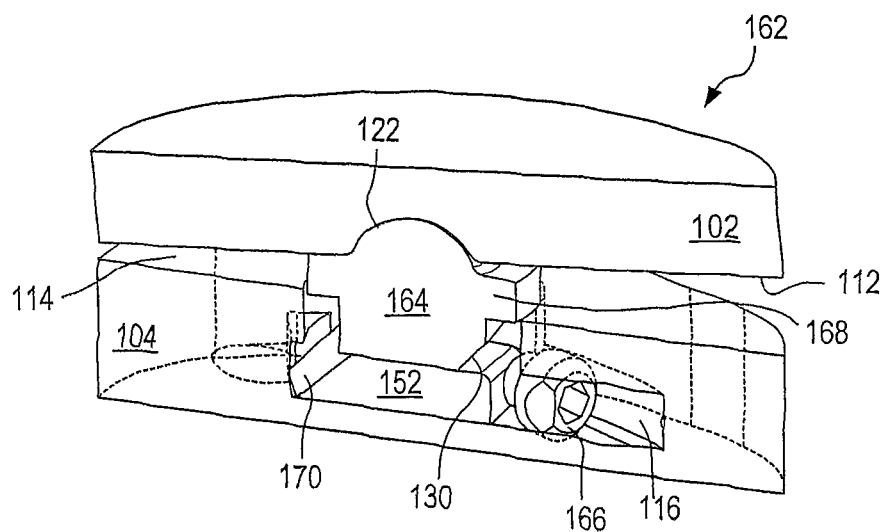
FIG. 7B is a cross-sectional view of the embodiment depicted in FIG. 7A showing articulation of the implant.

FIGS. 7A and 7B depict a cross-sectional view of another embodiment of an expandable, articulating implant. Implant 162 may include upper body 102, lower body 104, insert 164, expansion member 152, and set screw 166 or similar device. Insert 164 may include one or more stops 168. In some embodiments, stop 168 may be a lip or ledge around a circumference of insert 164. In certain embodiments, insert 164 may include angled portion 130. In certain embodiments, expansion member 152 may include angled portion 170. Before insertion of expansion member 152 into recess 116, inferior surface 112 of upper body 102 may rest on superior surface 114 of lower body 104.

With insert 164 positioned in recess 116 of lower body 104, expansion member 152 may be inserted into recess 116. Angled portion 170 of expansion member 152 may engage angled portion 130 of insert 164 and expand implant 162. In some embodiments, set screw 166 may be used to inhibit backout of expansion member 152 after insertion of the expansion member. In certain embodiments, set screw 166 may be used to advance expansion member 152 as well as to inhibit backout of the expansion member.

After expansion of implant 162, a separation distance between inferior surface 112 of upper body 102 and superior surface 114 of lower body 104 may allow articulation of the upper body with convex superior surface 122 of insert 164. FIG. 7A depicts implant 162 after expansion. As depicted in FIG. 7A, upper body 102 is substantially parallel to lower body 104. FIG. 7B depicts implant 162 following articulation of upper body 102 with respect to lower body 104. As depicted in FIG. 7B, stops 168 may limit an angular range of motion of upper body 102 with respect to lower body 104. In some embodiments, a shape and/or thickness of stops 168 may limit a range of rotation of upper body 102 with respect to lower body 104 to less than about 20°. For example, a range of rotation of upper body 102 may be limited to less than about 5°, less than about 10°, or less than about 15°. A range of rotation may depend upon, for example, a shape (e.g., round, ellipsoidal, etc.) of the convex portion of superior surface 122 of insert 164.

Figure 8A:
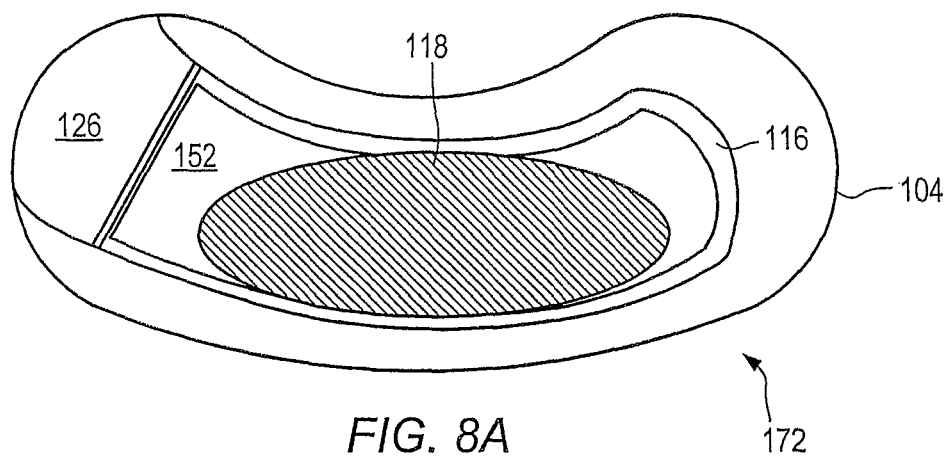
FIG. 8A is a top view of an embodiment of a c-shaped, expandable implant, illustrating the insertion of an expansion plate to expand the implant.
Figure 8B:
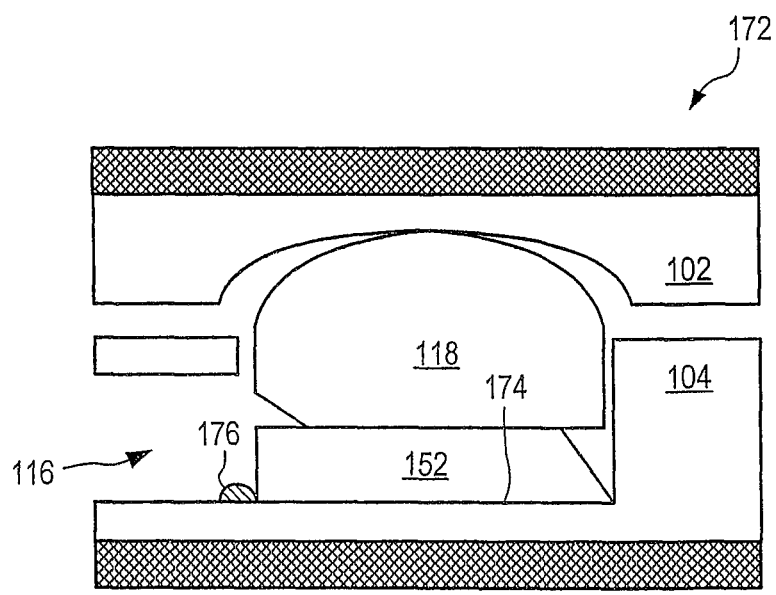
FIG. 8B is a side cross-sectional view of an embodiment of a c-shaped, expandable implant, illustrating the insertion of an expansion plate to expand the implant.

FIGS. 8A and 8B depict different cross-sectional views of an embodiment of an expandable, articulating c-shaped implant. As shown in FIG. 8A, implant 172 depicts recess 116 designed to accept arcuate expansion member 152. Implant 172 may have opening 126 on an end (e.g., a short side) of the implant. Expansion member 152 may be impacted into place through opening 126 to elevate insert 118 from lower body 104 after implant 172 has been positioned in an intervertebral space. Recess 116, as well as expansion member 152, may have substantially the same shape (e.g., substantially the same curvature) as a portion of the upper body and/or the lower body of implant 172. In some embodiments, a portion of insert 118 may be oval or round (e.g., ellipsoidal, spherical) to allow improved biomechanical motion of the implant. In some embodiments, a bottom of recess 116 may include a feature (e.g., an integral part of the lower body or an element coupled to a portion of the lower body) designed to retain expansion member 152 in position after expansion. For example, as depicted in FIG. 8B, surface 174 of recess 116 may include lip 176 or other feature designed to retain expansion member 152 in the recess. During insertion of implant 172, a surgeon may force expansion member 152 over lip 176 into place. Passage of expansion member 152 over lip 176 and into place may allow the surgeon to feel when expansion member 152 has been properly inserted. In some embodiments, lip 176 may inhibit dislocation of the implant (e.g., backout of expansion member 152).

Figure 8C:
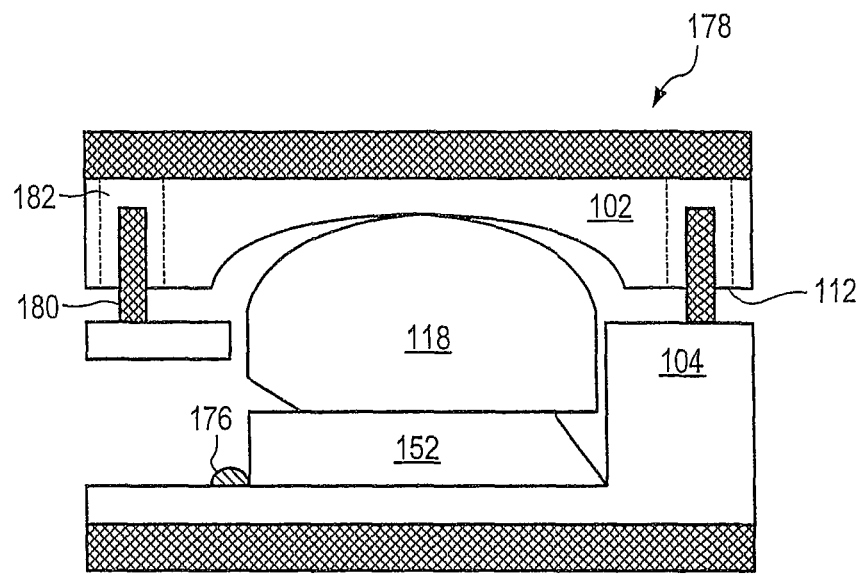
FIG. 8C is a side cross-sectional view of an embodiment of an expandable implant, featuring stabilizers.
Figure 8D:
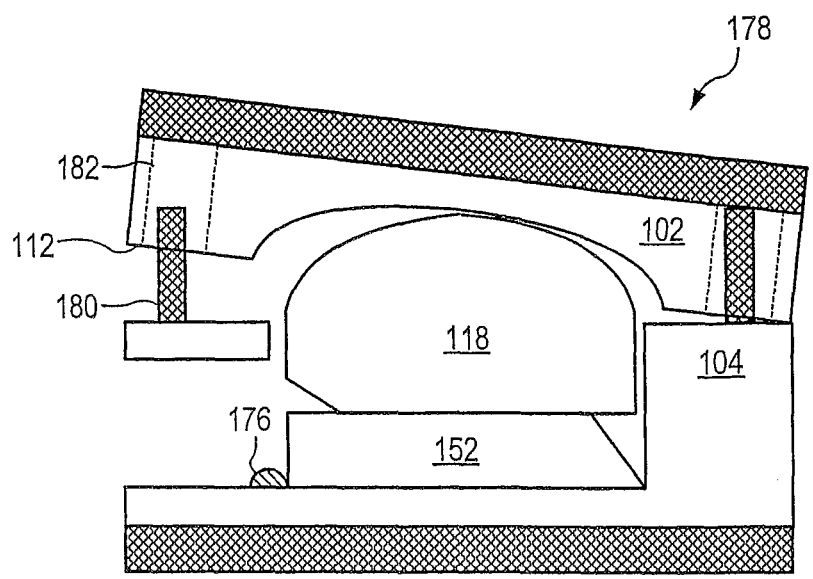
FIG. 8D is a side cross-sectional view of an embodiment of an expandable implant in flexion, featuring stabilizers.

FIGS. 8C and 8D depict cross-sectional views of an embodiment of an expandable, articulating implant. Implant 178 may include stabilizers 180. Stabilizers 180 may be coupled to lower body 104 and may extend from the lower body into openings 182 in upper body 102. Stabilizers 180 and/or openings 182 may be of various sizes and/or shapes. For example, Stabilizers 180 may be substantially round and openings 182 may be substantially oval, allowing torsional mobility of upper body 102. In some embodiments, stabilizers 180 may be captive. Stabilizers 180 may inhibit dislocation of upper body 102 from lower body 104 during flexion, extension, and/or torsional motion of implant 178. As shown in FIG. 8D, when implant 178 is flexed or extended, stabilizers 180 may inhibit dislocation of upper body 102 from lower body 104.

Figure 9A:
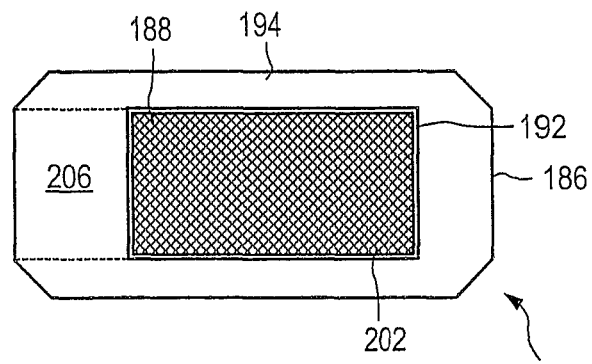
FIG. 9A is a top view of an embodiment of an expandable cage.
Figure 9B:
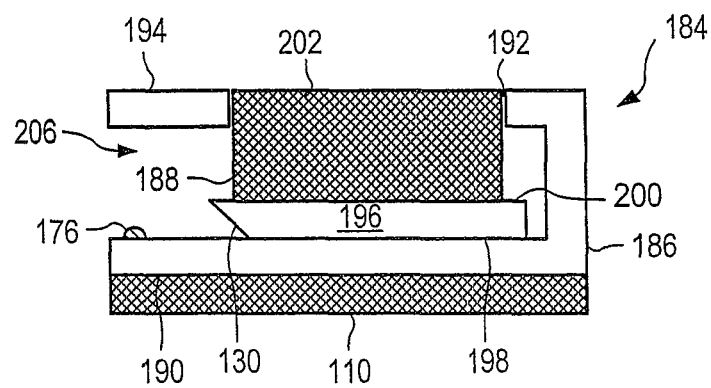
FIG. 9B is a side cross-sectional view of an embodiment of an expandable cage prior to expansion.
Figure 9C:
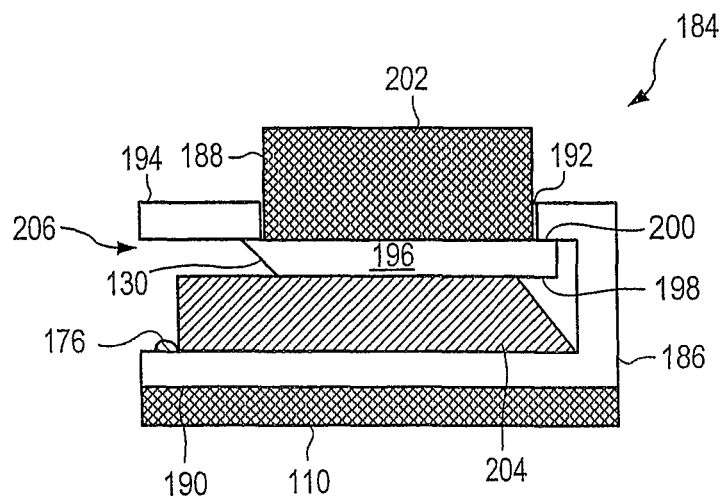
FIG. 9C is a side cross-sectional view of an embodiment of an expandable following expansion.

The disclosed techniques of expanding an implant by insertion of an expansion member may also be employed to expand a PLIF or TLIF cage. FIGS. 9A-9C depict views of an embodiment of an expandable cage. FIG. 9A depicts a top view of cage 184. FIG. 9B depicts a cross-sectional view of cage 184 before expansion. In some embodiments, cage 184 may include cage element 186 and insert 188. Insert 188 may be positioned in cage element 186. In certain embodiments, cage element 186 may include osteoconductive scaffolding 110. For example, cage element 186 may include osteoconductive scaffolding 110 on inferior surface 190. An osteoconductive substance may be placed in osteoconductive scaffolding 110 to promote bone growth into cage 184. In some embodiments, cage element 186 may include opening 192 through superior surface 194.

In some embodiments, insert 188 may include member 196 having inferior surface 198 and superior surface 200. In some embodiments, member 196 may be substantially planar (e.g., a plate). In certain embodiments, osteoconductive scaffolding 202 may be coupled to superior surface 200 of member 196. Member 196 may include angled portion 130. Angled portion 130 may facilitate expansion of cage 184 (e.g., elevation of insert 188) upon insertion of expansion member 204. Expansion member 204 may be inserted into opening 206 of cage element 186 and advanced (e.g., impacted, driven) to engage angled portion 130 of member 196. FIG. 9C depicts a cross-sectional view of expanded cage 184. In some embodiments, lip 176 may inhibit dislocation of expansion member 204 after expansion of cage 184. In certain embodiments, lip 176 and/or one or more other features may secure expansion member 204 in cage element 186 in such a way that a surgeon may sense tactilely when the expansion member is fully inserted in cage 184.

Figure 9D:
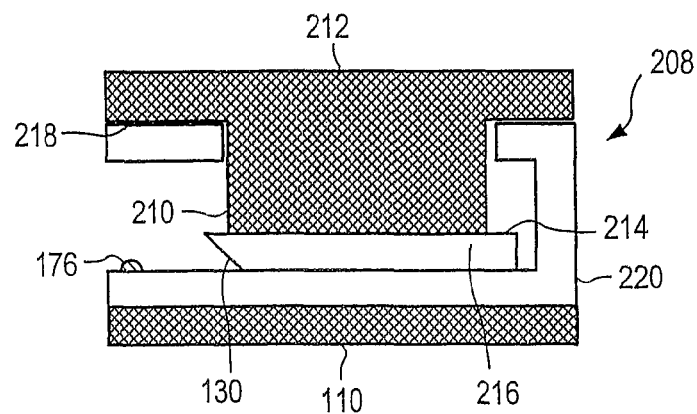
FIG. 9D is a side cross-sectional view of an embodiment of an expandable cage with a larger upper surface area prior to expansion.
Figure 9E:
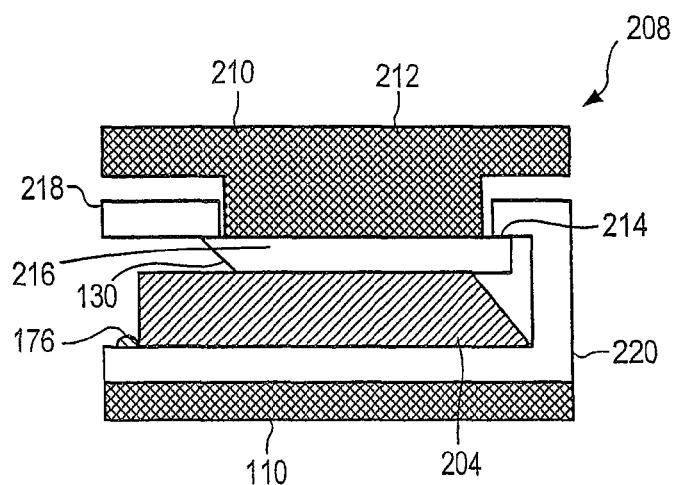
FIG. 9E is a side cross-sectional view of an embodiment of an expandable cage with a larger upper surface area following expansion.

FIGS. 9D and 9E depict cross-sectional views of an embodiment of an expandable cage. FIG. 9D depicts cage 208 before expansion. Insert 210 of cage 208 may include osteoconductive scaffolding 212 coupled to superior surface 214 of member 216. In some embodiments, osteoconductive scaffolding 212 may have a T-shaped cross-section, such that the osteoconductive scaffolding rests upon superior surface 218 of cage element 220, providing an increased surface area between the osteoconductive scaffolding and the bony endplates within the intervertebral space.

Figure 9F:
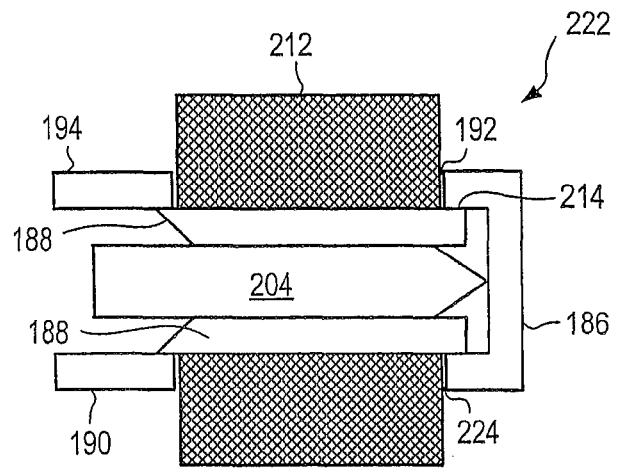
FIG. 9F is a cross-sectional view of an embodiment of a cage that is expandable in two directions.

In some embodiments, expandable cages may be expanded in two or more dimensions. FIG. 9F depicts an embodiment of a cage that may be expanded in two dimensions. Cage 222 may include cage element 186 and inserts 188. Cage element 186 may include opening 224 through inferior surface 190 as well as opening 192 through superior surface 194. Two inserts 188 may be positioned in cage element 186. As expansion member 204 is inserted into cage element 186 between inserts 188, the inserts may be forced through openings 192, 224 to engage the bony endplates within the intervertebral space.

Figure 10A:
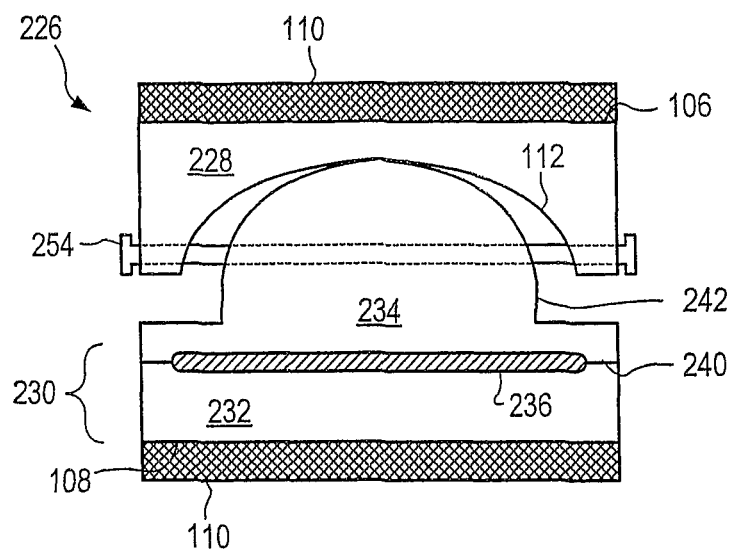
FIG. 10A is a posterior view of an embodiment of a c-shaped lordotic expandable implant.
Figure 10B:
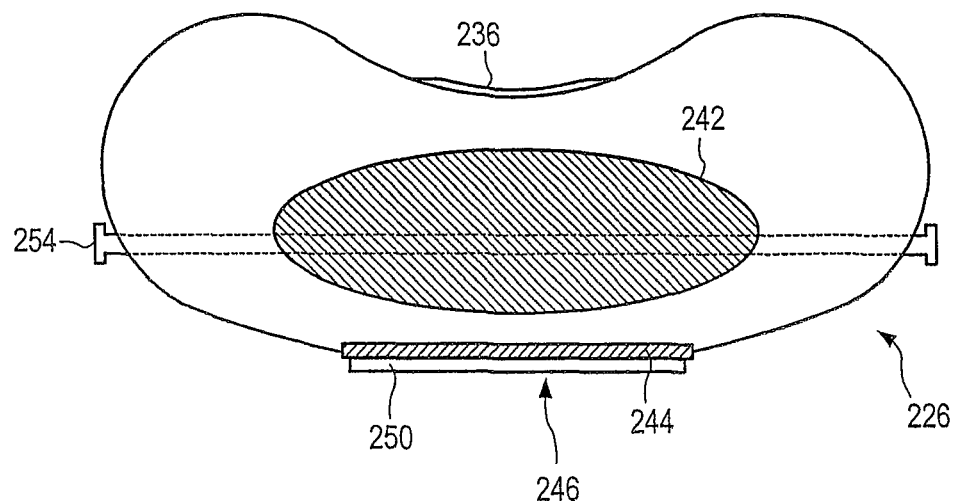
FIG. 10B is a top view of an embodiment of a c-shaped lordotic expandable implant.
Figure 11A:
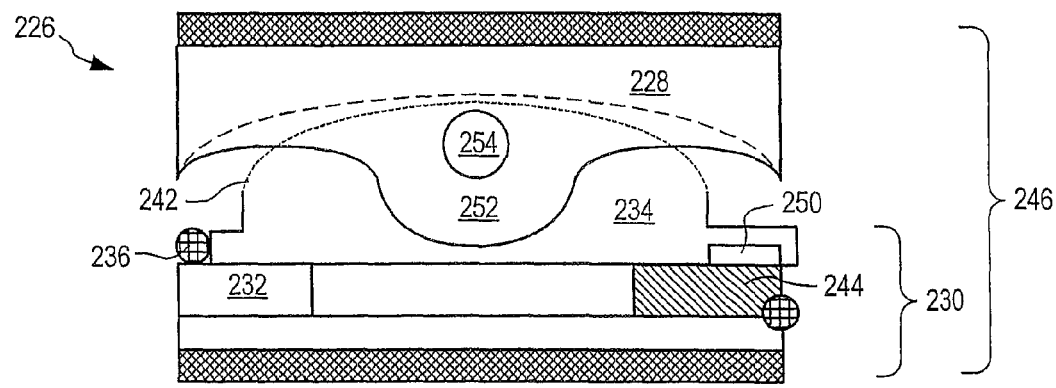
FIG. 11A is a lateral view of an embodiment of a c-shaped lordotic expandable implant prior to expansion.
Figure 11B:
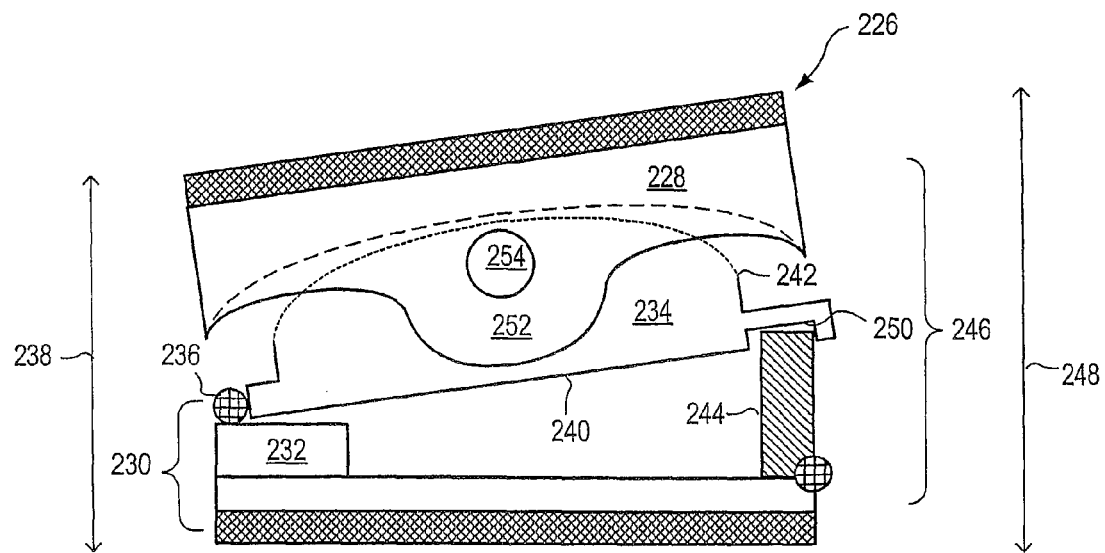
FIG. 11B is a lateral view of an embodiment of a c-shaped lordotic expandable implant following expansion.

FIGS. 10A, 10B, 11A, and 11B depict an embodiment of a lordotic, c-shaped expandable, articulating implant. The lumbar spine is lordotic, thus the anterior disc height is naturally larger than the posterior disc height. Therefore, an expandable implant for the lumbar spine may advantageously expand into a lordotic position. FIG. 10A depicts a posterior view of implant 226. FIG. 10B depicts a top view of implant 226. FIGS. 11A and 11B depict cross-sectional views of implant 226 before and after expansion of the implant, respectively.

Implant 226 may include upper body 228 and lower body 230. Lower body 230 may include two or more members. In some embodiments, members of lower body 230 may be coupled (e.g., hinged). Portions of upper body 228 and lower body 230 may be substantially parallel before expansion of implant 226. In some embodiments, superior surface 106 of upper body 228 and inferior surface 108 of lower body 230 may include osteoconductive scaffolding 110. In certain embodiments, at least a portion of inferior surface 112 of upper body 228 may be substantially concave.

Lower body 230 may include lower portion 232 and upper portion 234. In some embodiments, lower portion 232 and upper portion 234 of lower body 230 may be coupled with hinge 236. Hinge 236 may effectively fix posterior disc height 238 (shown in FIG. 11B). In certain embodiments, inferior surface 240 of upper portion 234 may be substantially flat. In certain embodiments, at least a portion of superior surface 242 of upper portion 234 may be convex. Lower portion 232 and inferior surface 240 of upper portion 234 may be substantially parallel prior to expansion. In some embodiments, lifting mechanism 244 may be located proximate anterior end 246 of lower portion 232. Following insertion of implant 226 in an intervertebral space, lifting mechanism 244 may be engaged to increase a height of anterior end 246 of implant 226. Increasing a height of anterior end 246 of implant 226 may provide a desired anterior disc height 248 and proper lordosis. As depicted in FIGS. 11A and 11B, anterior end 246 of upper portion 234 may include notch 250. Notch 250 may engage lifting mechanism 244 to secure a height of anterior end 246 of implant 226 following expansion.

In some embodiments, at least a portion of inferior surface 112 of upper body 228 may be concave. A concave portion of inferior surface 112 of upper body 228 may articulate with a convex portion of superior surface 242 of upper portion 234. When viewed in the medial or lateral direction, as shown in FIGS. 11A and 11B, upper body 228 may include extension 252 for coupling to elongated member 254. In some embodiments, elongated member 254 may couple upper body 228 to upper portion 234 of lower body 230, thus reducing a possibility of dislocation. FIG. 11B depicts the posterior placement of hinge 236 and anterior placement of lifting mechanism 244, with elongated member 254 positioned through upper body 228 and upper portion 234 of lower body 230.

Figure 12A:
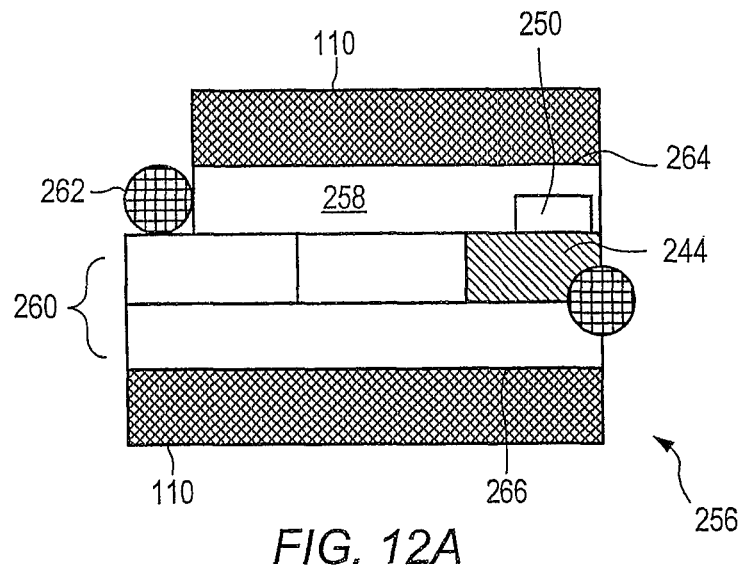
FIG. 12A is a side cross-sectional view of an embodiment of an expandable lordotic cage prior to expansion.
Figure 12B:
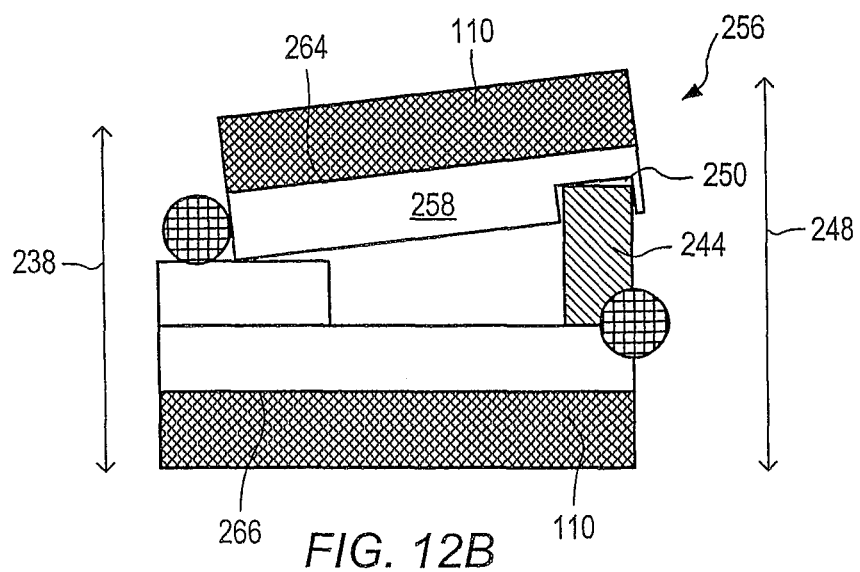
FIG. 12B is a side cross-sectional view of an embodiment of an expandable lordotic cage following expansion.

A lifting mechanism may also be used to achieve desired lordosis with expandable PLIF and TLIF cages, as shown in FIGS. 12A and 12B. FIGS. 12A and 12B depict side cross-sectional views of cage 256 before and after expansion, respectively. Cage 256 may include upper body 258 and lower body 260. In some embodiments, hinge 262 may posteriorly couple upper body 258 to lower body 260. In certain embodiments, hinge 262 may fix posterior disc height 238 after expansion of cage 256. Superior surface 264 of upper body 258 and inferior surface 266 of lower body 260 may include osteoconductive scaffolding 110. Lifting mechanism 244 may be engaged to expand cage 256. In some embodiments, lifting mechanism 244 may engage notch 250 after expansion, reducing the possibility for dislocation after insertion and expansion of cage 256. A height of lifting mechanism 244 may be chosen to achieve a desired anterior disc height 248 (e.g., to achieve proper lordosis).

Figure 13A:
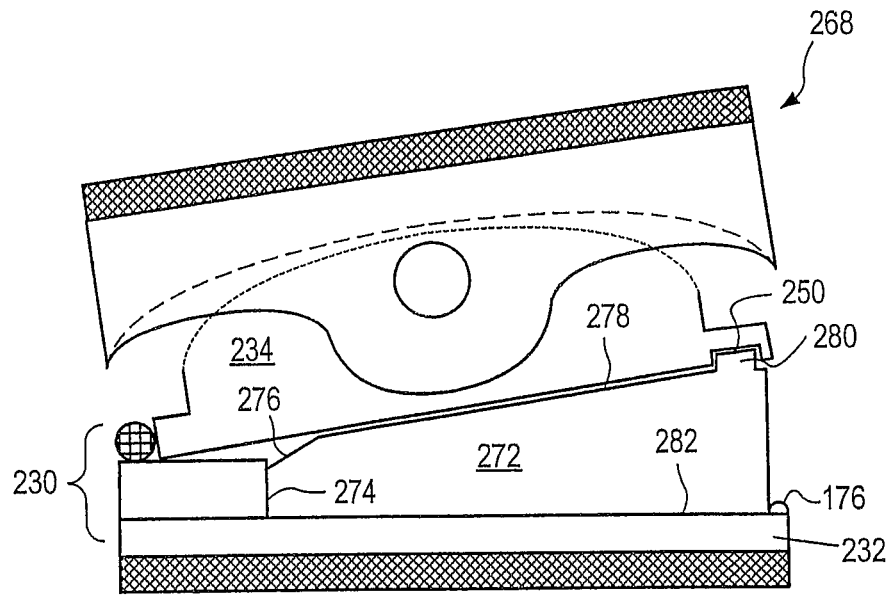
FIG. 13A is a lateral view of an embodiment of a c-shaped lordotic expandable implant with an inclined expansion member.
Figure 13B:
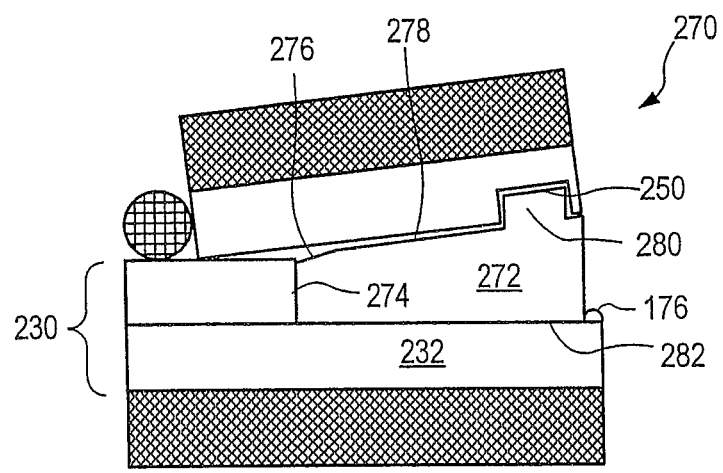
FIG. 13B is a side cross-sectional view of an embodiment of an expandable lordotic cage with an inclined expansion member.

FIG. 13A depicts a cross-sectional view of an expandable, articulating lordotic implant. FIG. 13B depicts a cross-sectional view of an embodiment of an expandable lordotic cage. Implant 268 in FIG. 13A and cage 270 in FIG. 13B both include expansion member 272 to achieve proper lordosis. In some embodiments, expansion member 272 is generally wedge-shaped. In certain embodiments, posterior end 274 of expansion member 272 may include angled portion 276. Angled portion 276 may facilitate expansion of implant 268 and cage 270. Protrusion 280 may be located on superior surface 278 of the anterior end of expansion member 272. As show in FIG. 13A, expansion member 272 may be inserted between upper portion 234 and lower portion 232 of lower body 230. Protrusion 280 may engage notch 250 to secure a height of implant 268 and cage 270 following expansion. Lip 176 or other feature may be located on an anterior end of superior surface 282 of lower portion 232 to reduce the potential of dislocation of expansion member 272.

Figure 14A:
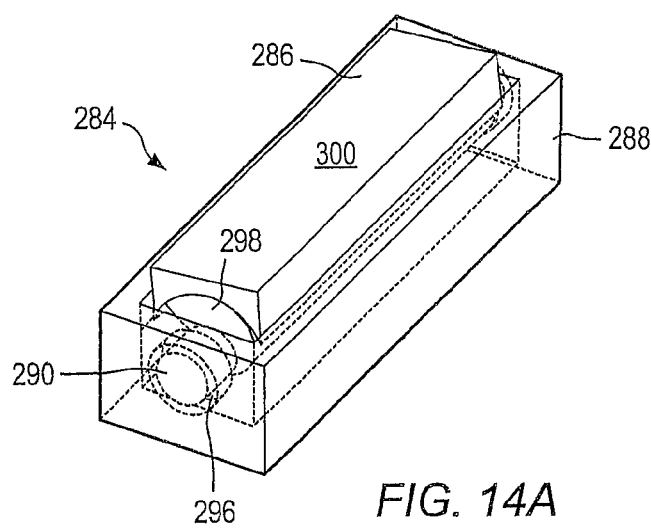
FIG. 14A is a perspective view of an embodiment of an expandable, articulating implant with a spiral cam.
Figure 14B:
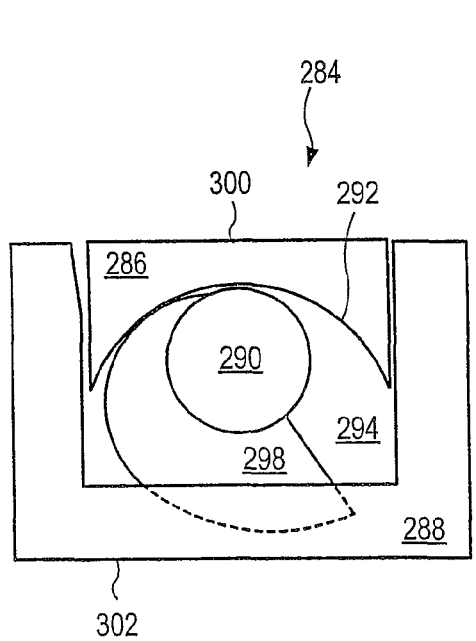
FIG. 14B is a cross-sectional view of the implant embodiment depicted in FIG. 14A prior to expansion.
Figure 14C:
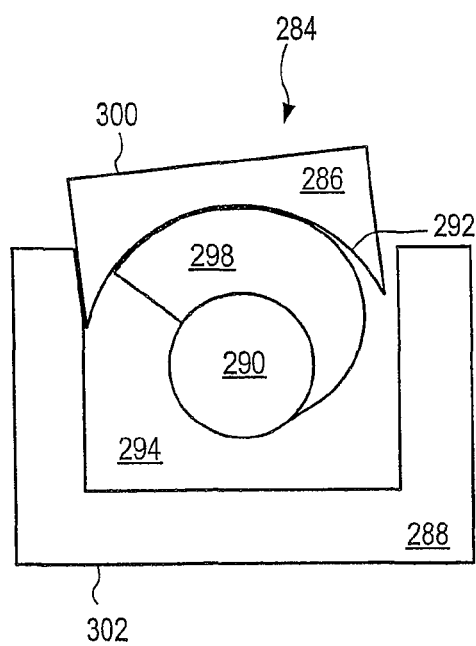
FIG. 14C is a cross-sectional view of the implant embodiment depicted in FIG. 14A following expansion.

FIG. 14A depicts a perspective view of an embodiment of an expandable, articulating implant. Implant 284 may be of any size and/or shape known in the art. FIGS. 14B and 14C depict cross-sectional views of implant 284 before and after expansion, respectively. Implant 284 may include upper body 286, lower body 288, and elongated member 290. In some embodiments, lower body 288 may include channel 294. Lower body 288 may include openings 296 on opposing walls for receiving elongated member 290. In certain embodiments, elongated member 290 may traverse a portion (e.g., a length) of implant 284.

In some embodiments, elongated member 290 may include cam portion 298. In certain embodiments, cam portion 298 may include a spiral cam portion. Cam portion 298 may include an arcuate surface that resides within channel 294 of lower body 288. In some embodiments, cam portion 298 may be coupled to elongated member 290. In certain embodiments, cam portion 298 may form an integral part of elongated member 290. In some embodiments, cam portion 298 may wrap partially around elongated member 290 with increasing thickness. In some embodiments, as depicted in FIG. 14B, implant 284 may be in an unexpanded position when cam portion 298 rests at the bottom of channel 294. When elongated member 290 is rotated, cam portion 298 may spin upward to expand implant 284. FIG. 14C depicts a cross-sectional view of expanded implant 284.

Superior surface 300 of upper body 286 may contact the bony surface of a human vertebra after insertion of implant 284 in a human spine. In some embodiments, an inferior surface of upper body 286 may articulate with the arcuate surface of cam portion 298. In certain embodiments, upper body 286 may move back and forth against the arcuate surface of cam portion 298. This movement may allow biomechanical motion in a human spine in which implant 284 has been inserted and expanded. In some embodiments, elongated member 290 may be held in place in openings 296 to fix a height of implant 284 after expansion. For example, a ratcheting device or fastener (e.g., a set screw) may be used to fix a position of elongated member 290. In certain embodiments, superior surface 300 of upper body 286 and/or inferior surface 302 of lower body 288 may be coupled to osteoconductive scaffolding.

Figure 15A:
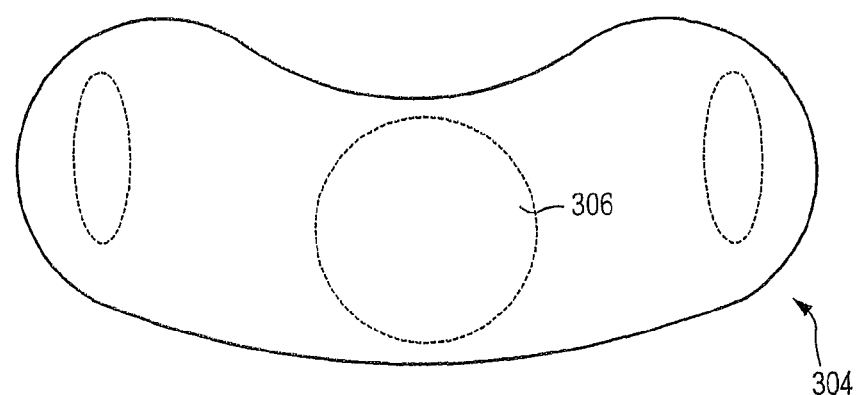
FIG. 15A is a top view of an embodiment of a c-shaped expandable, articulating implant with a round insert.
Figure 15B:
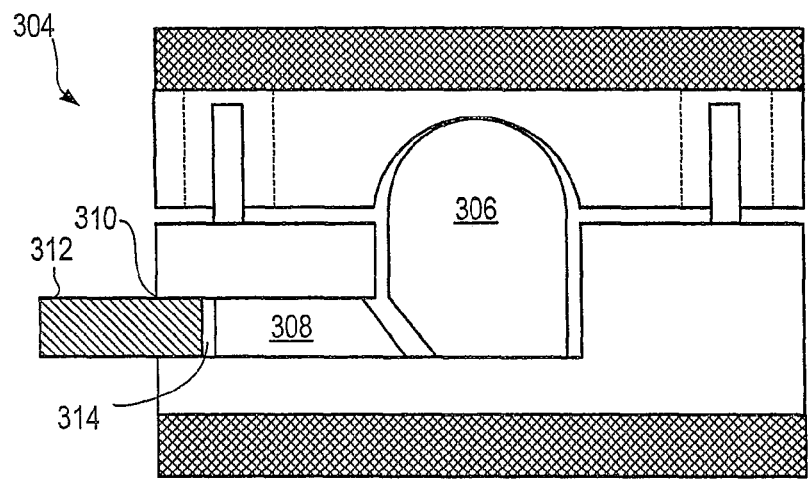
FIG. 15B a side cross-sectional view of an embodiment of a c-shaped implant with an expansion member/advancing element combination prior to expansion.
Figure 15C:
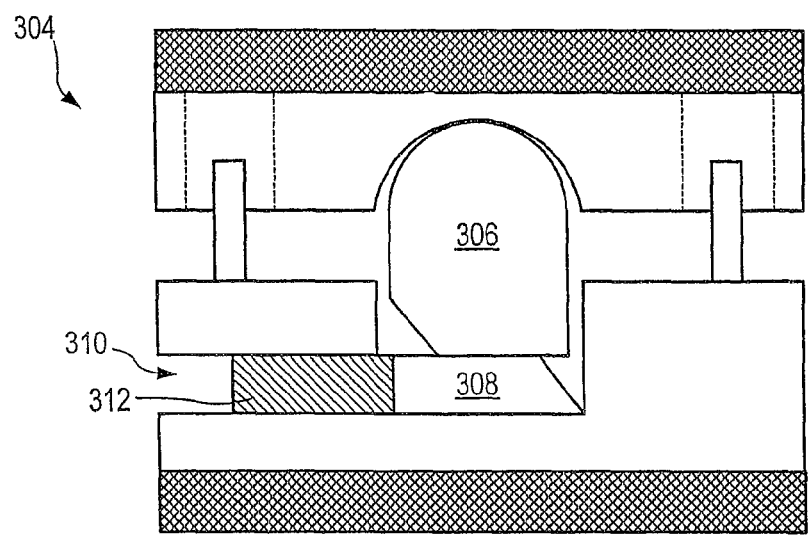
FIG. 15C is a side cross-sectional view of an embodiment of a c-shaped implant with an expansion member/advancing element combination following expansion.

FIGS. 15A-15C depict an embodiment of a c-shaped expandable, articulating implant. FIG. 15A depicts a top view of implant 304 with insert 306. In some embodiments, a portion of insert 306 may be substantially round, providing a close approximation to natural biomechanical motion. FIGS. 15B and 15C illustrate side cross-sectional views of implant 304 before and after expansion, respectively. Expansion member 308 may be inserted through opening 310. In some embodiments, opening 310 may be threaded. Advancing element 312 may be inserted in opening 310 following insertion of expansion member 308. Advancing element 312 may be used to advance expansion member 308 into position below insert 306. In some embodiments, advancing element 312 may remain in recess 314 to inhibit dislocation of expansion member 308 after expansion of implant 304. Use of advancing element 312 (e.g., a set screw) to advance expansion member 308 into place may reduce impaction during positioning of the expansion member. Reducing impaction during positioning of expansion member 308 may reduce stress on portions of a patient's body during the insertion procedure. It should be noted that the expansion member/advancing element combination may be employed with any of the disclosed implants, including cages.

Figure 16A:
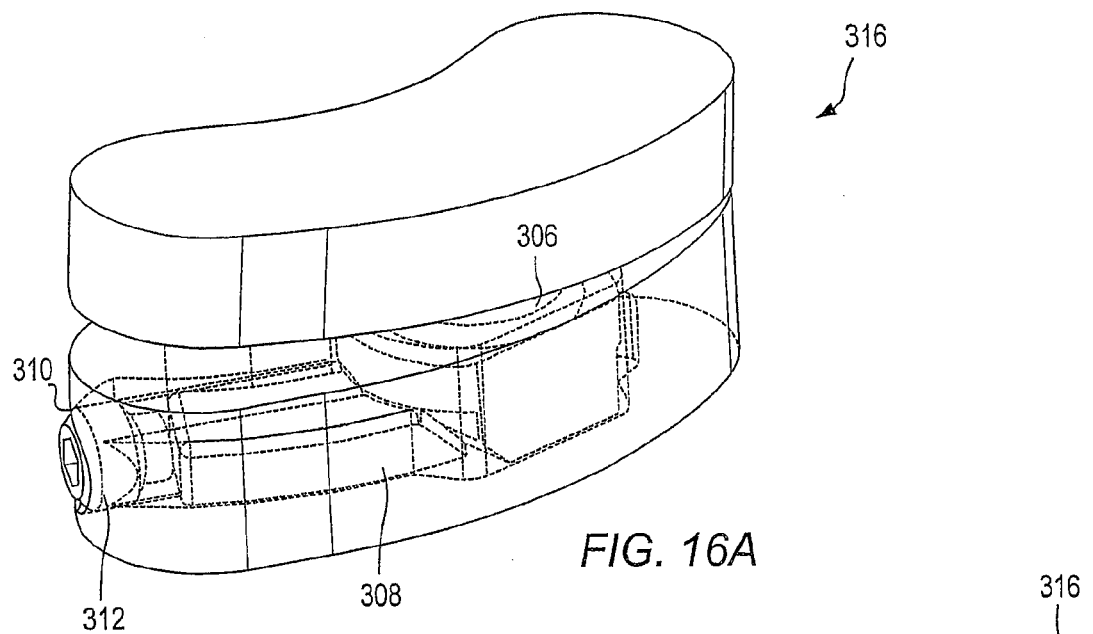
FIG. 16A is a perspective view of an embodiment of an expandable, articulating implant before expansion.
Figure 16B:
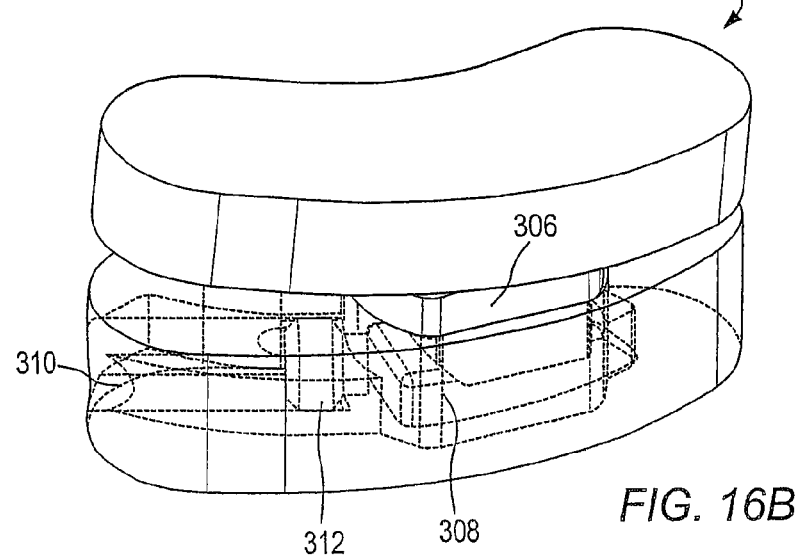
FIG. 16B is a perspective view of an embodiment of an expandable, articulating implant following expansion.

FIGS. 16A and 16B depict perspective views of an embodiment of a c-shaped expandable, articulating implant before and after expansion, respectively. As shown in FIG. 16A, implant 316 may include insert 306 and expansion member 308. Insertion of expansion member 308 is achieved by movement of advancing element 312 through opening 310 in an end of implant 316. Advancing expansion member 308 with advancing element 312 or other device (e.g., a threaded driver) rather than impacting the expansion member may allow a smaller expansion member to be used. Using a smaller expansion member may require a shorter access to the implant, allowing an implant to be positioned in a final TLIF position and then expanded. For example, a smaller expansion member may require a shorter access to the implant. Raising insert 306 with expansion member 308 may increase a height of implant 316. Increasing a height of implant 316 may increase a range of articulation of the implant after insertion of the implant in a human spine.

Figure 17:
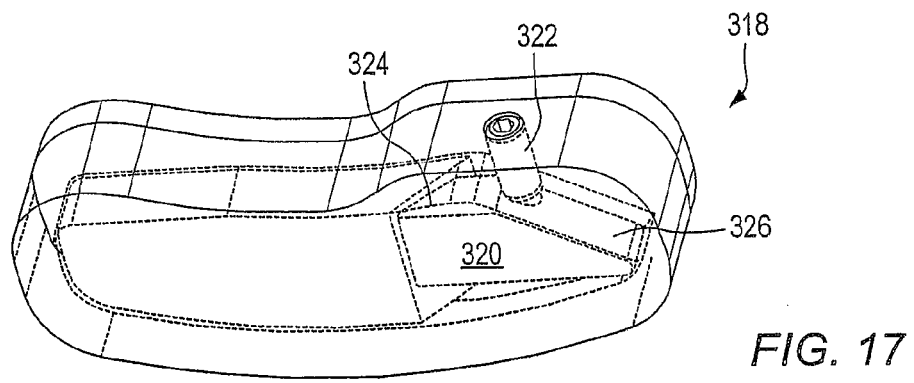
FIG. 17 is a perspective view of an embodiment of a portion of an implant with a double-wedged expansion member.

FIG. 17 depicts a perspective view of an embodiment of a portion of an expandable implant. Implant 318 may include expansion member 320. Expansion member 320 may be advanced with advancing element 322. As depicted in FIG. 17, advancing element 322 may be a screw. In some embodiments, advancing element 322 may engage expansion member 320 from a side (e.g., anterior side, posterior side) of implant 318. In some embodiments, expansion member 320 may include two angled portions. Angled portion 324 may engage a portion of implant 318 (e.g., an insert or a portion of an upper body or a lower body). Advancing element 322 may engage angled portion 326, thus allowing a component of the force from the advancing element to increase a height of implant 318. Accessing expansion member 320 from a longer side (e.g., posterior side) of implant 318 (PLIF approach) may advantageously require a smaller incision and/or cause less tissue damage during insertion of the implant than accessing the expansion member from shorter end of the implant (TLIF approach).

Figure 18A:
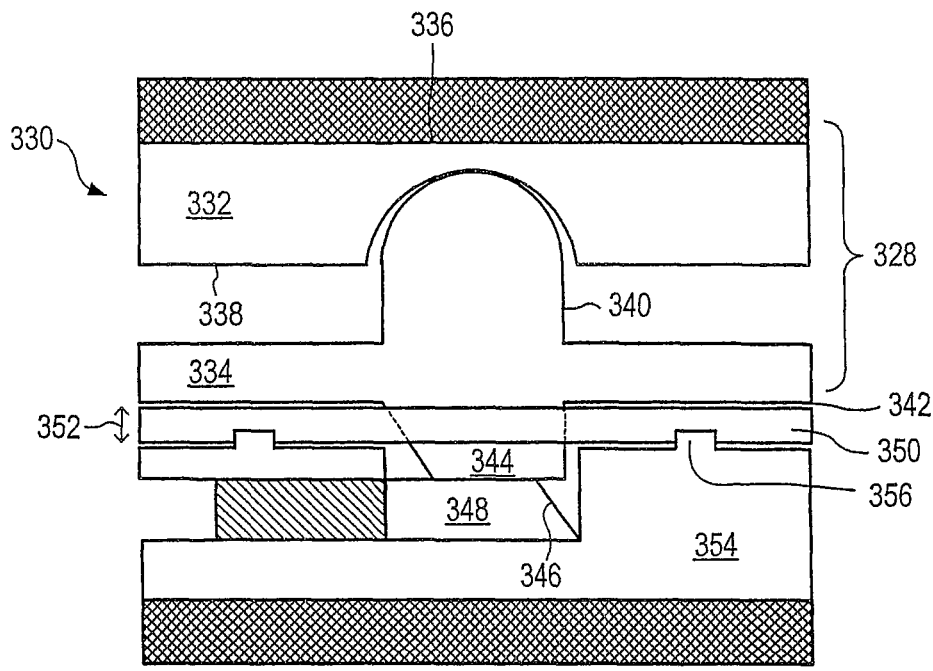
FIG. 18A is a cross-sectional view of an embodiment of an expandable, articulating implant with a wedged insert.

FIG. 18A depicts an embodiment of a c-shaped expandable, articulating implant designed to accept a spacer between an upper body and a lower body of the implant after expansion. Upper body 328 of implant 330 may include upper portion 332 and lower portion 334. Upper portion 332 and lower portion 334 may both have substantially the same c-shape. In some embodiments, superior surface 336 of upper portion 332 may contact a bony surface of a vertebral body after insertion of implant 330 in a human spine. At least a portion of inferior surface 338 of upper portion 332 may be concave. At least a portion of superior surface 340 of lower portion 334 may be convex. In some embodiments, inferior surface 338 of upper portion 332 may articulate with superior surface 340 of lower portion 334.

In some embodiments, inferior surface 342 of lower portion 334 may include angled portion 344. As depicted in FIG. 18A, angled portion 344 may be a downward projecting ramp. In certain embodiments, angled portion 346 of expansion member 348 may engage angled portion 344 of lower portion 334 during insertion of the expansion member. After expansion of implant 330, spacer 350 may be inserted in gap 352 between lower portion 334 of upper body 328 and lower body 354. In some embodiments, spacer 350 may be a shim. In certain embodiments, a superior surface of lower body 354 may include one or more guides 356. Guides 356 may include, but are not limited to, protrusions, keyways, rails, grooves, ridges, notches, and/or combinations thereof. Guides 356 may align spacer 350 during insertion of the spacer. In some embodiments, guides 356 may inhibit dislocation of spacer 350 after insertion of the spacer.

Figure 18B:
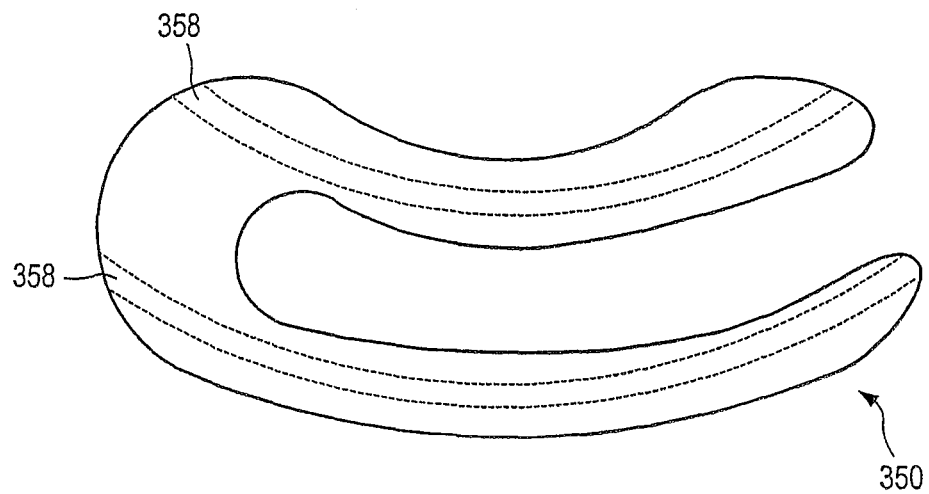
FIG. 18B is a top view of an embodiment of a spacer.

FIG. 18B depicts a top view of an embodiment of spacer 350. In some embodiments, spacer 350 may have substantially the same shape and/or profile as upper body 328 and/or lower body 354 of implant 330. In certain embodiments, spacer 350 may be sized such that the spacer is substantially flush with an outside edge of implant 330. In other embodiments, spacer 350 may protrude from implant 330 (e.g., from a side surface of implant 330) to facilitate alignment and placement of the spacer in the implant. In some embodiments, spacer 350 may include one or more guides 358. Guides 358 may include, but are not limited to, grooves, keyways, rails, ridges, protrusions, notches, and/or combinations thereof. Guides 358 on spacer 350 may be complementary to guides on a portion (e.g., upper body, lower body) of an implant.

A height of a spacer may be chosen to provide a desired expanded height of an implant. A height of a spacer may be, for example, 2 mm, 3 mm, 4 mm, or greater. Spacer height may be chosen to achieve a desired height of an implant in a patient's spine. In some embodiments, a spacer with a variable thickness may be used to provide lordosis to an implant. In some embodiments, a spacer may be constructed of biocompatible metal (e.g., titanium). In certain embodiments, a spacer may be constructed of the same material as an implant into which the spacer is to be inserted. In other embodiments, a spacer may include elastomeric material (e.g., silicone) to absorb shock and/or allow additional bending.

Figure 19A:
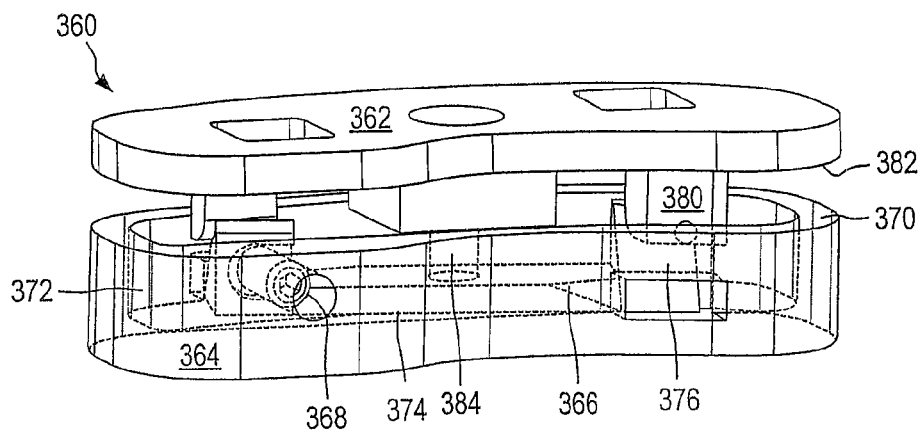
FIG. 19A is a perspective view of an embodiment of an expandable cage with an elongated insert.

FIG. 19A depicts a perspective view of an embodiment of an expandable implant with an elongated, rotating insert following expansion. Implant 360 may include upper body 362, lower body 364, insert 366, and advancing element 368. Intended placement of implant 360 in the spine may determine a shape of upper body 362 and lower body 364 (e.g., c-shaped, round). Superior surface 370 of lower body 364 may include recess 372. In some embodiments, recess 372 may be a channel. Insert 366 may be positioned in recess 372. Insert 366 may remain in recess 372 during insertion and expansion of implant 360. In some embodiments, inferior surface 374 of insert 366 may be substantially flat. Insert 366 may have an elongated shape with one or more angled portions 376 on superior surface 378 of the insert.

As advancing element 368 is advanced, angled portions 376 may engage extensions 450 of upper body 460. Advancement of advancing element 394 and rotation of insert 366 may increase a separation distance between upper body 460 and lower body 462.

Figure 19B:
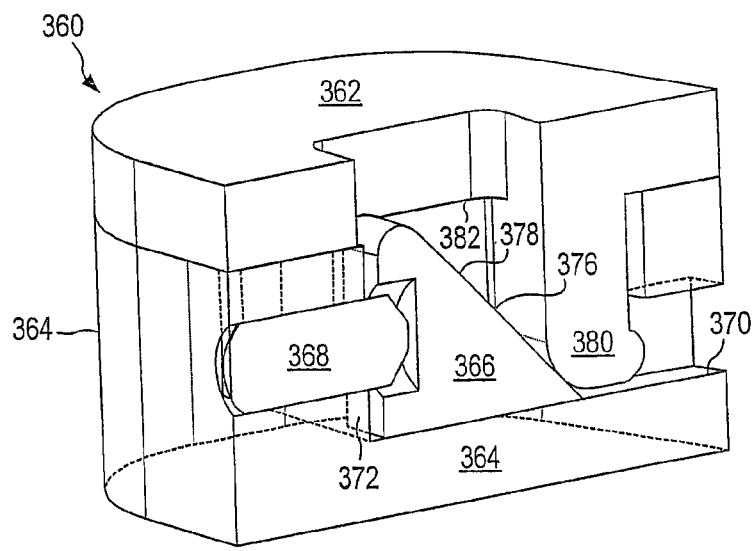
FIG. 19B is a cross-sectional view of the expandable cage embodiment depicted in FIG. 19A.

FIG. 19B depicts a cross-sectional view of implant 360 before expansion. During expansion, angled portions 376 on superior surface 378 of insert 366 may engage angled portions 380 extending downward from inferior surface 382 of upper body 362. As advancing element 368 is advanced into recess 372 in lower body 364, insert 366 rotates in recess 372 on superior surface 370 of lower body 364. In some embodiments, insert 366 remains in recess 372 and is not elevated during insertion and expansion of implant 360 in a human spine. As insert 366 is rotated, angled portions 380 of upper body 362 slide up the angled portions 376 of insert 366, and the upper body is elevated above lower body 364 to increase a height of implant 360 and/or to increase a separation distance between the upper body and the lower body. The elongated nature of insert 366 may result in a more stable expanded implant than an insert of a shorter length. As shown in FIG. 19B, angled portions 376 and/or angled portions 380 do not include a platform portion. Thus, implant 360 may have a variable expansion height. An expansion height of implant 360 may be secured with advancing element 368 or with a spacer of a desired height.

Figure 19C:
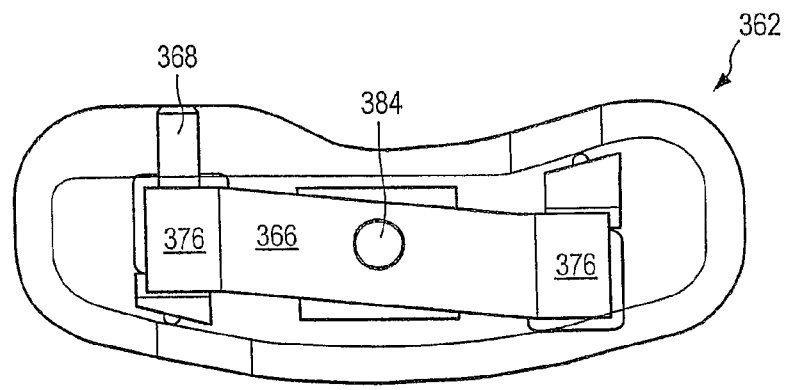
FIG. 19C is a view of the inferior surface of the upper body of the cage depicted in FIG. 19A.

FIG. 19C depicts a view of an inferior side of upper body 362 with insert 366 positioned on retaining post 384. Insert 366 may rotate around retaining post 384. In certain embodiments, retaining post 384 may limit a height of implant 360 and/or limit a separation distance between upper body 362 and lower body 364.

Figure 20A:
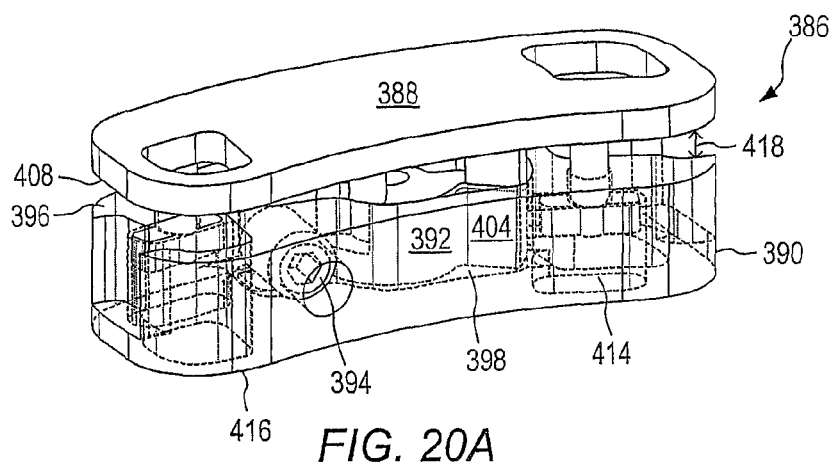
FIG. 20A is a perspective view of an embodiment of a cage including a cam and cam ramps.

FIG. 20A depicts a perspective view of an embodiment of a c-shaped expandable implant with a cam device. Implant 386 may include upper body 388, lower body 390, insert 392, and advancing element 394. In some embodiments, advancing element 394 may be an expansion member. In some embodiments, insert 392 may be a cam. As with all of the disclosed embodiments, the placement of implant 386 in the spine will determine a shape of upper body 388 and lower body 390. In some embodiments, lower body 390 may include recess 398 in superior surface 396. In certain embodiments, insert 392 may be positioned in recess 398.

Figure 20B:
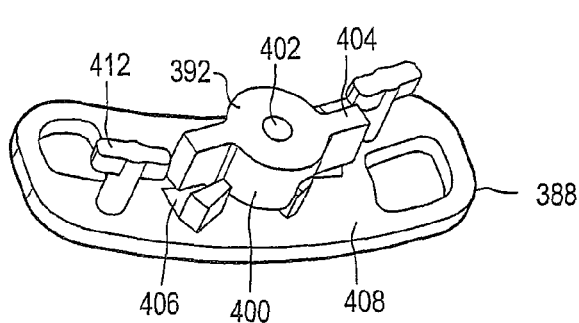
FIG. 20B is a view of the inferior surface of the upper body of the embodiment of the cage depicted in FIG. 20A.

In some embodiments, as shown in FIG. 20B, insert 392 may have a generally cylindrical central portion 400 with opening 402 defined therethrough. In certain embodiments, insert 392 may include one or more projections 404 extending radially from central portion 400. In some embodiments, projections 404 may be arms. Insert 392 may be positioned in recess 398 in lower body 390 on a projection (not shown) extending upward from a superior surface of the lower body such that the projection fits in opening 402 of central portion 400 of the insert. The projection may align and/or retain insert 392 in a desired position.

In some embodiments, upper body 388 may include one or more angled portions or cam ramps 406 that extend downward from inferior surface 408 of the upper body. In certain embodiments, cam ramps 406 may be positioned such that projections 404 of insert 392 engage the cam ramps as central portion 400 of the insert is rotated around the projection of lower body 390, increasing a separation distance between upper body 388 and lower body 390.

Figure 20C:
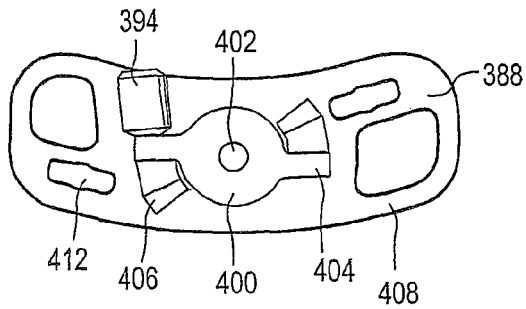
FIG. 20C illustrates the use of an advancing element to advance the cam onto the cam ramp of the cage embodiment depicted in FIG. 20B.

In certain embodiments, insert 392 may be rotated via the insertion of advancing element 394 (e.g., a screw), as shown in FIG. 20C. In some embodiments, stabilizers 412 may extend downward from inferior surface 408 of upper body 388 or upward from a superior surface of lower body 390. In some embodiments, stabilizers 412 may be, for example, retaining pegs. Stabilizers 412 may be of various shapes or sizes as required to limit separation of upper body 388 and lower body 390 as desired. When upper body 388 is placed over lower body 390, a large diameter portion (e.g., T-shaped, circular, ellipsoidal, rectangular) of stabilizers 412 may be held in openings 414 in lower body 390. In certain embodiments, stabilizers 412 may be inserted through inferior surface 416 of lower body 390 and then coupled (e.g., spot welded) to inferior surface 408 (e.g., openings in the inferior surface) of upper body 388.

As depicted in FIG. 20A, expansion of implant 386 may increase a separation distance between upper body 388 and lower body 390 to form gap 418 between the upper body and the lower body. The force of advancing element 394 on projections 404 of insert 392 may inhibit the insert from rotating after expansion, thus inhibiting implant 386 from undesirably returning to an unexpanded position. In some embodiments, a spacer may be placed in gap 418 between upper body 388 and lower body 390 to remove the force on advancing element 394 and to ensure that implant 386 remains in an expanded position.

Figure 20D:
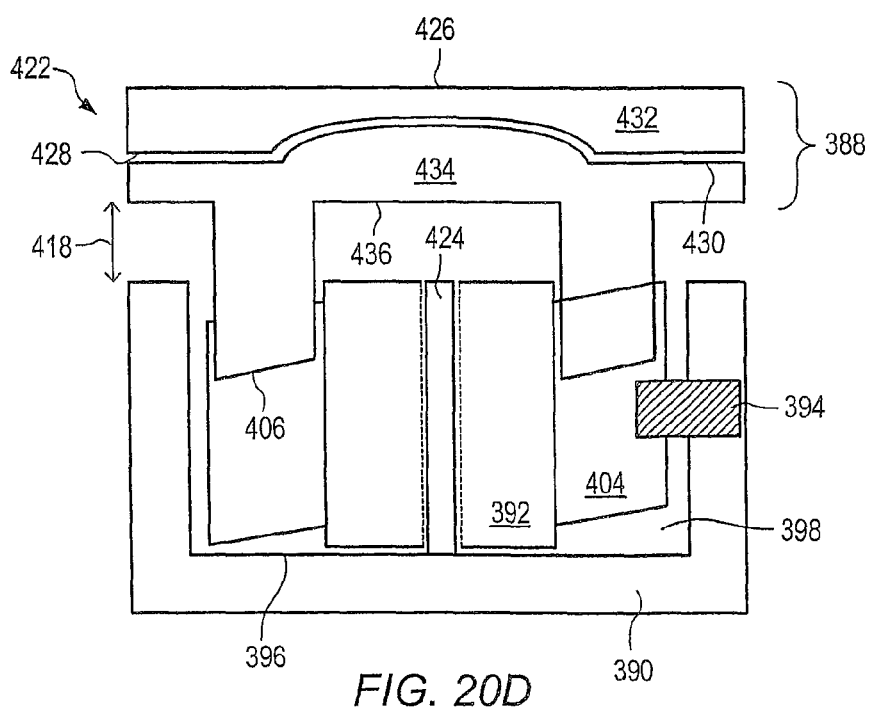
FIG. 20D is a cross-sectional view of an embodiment of an articulating cage including a cam and cam ramps.

The cam device employed in the embodiment illustrated in FIGS. 20A-C, as with all the disclosed embodiments of expandable implants, may also be employed in an articulating, or functional, implant. FIG. 20D depicts a cross-sectional view of an embodiment of an expandable, articulating implant with a cam insert. Insert 392 of implant 422 may be positioned in recess 398 of lower body 390. Projection 424 (e.g., a post) may extend upward from the superior surface of lower body 390. Insert 392 may rotate about projection 424.

Superior surface 426 of upper portion 432 of upper body 388 may contact the bony surface of an adjacent vertebral body after insertion. At least a portion of inferior surface 428 of upper portion 432 may be concave. At least a portion of superior surface 430 of lower portion 434 may be convex. A convex portion of lower portion 434 may be, for example, circular or ellipsoidal in shape. In some embodiments, a circular convex portion may allow biomechanical motion that mimics motion of the human spine. In certain embodiments, an ellipsoidal convex portion may allow translation as well as rotation between, for example, an upper portion and a lower portion of an upper body of an implant. In some embodiments, upper portion 432 and lower portion 434 of upper body 388 may articulate with respect to each other (e.g., may form a functional joint). In certain embodiments, cam ramps 406 may extend downward from inferior surface 436 of lower portion 434 into lower body 390. Advancing element 394 may push against projections 404 of insert 392, thereby rotating the insert and causing the projections to engage cam ramps 406. As projections 404 of insert 392 engage cam ramps 406 and the projections travel up the cam ramps, lower portion 434 and upper portion 432 of upper body 388 may be elevated with respect to lower body 390. As with the other disclosed embodiments, stabilizers (e.g., captive pegs) may also be employed to inhibit separation of upper body 388 from lower body 390.

After expansion of implant 422, gap 418 may exist between lower portion 434 of upper body 388 and lower body 390. A spacer (e.g., a shim) may be placed in gap 418 to inhibit implant 422 from returning to an unexpanded position. A spacer may be of various desirable shapes and/or sizes. For example, one side of a spacer may be thicker than another side of the spacer to achieve a desired lordotic angle of the implant. In some embodiments, implant 422 may be inserted in a spine upside down (e.g., upper body 388 oriented inferior to lower body 390) such that an axis of rotation of the implant is located closer to the inferior body after insertion.

Figure 21A:
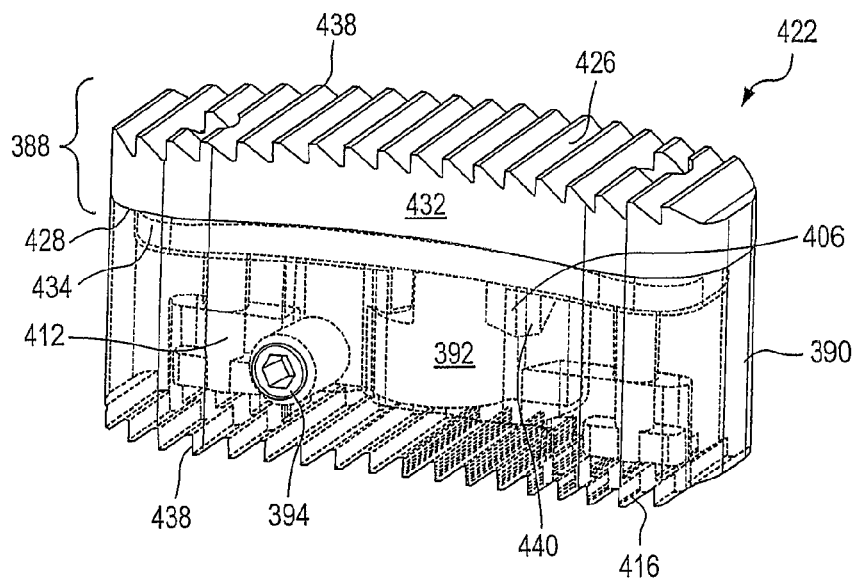
FIG. 21A depicts a perspective view of an embodiment of an expandable, articulating cage with toothed engaging surfaces.
Figure 21B:
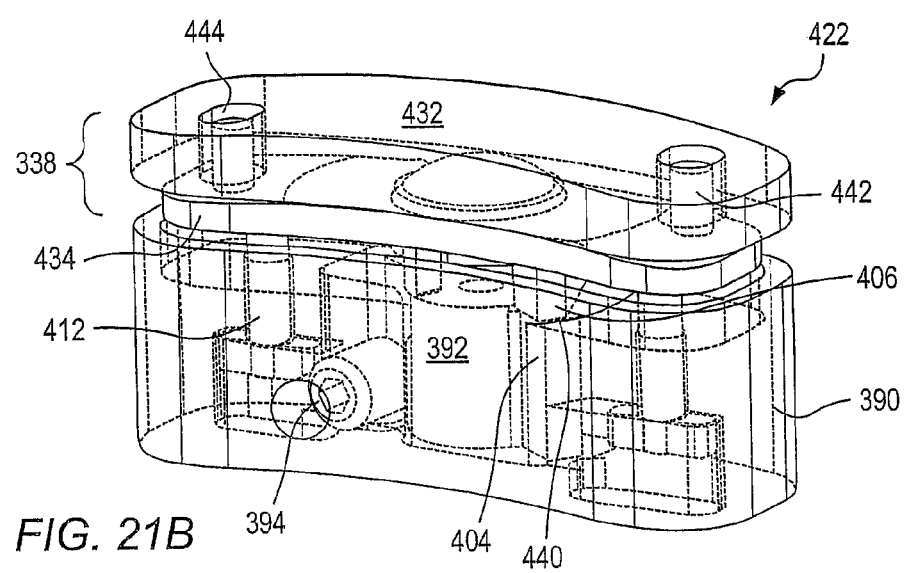
FIG. 21B depicts a perspective view of the cage depicted in FIG. 21A (without the toothed engaging surface) after expansion.

FIGS. 21A and 21B depict a perspective view of embodiments of c-shaped expandable, articulating implant 422 depicted in FIG. 20D. FIGS. 21A and 21B depict retention of stabilizers 412 in lower body 390. As shown in FIG. 21A, superior surface 426 of upper portion 432 of upper body 388 and inferior surface 416 of lower body 390 may include teeth 438. Teeth 438 may be of any regular or irregular desired size, shape, and/or spacing to promote retention of implant 422 between vertebrae after insertion. In some embodiments, teeth 438 may be randomly spaced protrusions or barbs. In certain embodiments, upper body 388 and/or lower body 390 may include openings to allow for bone ingrowth into an interior portion of implant 422.

FIG. 21A depicts implant 422 before expansion. In some embodiments, no visible gap may exist between upper body 388 (or upper portion 432) and lower body 390 of implant 422. Thus, a height of implant 422 before expansion may be a minimal height of the implant (e.g., the implant may not be able to articulate before expansion). In some embodiments, a visible gap may exist between upper body 388 (or upper portion 432) and lower body 390 of implant 422. Thus, a separation distance between upper body 388 (or upper portion 432) and lower body 390 of implant 422 may increase during expansion. FIG. 21B depicts fully expanded implant 422 (teeth are not shown for clarity) after advancement of advancing element 394. In some embodiments, advancing element 394 may be a screw (e.g., a set screw). In certain embodiments, advancing element 394 may be positioned on a side (e.g., posterior side) of implant 422 (e.g., for a TLIF application). In certain embodiments, advancing element 394 may be positioned on an end of implant 422 (e.g., for a PLIF application).

Implant 422 may be fully expanded when platform 440 of cam ramps 406 rests on a superior surface of insert 392 (e.g., on a superior surface of projections 404 of the insert). In some embodiments, articulation of upper portion 432 with lower portion 434 may be determined by a degree of convex curvature of inferior surface 428 of upper portion 432 and superior surface 430 of lower portion 434 and/or a relative height (and depth) of complementary convex/concave contacting surfaces of the upper portion and the lower portion. In certain embodiments, stabilizers 442 may be used to align upper portion 432 with lower portion 434 of upper body 388 and/or to retain the upper portion on the lower portion and/or to limit articulation between the upper portion and the lower portion. As depicted in FIG. 21B, stabilizers 442 may be coupled to lower portion 434 of upper body 388 and reside in openings 444 of upper portion 432. In some embodiments, stabilizers 442 may be coupled to upper portion 432.

Figure 22:
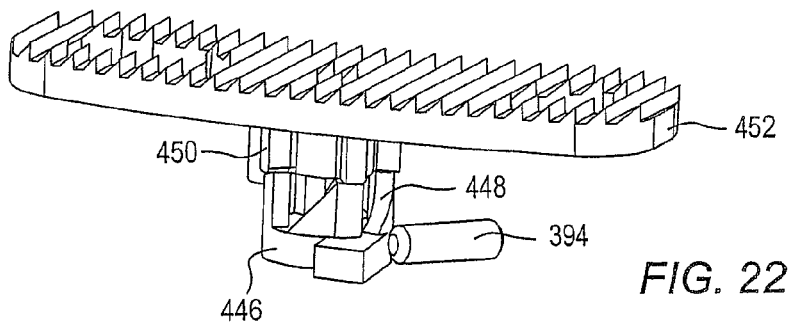
FIG. 22 depicts a perspective view of an embodiment of an insert with four cam ramps.

FIG. 22 depicts an embodiment of a portion of an expandable implant. In the embodiment depicted in FIG. 22, insert 446 includes four cam ramps 448. In other embodiments, an insert may include fewer (e.g., 2 or 3) or more (e.g., 5 to 12 or more) cam ramps. In contrast to the embodiment depicted in FIG. 21, in which the cam ramps are a part of the upper body of the implant and are stationary during expansion of the implant, cam ramps 448 may rotate as advancing element 394 rotates insert 446. In some embodiments, advancing element 394 may rotate insert 446 until an inferior surface of extensions 450 of upper body 452 rest on a superior surface (e.g., a platform) of cam ramps 448, as depicted in FIG. 22. Thus, the portion of the insert depicted in FIG. 22 may be used without a spacer to achieve a fixed separation distance between an upper body and a lower body of an implant. In some embodiments, a spacer may be used to provide extra stability and/or to reduce force exerted on cam ramps 448 of insert 446. In certain embodiments, a spacer may be used to achieve a separation distance less than the fixed separation distance determined by a cumulative height of cam ramps 448 and extensions 450 of upper body 452.

Figure 23:
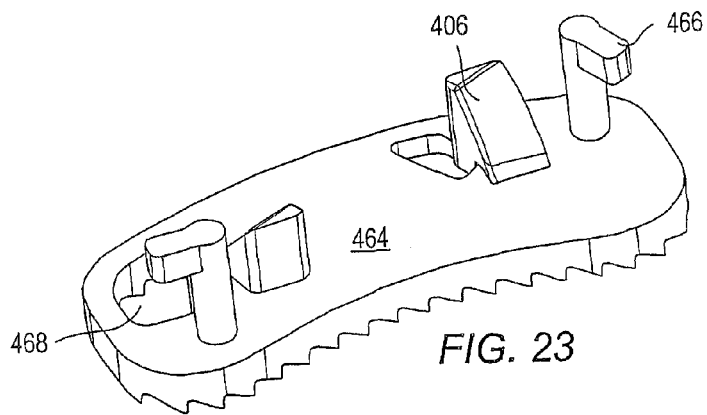
FIG. 23 depicts a perspective view of an embodiment of a portion of a cage with cam ramps and stabilizers.

In some embodiments, one or more cam ramps may be positioned on an inferior surface of an upper body or a superior surface of a lower body of an implant. FIG. 23 depicts an embodiment of an upper body of an implant. Upper body 464 may include cam ramps 406. Advancement of an insert up a curved and/or inclined surface of cam ramps 406 may determine an expansion height of an implant (e.g., a separation distance between an upper body and a lower body of the implant). Stabilizers 466 may allow upper body 464 and a lower body of the implant to remain coupled during and after expansion of the implant. In some embodiments, stabilizers 466 may limit a height of an implant and/or a separation distance between an upper body and a lower body of the implant. Opening 468 of upper body 464 may allow bone graft material to be packed inside the implant.

Figure 24A:
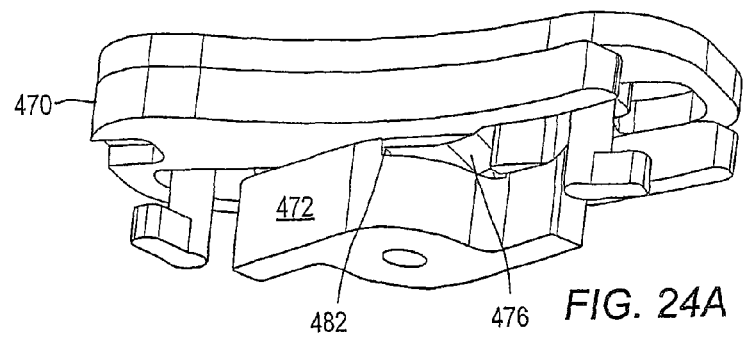
FIG. 24A depicts a perspective view of an embodiment of a spacer coupled to an insert of an implant.
Figure 24B:
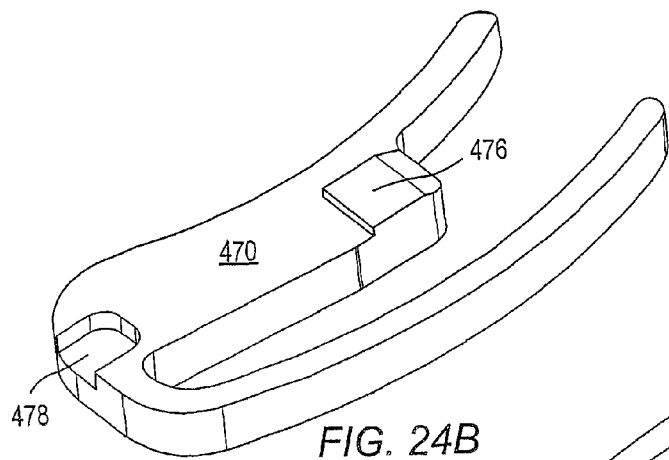
FIG. 24B depicts a perspective view of an embodiment of a spacer with a protrusion.
Figure 24C:
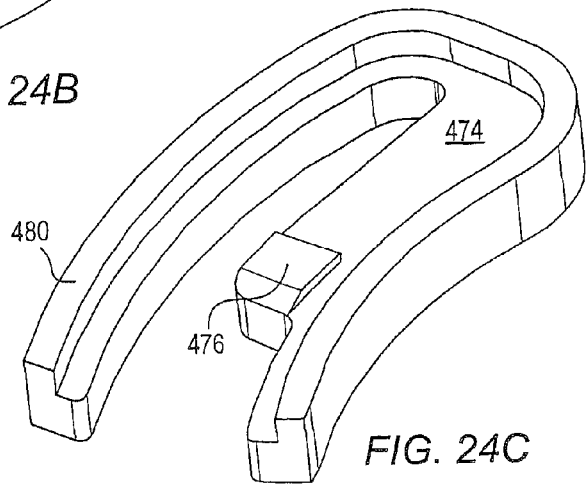
FIG. 24C depicts a perspective view of an embodiment of a spacer with a protrusion and a lip.

In some embodiments, a spacer and an insert may include complementary portions that allow a spacer to be coupled to an implant (e.g., reversibly or irreversibly locked into place between an upper body and a lower body of the implant). FIG. 24A depicts a perspective view of an embodiment of spacer 470 coupled to insert 472. FIG. 24B depicts a perspective view of spacer 470. FIG. 24C depicts a perspective view of another spacer 474. Spacers 470, 474 may include protrusion 476. In some embodiments, protrusion 476 of spacers 470, 474 may be press fit or loose fit into a recess of a member of an implant (e.g., an insert). Fitting (e.g., snapping) protrusion 476 into a recess may advantageously provide a tactile indication to a surgeon that spacer 470, 474 is properly placed and secured in an implant.

Spacers may have various features designed to facilitate insertion in an implant, retention in an implant, and/or removal from an implant. For example, spacer 470 shown in FIG. 24B may include recess 478. Recess 478 may allow spacer 470 to be grasped for insertion in an implant and/or for removal from an implant. Spacer 474 shown in FIG. 24C may include lip 480. Lip 480 may facilitate (e.g., guide) insertion of spacer 474 into a gap in an implant. In some embodiments, lip 480 may promote retention of spacer 474 in a gap between an upper body and a lower body of an implant. In some embodiments, a spacer may include a lip around a superior and/or inferior surface of the entire spacer. In certain embodiments, a spacer may include a lip around a superior and/or inferior surface of a portion (e.g., one side) of a spacer. In some embodiments, a lip may be an external lip or an internal lip. In certain embodiments, a lip on an inferior surface of an upper body or a superior surface of a lower body of an implant may be used together with or instead of a lip on a spacer.

Figure 24D:
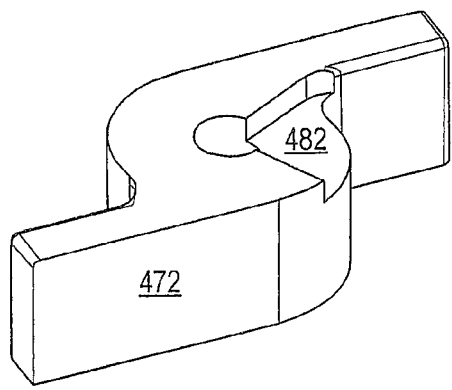
FIG. 24D depicts a perspective view of an embodiment of an insert with a recess for accepting a protrusion of a spacer.
Figure 24E:
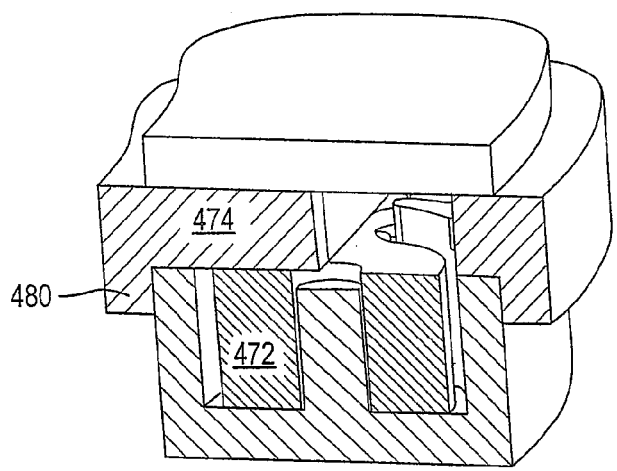
FIG. 24E depicts a cross-sectional view of an embodiment of a spacer with a lip coupled to an insert in an expandable cage.

FIG. 24D depicts a perspective view of an embodiment of an insert. Insert 472 may include recess 482. Recess 482 may be complementary to a protrusion of a spacer (e.g., protrusion 476 of spacers 470, 474). As depicted in FIG. 24A, protrusion 476 of spacer 470 may fit securely in recess 482 of insert 472, inhibiting backout of the spacer after the spacer has been fully inserted. FIG. 24E depicts a perspective cross-sectional view of spacer 474 with lip 480 used to maintain a separation distance between insert 472 and an upper body of an implant.

Figure 25:
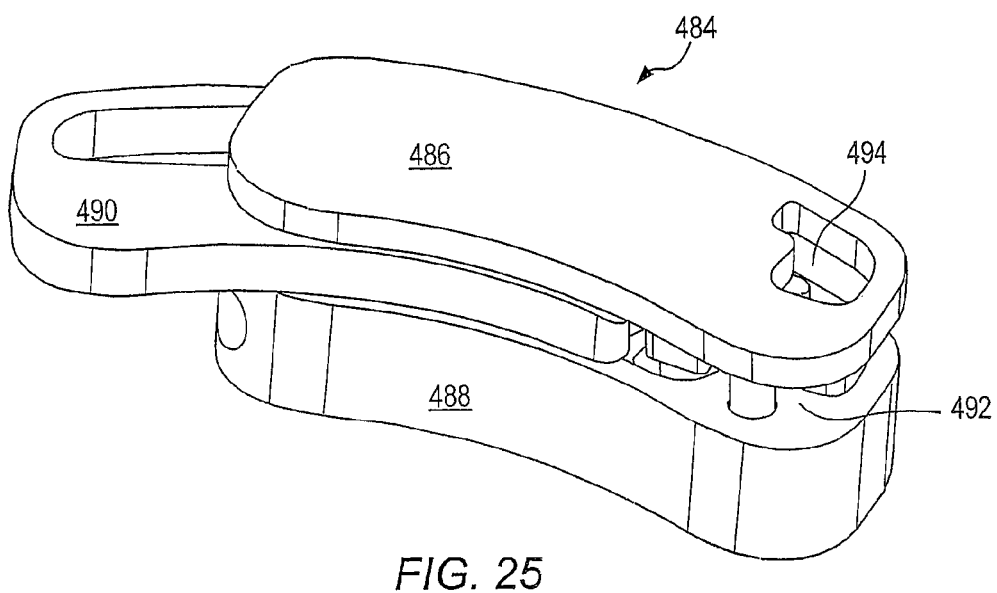
FIG. 25 depicts a perspective view of an embodiment of insertion of a spacer into an expanded cage.

FIG. 25 depicts a perspective view of an embodiment of an expanded c-shaped implant during insertion of a spacer. Implant 484 may include upper body 486 and lower body 488. Spacer 490 may be inserted in gap 492 between upper body 486 and lower body 488. Opening 494 in upper body 486 may allow bone graft material to be packed inside implant 484.

Figure 26A:
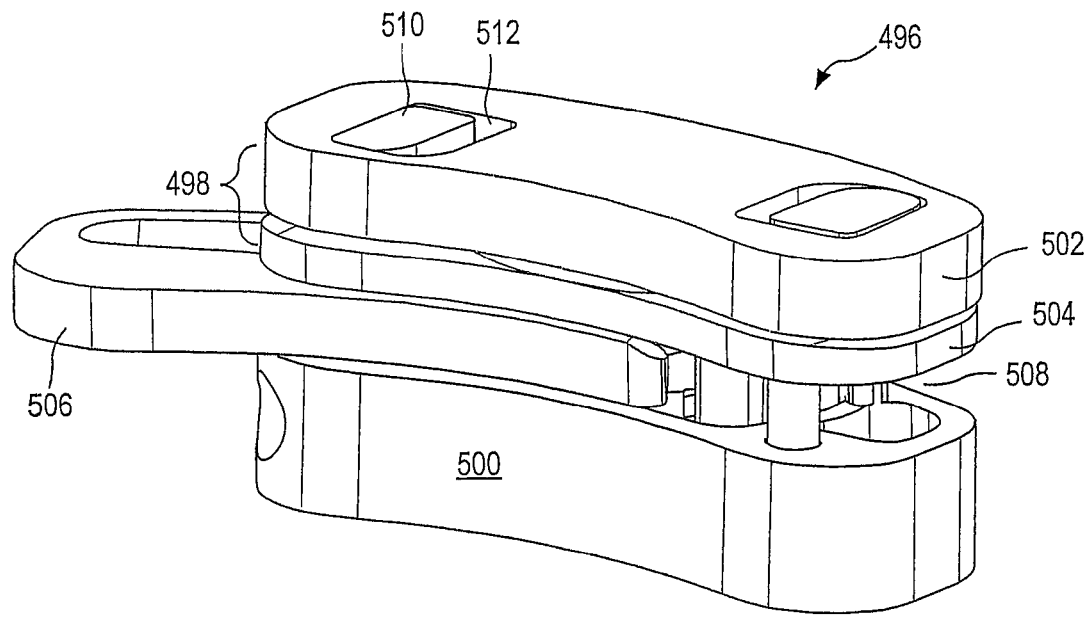
FIG. 26A depicts a perspective view of an embodiment of insertion of a spacer into an expanded cage.

FIG. 26A depicts a perspective view of an embodiment of an expanded c-shaped articulating implant during insertion of a spacer. Implant 496 may include upper body 498 and lower body 500. Upper body 498 may include upper portion 502 and lower portion 504. Spacer 506 may be inserted in gap 508 between lower body 500 and lower portion 504 of upper body 498. In some embodiments, stabilizers 510 may extend from lower portion 504 through openings 512 in upper portion 502 of upper body 498. A size and/or shape of stabilizers 510 and/or openings 512 may allow a desired amount of articulation between upper portion 502 and lower portion 504 of upper body 498 (e.g., about a convex portion of the superior surface of lower portion).

Figure 26B:
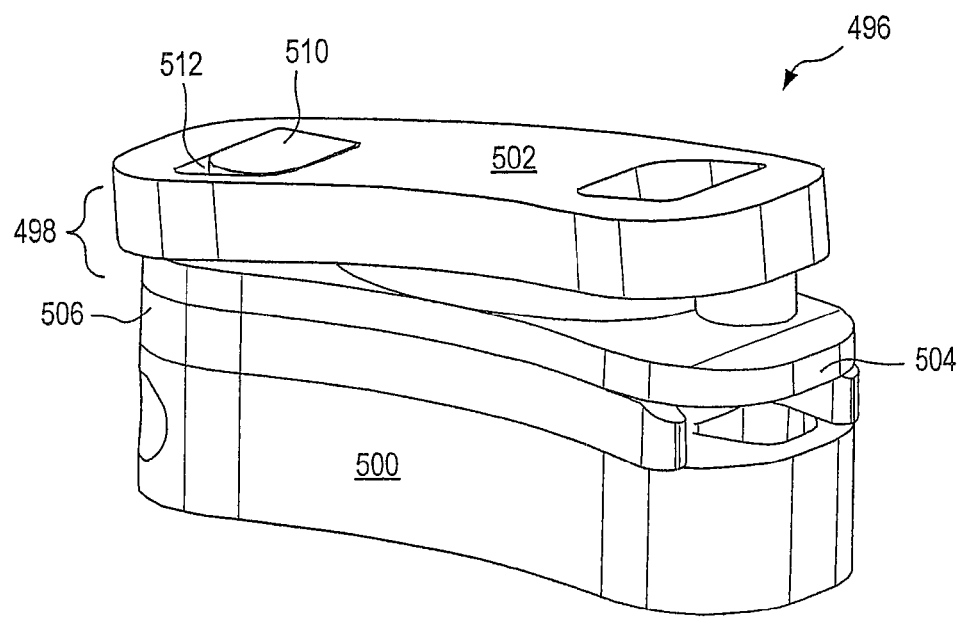
FIG. 26B depicts a perspective view of an embodiment of the cage depicted in FIG. 26A after insertion of the spacer.
Figure 26C:
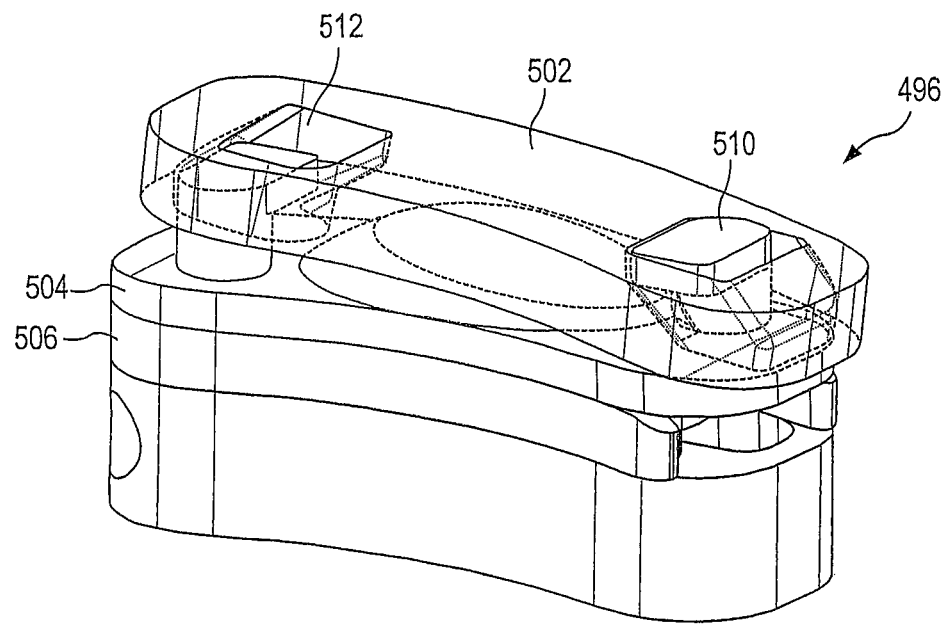
FIG. 26C depicts a perspective view of an embodiment of the cage depicted in FIG. 26A after insertion of the spacer.

FIGS. 26B and 26C depict perspective views of implant 496 after spacer 506 has been fully inserted. FIG. 26B depicts implant 496 with upper portion 502 angled relative to lower portion 504 of upper body 498. Superior surface of lower portion 504 may include a convex portion (e.g., substantially ellipsoidal or round) that articulates with a concave portion of inferior surface of upper portion 502 to allow translation, rotation, anterior/posterior bending, and/or lateral bending of upper portion 502 relative to lower portion 504 of upper body 498, subject to size, shape, and orientation of stabilizers 510 and openings 512. FIG. 26C depicts implant 496, with details of stabilizers 510 and openings 512 visible. Stabilizers 510 may be shaped and oriented such that upper portion 502 is angled onto lower portion 504 during assembly of implant 496. Angled portions of stabilizers 510 and openings 512 may allow desired ranges of translational and/or rotational motion of upper portion 502 relative to lower portion 504 while inhibiting separation of the upper portion from the lower portion.

Figure 27:
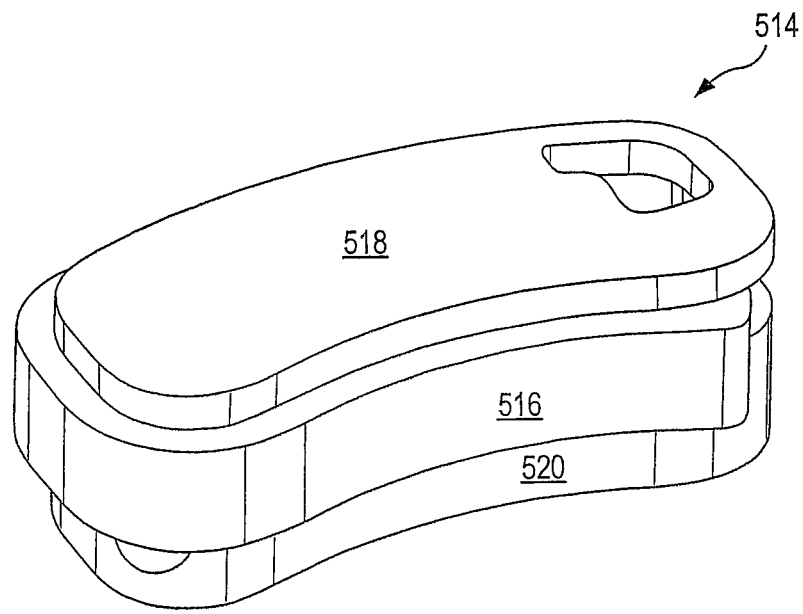
FIG. 27 depicts a perspective view of an embodiment of an expanded cage with a large profile spacer.

FIG. 27 depicts a perspective view of an embodiment of a c-shaped expandable implant with a spacer. Implant 514 may include spacer 516 between upper body 518 and lower body 520. Spacer 516 may have a larger profile than upper body 518 and lower body 520 of implant 514. Thus, a portion of spacer 516 may protrude from a circumference of implant 514. A spacer with a larger profile than an upper body and/or lower body of an implant may provide torsional support and/or facilitate insertion of the spacer during a surgical procedure.

Figure 28A:
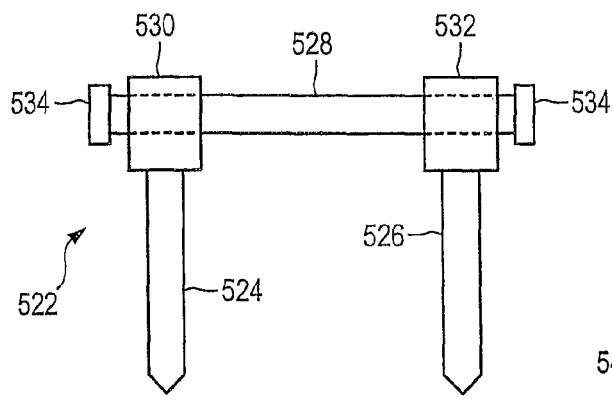
FIG. 28A is a side view of an embodiment of a facet replacement device, featuring a rod with two washer-type heads.

FIG. 28A depicts a side view of an embodiment of a facet replacement device. Facet replacement device 522 may include upper pedicle screw 524 and lower pedicle screw 526. Rod 528 may be retained in head 530 of upper pedicle screw 524 and head 532 of lower pedicle screw 526. Rod 528 may have washer-type ends 534 that allow for posterior compression, but not extension.

Figure 28B:
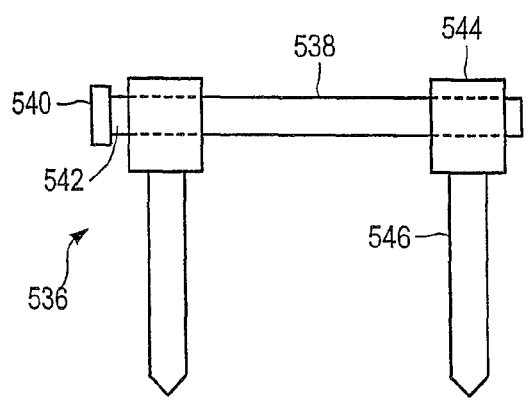
FIG. 28B is a side view of an embodiment of a portion of a facet replacement device, featuring a rod with a single washer-type head.
Figure 28C:
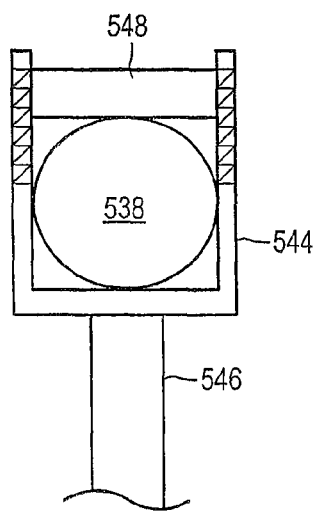
FIG. 28C is a cross-sectional view of an embodiment of a pedicle screw featuring a locking screw head.

FIG. 28B depicts a side view of an embodiment of a facet replacement device. Facet replacement device 536 may include rod 538. Rod 538 may include a single washer-type end 540 on lower end 542. Head 544 of upper pedicle screw 546 may have threaded locking screw 548, as shown in the cross section in FIG. 28C. Threaded locking screw 548 may hold rod 538 in place and inhibit head 544 of pedicle screw 546 from swiveling while allowing rod 538 to rotate and translate through the head of the pedicle screw.

Figure 28D:
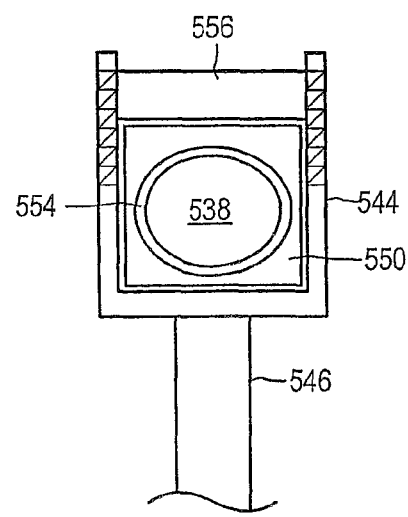
FIG. 28D is a cross-sectional view of an embodiment of a pedicle screw featuring a head-locking insert that allows translation and rotation of a rod.

FIG. 28D depicts a cross-sectional view of an embodiment of a head-locking insert that may be used in conjunction with a pedicle screw having a locking-type head. In some embodiments, insert 550 may have a similar shape to head 544 of pedicle screw 546. Insert 550 may be of solid construction, with opening 554 defined therethrough. In some embodiments, opening 554 may substantially align with the opening defined through head 544 of pedicle screw 546. As set screw 556 is engaged into head 544 of pedicle screw 546, force is applied to the top of insert 550 and is transferred to the bottom of the head. The force locks head 544 of pedicle screw 546, as with conventional locking pedicle screws; however, the force is not transferred to rod 538. With no force transferred to rod 538, the rod may rotate in and translate through head 544 of the pedicle screw. Alternatively, a shorter insert 550 (e.g., threaded only part way into head 544) may be used to inhibit a transfer of force to the bottom of the head such that the pedicle screw head undergoes multi-axial motion while retaining the rod in the head.

Figure 29A:
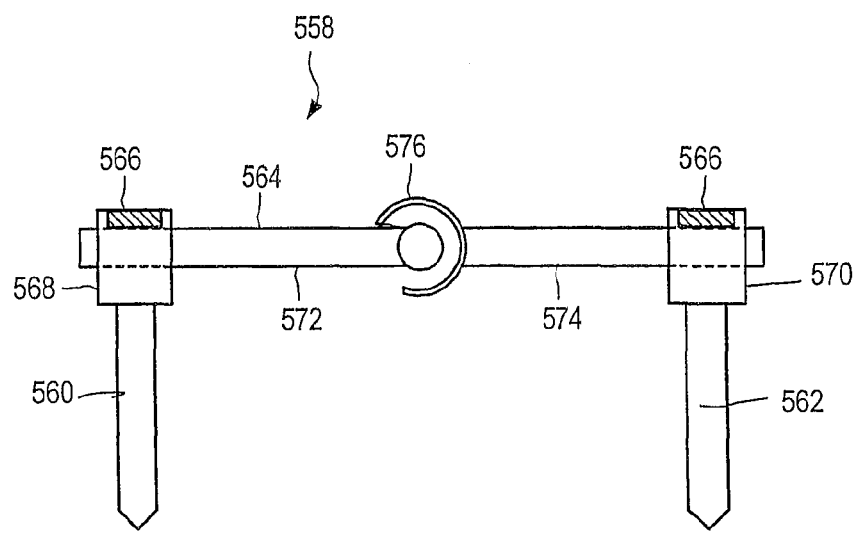
FIG. 29A is a side view of an embodiment of a portion of a facet replacement device, featuring a rod having a ball joint.

FIG. 29A depicts a side view of an embodiment of a facet replacement device. Facet replacement device 558 may include upper pedicle screw 560 and lower pedicle screw 562. Rod 564 may be retained within heads of pedicle screws 560, 562. Both pedicle screws 560, 562 may be secured with locking screws 566 that inhibit heads 568, 570 of the pedicle screws from swiveling while allowing rotation and/or translation of rod 564. Rod 564 may include rod members 572, 574 coupled via ball joint 576. Ball joint 576 may allow for a generally upward rotation, away from the bony surfaces of the vertebrae to which pedicle screws 560, 562 are secured, but inhibit a generally downward rotation, which would bring the ball joint in contact with the vertebrae to which the pedicle screws are secured.

Figure 29B:
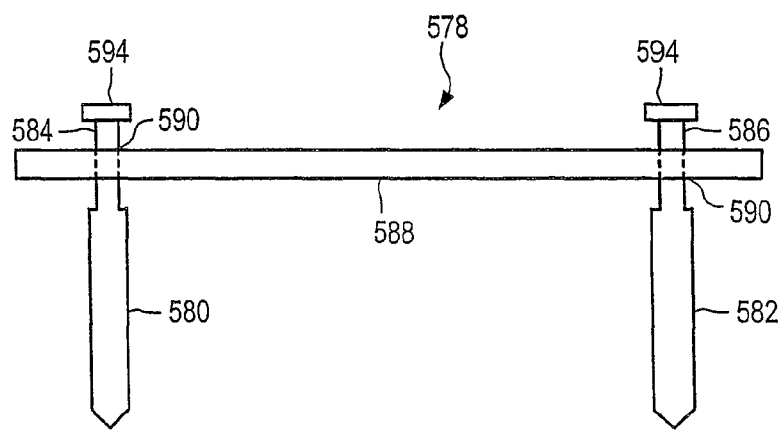
FIG. 29B is a side view of an embodiment of a portion of a facet replacement device featuring a retaining plate.
Figure 29C:
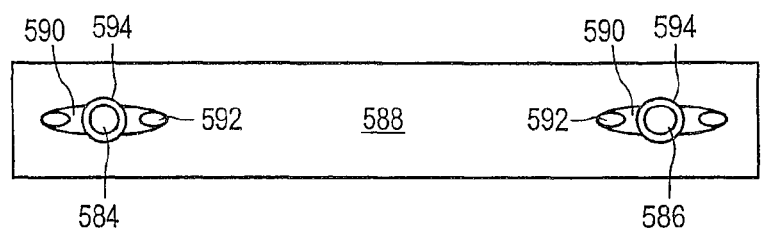
FIG. 29C is a top view of an embodiment of a portion of a facet replacement device featuring a retaining plate.

FIGS. 29B and 29C depict side and top views, respectively, of an embodiment of a facet replacement device. Facet replacement device 578 may include upper pedicle screw 580 and lower pedicle screw 582 having post-type heads 584, 586. Rather than the previously described rod, retaining plate 588 may be included. Elongated openings 590 may be defined through retaining plate 588 positioned on the post-type heads 584, 586 of pedicle screws 580, 582. Post-type heads 584, 586 may be allowed to move in elongated openings 590, providing a limited range of motion. Employing cushioning pads 592 made of rubber or other elastomeric biocompatible material may dampen movement of retaining plate 588. Post-type heads 584, 586 may also include threaded or lockable caps 594 to inhibit dislocation of retaining plate 588 from the post-type heads.

Figure 29D:
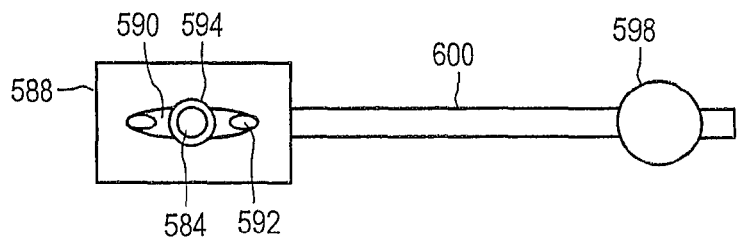
FIG. 29D is a top view of an embodiment of a portion of a facet replacement device featuring a combination multi-axial pedicle screw and retaining bar with post-type pedicle screw system.

FIG. 29D illustrates a pedicle screw having post-type head 584 used in conjunction with a pedicle screw having a locking or non-locking type head 598. Retaining plate 588 may be formed with rod 600 on one end, which may be slidingly positioned through pedicle screw head 598.

Figure 29E:
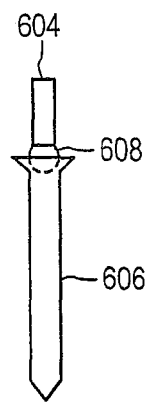
FIG. 29E is a side view of an embodiment of a post-type pedicle screw.
Figure 29F:
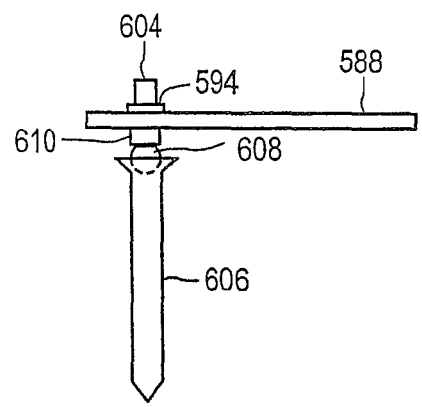
FIG. 29F illustrates attachment of the retaining bar to the post-type pedicle screw.

As shown in FIGS. 29E and 29F, post-type heads 604 of pedicle screws 606 used in conjunction with retaining plate 588 may also exhibit multi-axial motion. Post-type head 604 may be coupled to pedicle screw 606 with ball joint 608. FIG. 29F shows spacer 610 disposed below retaining plate 588. Spacer 610 may allow for rotation of ball joint 608.

Figure 30:
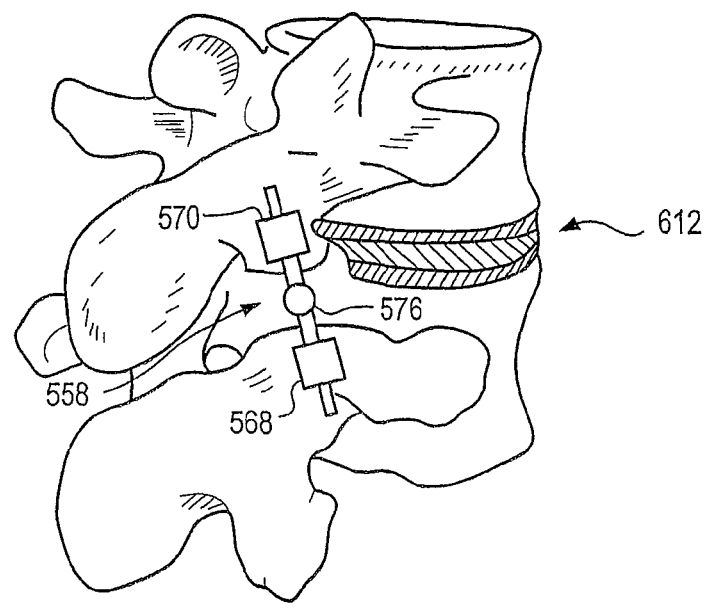
FIG. 30 is a posterior view of a portion of a human spine after reconstruction and implantation of an embodiment of an artificial functional spinal unit including an expandable implant and a facet replacement device.

FIG. 30 depicts facet replacement device 558 of FIG. 29A in place on the spinal column. Note that implant 612 has been posteriorly placed within the intervertebral space through the void created by the surgical removal of the natural facet joint. In addition, ball joint 576 may rotate in the posterior (upward) direction during posterior compression to inhibit impact upon the bony surfaces of the spine.

Figure 31A:
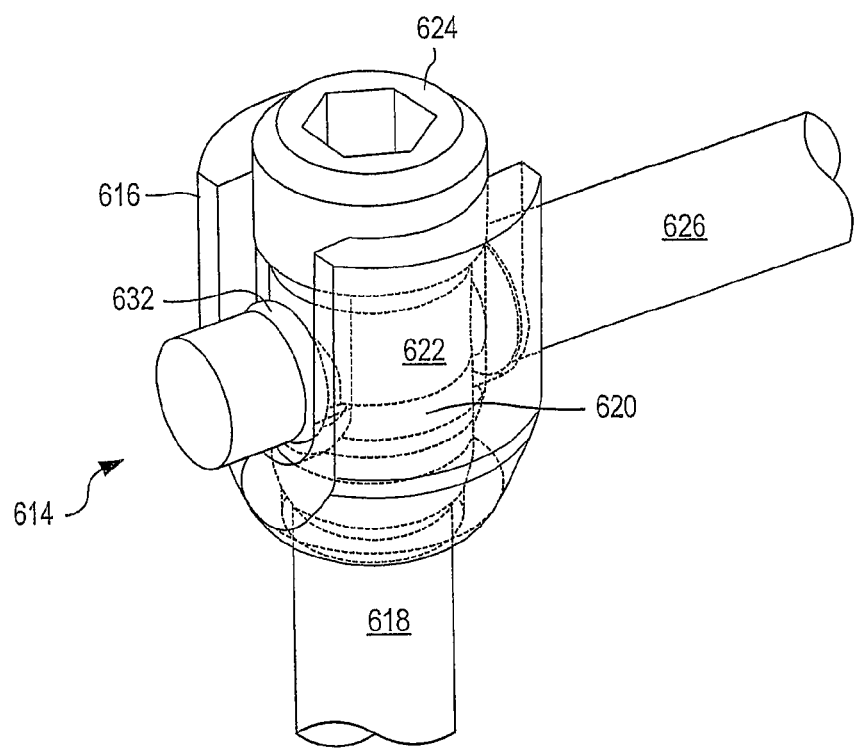
FIG. 31A is a perspective view of an embodiment of a portion of a facet replacement device.
Figure 31B:
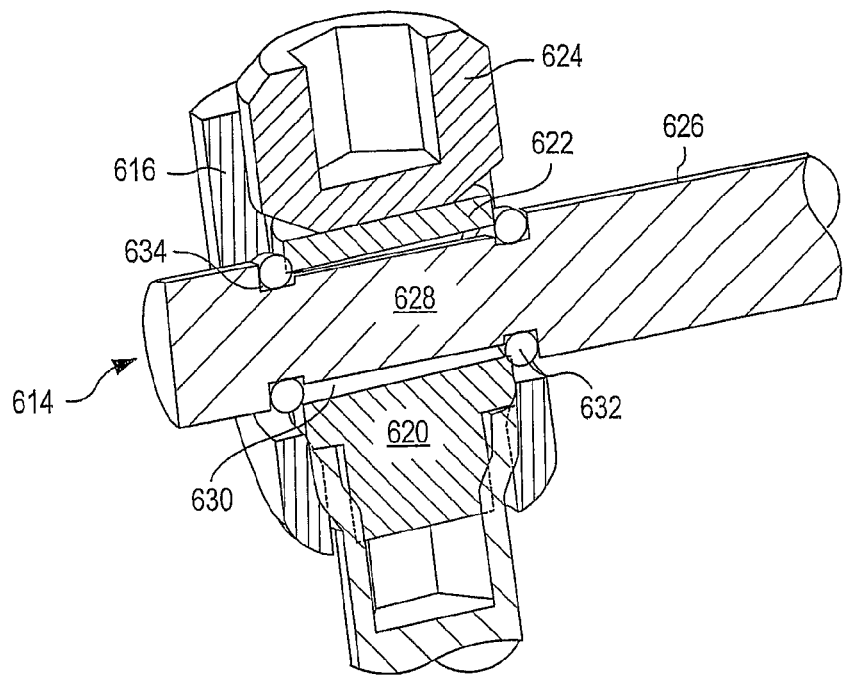
FIG. 31B is a cross-sectional view of the facet replacement device depicted in FIG. 31A.

FIG. 31A depicts a perspective view of a portion of an embodiment of a facet replacement device. Facet replacement device 614 may include pedicle screw head 616, pedicle screw 618, lower saddle 620, upper saddle 622, and set screw 624. Rod 626 may be positioned between lower saddle 620 and upper saddle 622. Set screw 624 may secure lower saddle 620, upper saddle 622, and rod 626 in pedicle screw head 616 of facet replacement device 614. In some embodiments, a diameter of a portion of rod 626 held between lower saddle 620 and upper saddle 622 may substantially the same diameter as other portions of the rod. For example, rod 626 may be of substantially constant diameter. In certain embodiments, a portion of rod 626 held between lower saddle 620 and upper saddle 622 may be reduced in diameter relative to other portions of the rod. FIG. 31B depicts a cross-sectional view of reduced diameter portion 628 of rod 626 positioned in pedicle screw head 616 of facet replacement device 614.

Figure 31C:
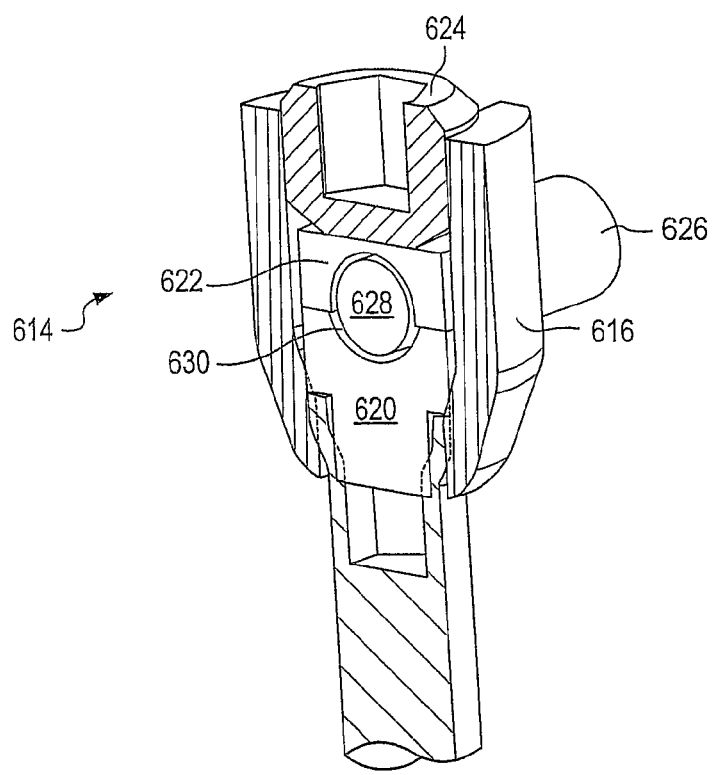
FIG. 31C is a cross-sectional view of the facet replacement device depicted in FIG. 31A.
Figure 31D:
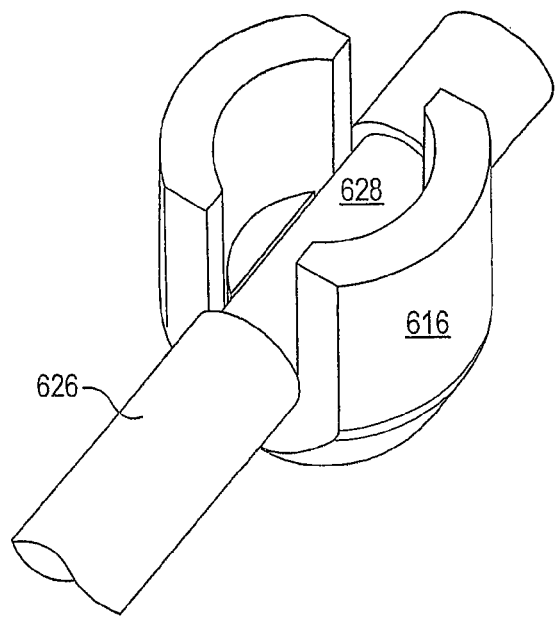
FIG. 31D is a perspective view of an embodiment of a reduced diameter portion of a rod resting in a pedicle screw head of a facet replacement device.

FIGS. 31B and 31C depict perspective cross-sectional views of facet replacement device 614. As shown in FIGS. 31B and 31C, rod 626 may have reduced diameter portion 628 positioned between lower saddle 620 and upper saddle 622. Reduced diameter portion 628 of rod 626 may be secured in opening 630 formed by lower saddle 620 and upper saddle 622. Rod 626 may be retained in a desired position between lower saddle 620 and upper saddle 622 by O-rings 632. As depicted in FIG. 31B, O-rings 632 may reside in grooves 634 in rod 626. A position of grooves 634 in rod 626 may be chosen to allow translation of the rod through opening 630 with O-rings 632 positioned in grooves 634. O-rings 632 may be made of any biocompatible elastomeric material including, but not limited to, silicone. Grooves 634 may have any desirable cross-sectional shape including, but not limited to, rectangular, square, arcuate, or v-shaped.

As depicted in FIGS. 31B and 31C, opening 630 formed by lower saddle 620 and upper saddle 622 may have a diameter that exceeds a diameter of the portion of rod 626 (e.g., reduced diameter portion 628 held between the upper saddle and the lower saddle. With a diameter of opening 630 that exceeds a diameter of rod 626 held in the opening, the rod may be able to move relative to pedicle screw head 616 of facet replacement device 614. In some embodiments, rod 626 may be able to translate and/or rotate with respect to pedicle screw head 616. In certain embodiments, rod 626 may be able to rotate about axes parallel and/or perpendicular to a longitudinal axis of the rod. As depicted in FIG. 31B, rotation of rod 626 about an axis perpendicular to a longitudinal axis of the rod may result in tilting or angulation of the rod relative to pedicle screw head 616. In some embodiments, movement of rod 626 in opening 630 may be cushioned by O-rings 632.

Figure 32:
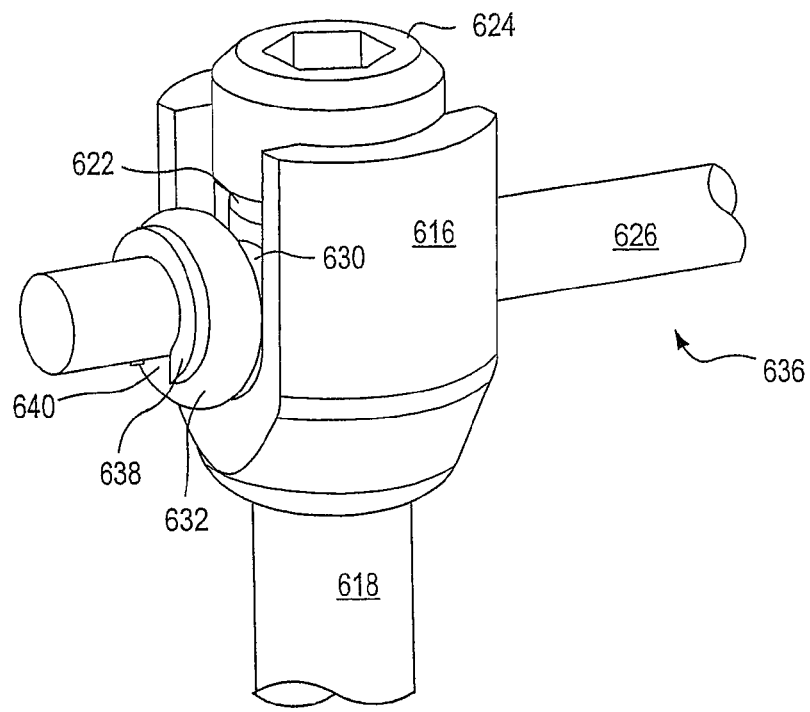
FIG. 32 is a perspective view of an embodiment of a portion of a facet replacement device with a retainer to limit the motion of a rod.

FIG. 32 depicts a perspective view of a portion of an embodiment of a facet replacement device that may be used in a 2-level spinal stabilization procedure. Facet replacement device 636 may include pedicle screw head 616, pedicle screw 618, lower saddle (not shown), upper saddle 622, and set screw 624. Retainer 638 may hold rod 626 in opening 630 formed by the lower saddle and upper saddle 622. Opening 630 may be sized as noted with respect to facet replacement device 614 (FIG. 31) to allow rotational and/or translational motion of rod 626 in the opening. O-ring 632 may cushion movement of rod 626 in opening 630. Rod 626 used with facet replacement device 636 may have a substantially uniform diameter. That is, facet replacement device 636 does not require a portion of rod 626 to have a reduced diameter. Therefore, pedicle screw head 616 may be placed at any desired position along a length of rod 626. Adjustable positioning of pedicle screw head 616 along a length of a rod of uniform diameter may allow the use of the facet replacement device 636 in a two-level or multi-level spinal stabilization procedure.

Retainer 638 may be a c-shaped element with opening 640. A diameter of rod 626 may exceed a length of opening 640. Thus, after retainer 638 has been snapped onto rod 626, the retainer may remain securely on the rod. Rotational motion of rod 626 in opening 630 may be limited by relative diameters of rod 626 and opening 630. Translational motion of rod 626 through opening 630 may be limited by placement of retainers 638 on either side of pedicle screw head 616.

Figure 33A:
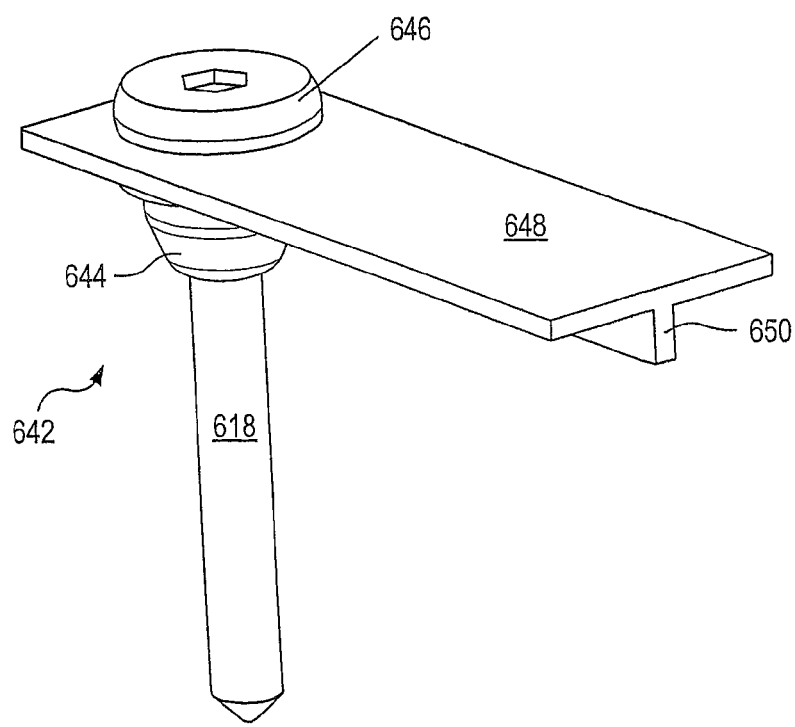
FIG. 33A is a perspective view of an embodiment of a portion of a facet replacement device designed to couple to a plate with a T-shaped cross section.

FIG. 33A depicts a perspective view of an embodiment of a portion of a facet replacement device including a plate rather than a rod. Facet replacement device 642 may include pedicle screw 618, pedicle screw head 644, and fastener 646. In some embodiments, fastener 646 may be, for example, a screw. Plate 648 may be coupled between pedicle screw head 644 and fastener 646. In some embodiments, plate 648 may have a T-shaped cross section. In certain embodiments, a T-shaped cross section may provide a lower profile than a rod, advantageously requiring less space at a surgical site. Size, thickness, and dimensions of a T-shaped cross section may vary as needed for strength, stability, and surgical access. For example, stem portion 650 of plate 648 may be of various heights.

Figure 33B:
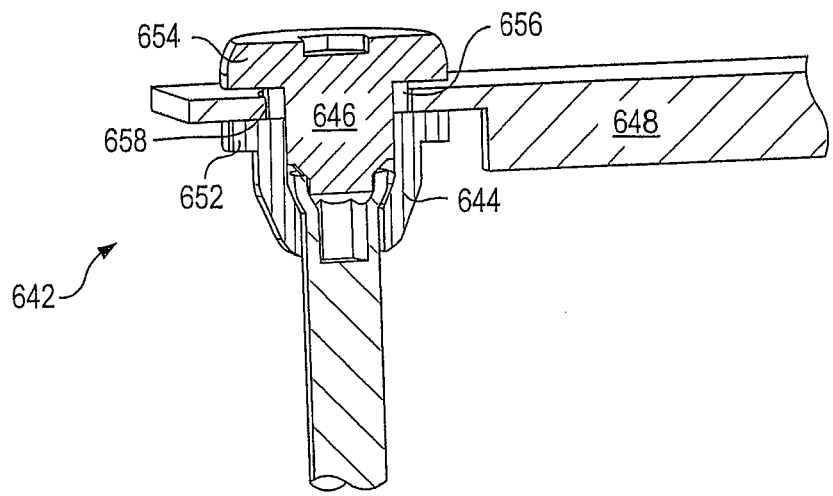
FIG. 33B is a cross-sectional view of the facet replacement device depicted in FIG. 33A.

FIG. 33B depicts a cross-sectional view of facet replacement device 642 including plate 648. Plate 648 may be coupled to pedicle screw head 644 between lip 652 of the pedicle screw head and lip 654 of fastener 646. In some embodiments, fastener 646 may have a threaded portion that engages a threaded portion inside pedicle screw head 644 (threaded portions not shown). In some embodiments, spacer 656 may be positioned between pedicle screw head 644 and fastener 646. In certain embodiments, spacer 656 may fit inside opening 658 in plate 648 (e.g., between the plate and fastener 646). A diameter of opening 658 may be sized such that plate 648 can rotate and/or translate relative to pedicle screw head 644. In some embodiments, spacer 656 may be a bushing or an O-ring. Spacer 656 may be made of elastomeric materials such as, but not limited to, silicone. Spacer 656 may cushion and/or dampen movement of plate 648 relative to pedicle screw head 644 and/or fastener 646 to allow smoother biomechanical motion after insertion in a human spine.

Figure 34A:
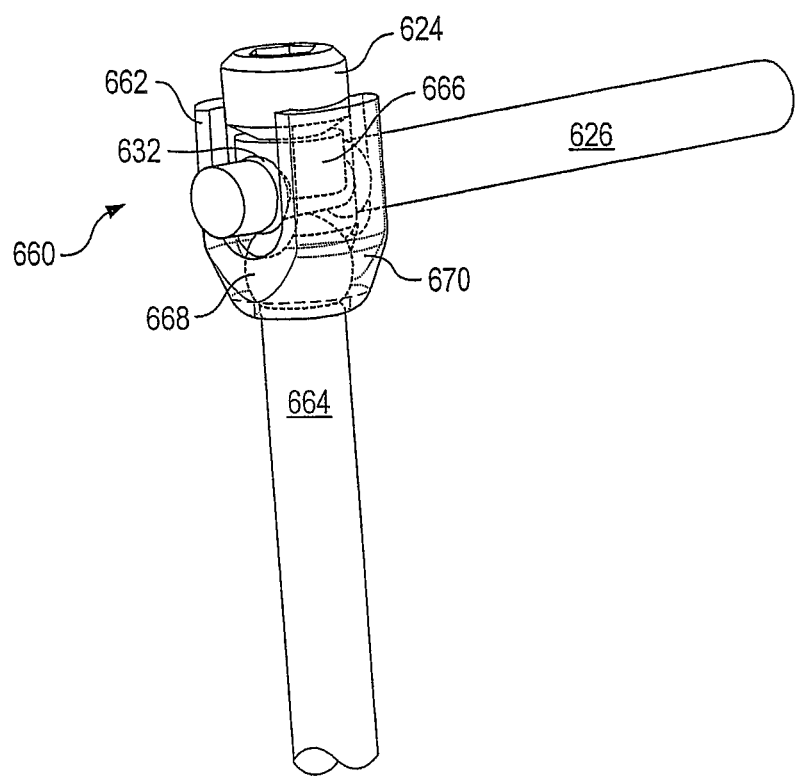
FIG. 34A is a perspective view of an embodiment of a portion of a facet replacement device including a pedicle screw with a ball joint.

FIG. 34A depicts a perspective view of an embodiment of a portion of a facet replacement device with a pedicle screw that retains mobility after a rod is secured. Facet replacement device 660 may include pedicle screw head 662, pedicle screw 664, upper saddle 666, and set screw 624. Ball joint 668 of pedicle screw 664 may rest in base 670 of pedicle screw head 662. A portion of rod 626 may contact ball joint 668 of pedicle screw 664. In some embodiments, rod 626 may have a reduced diameter portion that resides in pedicle screw head 662 and contacts ball joint 668 of pedicle screw 664. In other embodiments, rod 626 may have a substantially constant diameter.

In some embodiments, an outside portion of upper saddle 666 and an inside portion of pedicle screw head 662 may be complementarily threaded (not shown), such that the upper saddle may be threaded into the head. In certain embodiments, pedicle screw head 662 may be threaded such that upper saddle 666 may be threaded a limited distance into the head (e.g., upper saddle 666 does not contact base 670). Set screw 624 may inhibit backout of upper saddle 666 from pedicle screw head 662. A length of threading in pedicle screw head 662 may be chosen such that upper saddle 666 may be fully secured in the head without tightening rod 626 onto ball joint 668. Thus, with rod 626 fully secured in head 662, the rod and pedicle screw 664 both retain rotational mobility. In some embodiments, O-rings 632 may be positioned on rod 626 on both sides of upper saddle 666. Translation of rod 626 in pedicle screw head 662 may be limited by the placement of O-rings 632 on the rod and/or by a retainer.

Figure 34B:
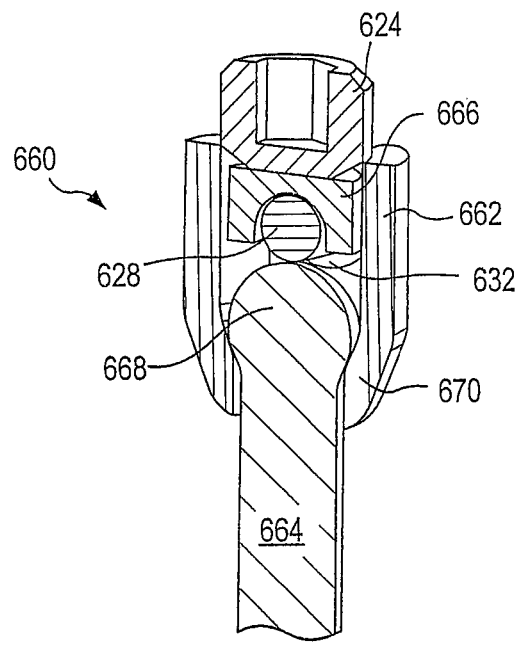
FIG. 34B is a cross-sectional view of the facet replacement device depicted in FIG. 34A.
Figure 34C:
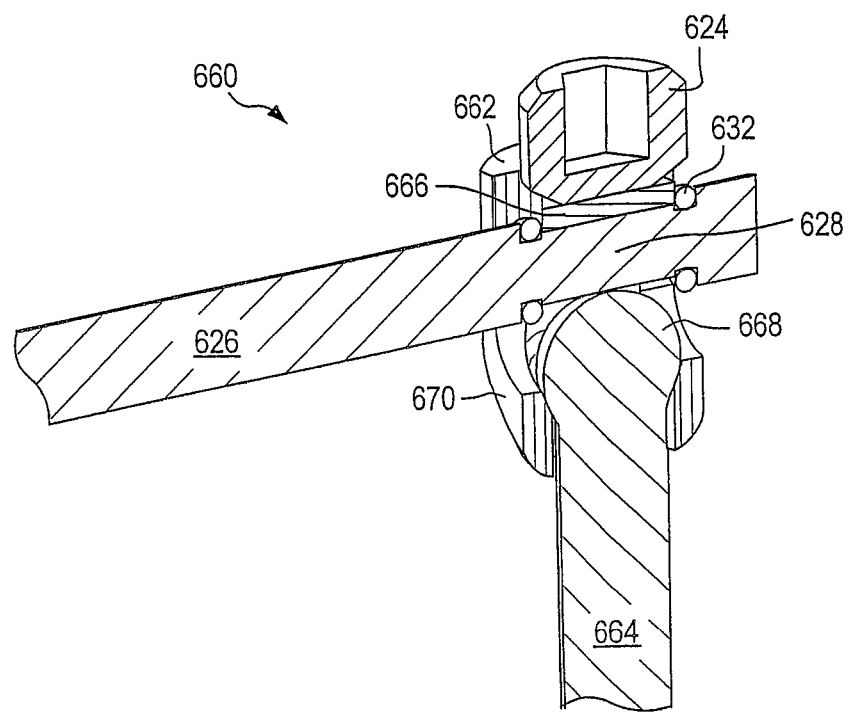
FIG. 34C is a cross-sectional view of the facet replacement device depicted in FIG. 34A.

FIGS. 34B and 34C depict cross-sectional views of facet replacement device 660. As shown in FIGS. 34B and 34C, reduced diameter portion 628 of rod 626 may be held loosely between upper saddle 666 and ball joint 668 of pedicle screw 664. With threading (not shown) inside pedicle screw head 662 extending only partially down toward the base of the pedicle screw head, upper saddle 666 may secure rod 626 in the pedicle screw head without causing the rod to bear down on ball joint 668 of pedicle screw 664. With rod 626 and ball joint 668 able to move freely, the rod may retain rotational (and/or translational) mobility after insertion of facet replacement device 660 in a human spine.

In some embodiments, instruments may be used to install elements of an implant in a spine. Instruments may also be used to position (e.g., rotate, translate, expand) elements of an implant in vivo. In certain embodiments, a single instrument may be used to perform multiple steps of a spinal procedure. For example, an instrument may be used to position an implant in an intervertebral space and to actuate an expansion member to expand the implant in the intervertebral space.

FIG. 35 depicts instrument 700 for use in installing and expanding an implant. Instrument 700 may have proximal end 702 and distal end 704. Instrument 700 may include outer shaft 706, driver 708, holding device 710, and handle 712. As used herein, "shaft" includes elongated members having various regular and irregular cross-sections, including, but not limited to, round, square, rectangular, hexagonal, or irregular. A shaft may be solid or hollow.

Instrument 700 may include thumbwheel 714. Thumbwheel 714 may be coupled to driver 708. Thumbwheel 714 may act as a control member for driver 708. As used herein, "control member" includes any element that is operable by a user to control position, orientation, or motion of another element. Other examples of control members include, but are not limited to, a knob, a lever, or a button. In some embodiments, a control member may be operated using a tool.

In one embodiment, thumbwheel 714 may be fixedly coupled to driver 708 such that driver 708 rotates as thumbwheel 714 is rotated. In another embodiment, thumbwheel 714 may be threadably coupled to driver 708 such that driver 708 translates along its axis when thumbwheel 714 is rotated.

FIG. 36 depicts a detail view of distal end 704 of instrument 700. Holding device 710 may hold an implant during insertion of the implant between two vertebrae. As used herein, "holding device" includes any element or combination of elements that may be used to hold, support, or grip another element, such as an implant, spacer, or insert. Examples of holding devices include, but are not limited to, a clamp, a clip, or a threaded rod. In some embodiments, a holding device may include one or more opposing holding elements. For example, as shown in FIG. 36, holding device 710 may include holding arms 716. Holding arms 716 may be hinged to base 718. Base 718 may be coupled to outer shaft 706. Holding arms 716 may be coupled to spring clip 720. Spring clip 720 may maintain holding arms 716 in a closed position (as shown in FIG. 36) unless at least a predetermined amount of separation force is applied to instrument 700 and an implant.

Lobes 722 on holding arms 716 may engage complementary surfaces (e.g., notches, grooves) on an implant or spacer. Engagement between lobes and complementary surfaces on an implant or spacer may promote engagement between an instrument and an implant or a spacer. Holding arms may include other engaging elements, such as tabs, grooves, or pins. In certain embodiments, the inner surfaces of holding arms on a holding device may be flat. The inner surfaces of holding arms may be textured or smooth.

In some embodiments, spring clip 720 may be at least partially made of a shape memory alloy. Spring clip 720 may be actuated by allowing the spring clip to reach a predetermined temperature. When spring clip 720 is actuated, the spring clip may urge holding arms 716 outwardly from a closed position. In one embodiment, spring clip 720 may be actuated by body heat. In another embodiment, spring clip 720 may be actuated by electrical current carried by insulated conductors in or on the instrument.

Base 718 of holding device 710 may allow for passage of driver 708. Driver 708 may include inner shaft 724 and driver head 726. Inner shaft 724 may be coupled with thumbwheel 714 (shown in FIG. 35). Driver head 726 may have any of various forms suitable for actuating (e.g., rotating, advancing) a portion of an expansion member or insert. In one embodiment, a driver head may include external threads that can engage internal threads on a portion of an implant. Other examples of driver head types include, but are not limited to, slotted, Phillips, square, hexagonal, or hexalobular. In some embodiments, the driver head may engage a set screw in the implant.

Figure 37:
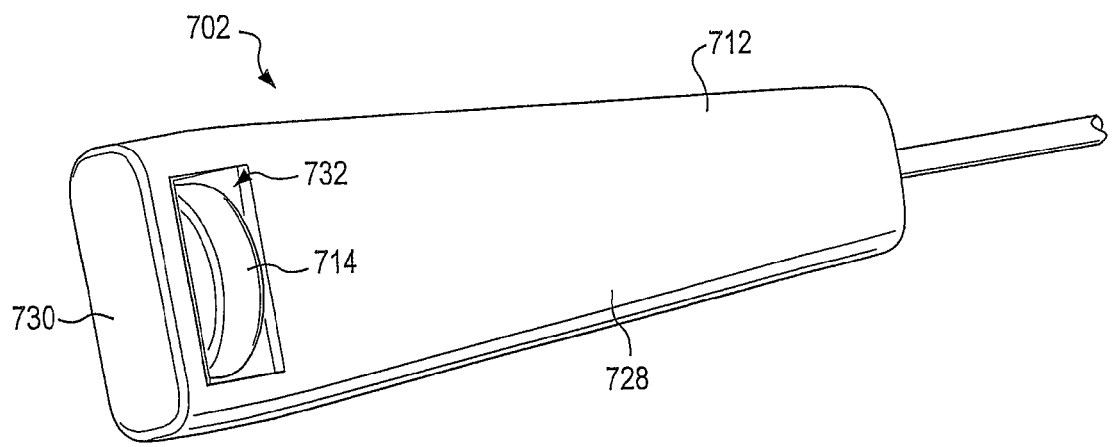
FIG. 37 is a detail view of a proximal end of an instrument for installing and expanding an implant.

FIG. 37 depicts a detail view of proximal end 702 of instrument 700. Handle 712 may include grip portion 728 and end portion 730. End portion 730 may include a surface suitable for receiving impact by another instrument. Slot 732 may be provided between grip portion 728 and end portion 730. Thumbwheel 714 may partially reside in slot 732. In certain embodiments, surfaces of thumbwheel 714 may have knurls, ribs, or similar characteristics to facilitate rotation of the thumbwheel.

Handle 712 may protect portions of the instrument from damage during use. For example, handle 712 may protect against damage to threads on inner shaft 724 when another instrument is used to strike instrument 700. In one embodiment, a transverse cross section of handle 712 at slot 732 may be generally rectangular, as shown in FIG. 37. A rectangular cross section at slot 732 may allow a user to access a sufficient portion of thumbwheel 714 to turn the thumbwheel, but still protect thumbwheel 714 and inner shaft 724 (shown in FIG. 35) from damage. A transverse cross section of handle at slot 732 may be shapes other than rectangular, such as square, oval, hexagonal, or irregular.

Although the protecting portions of instrument 700 shown in FIG. 37 are an integral part of handle 712, a protector in other embodiments may be a separate component from the handle. In certain embodiments, a protector may be removable from an instrument so that a user may access a driver and/or control member.

Figure 38:
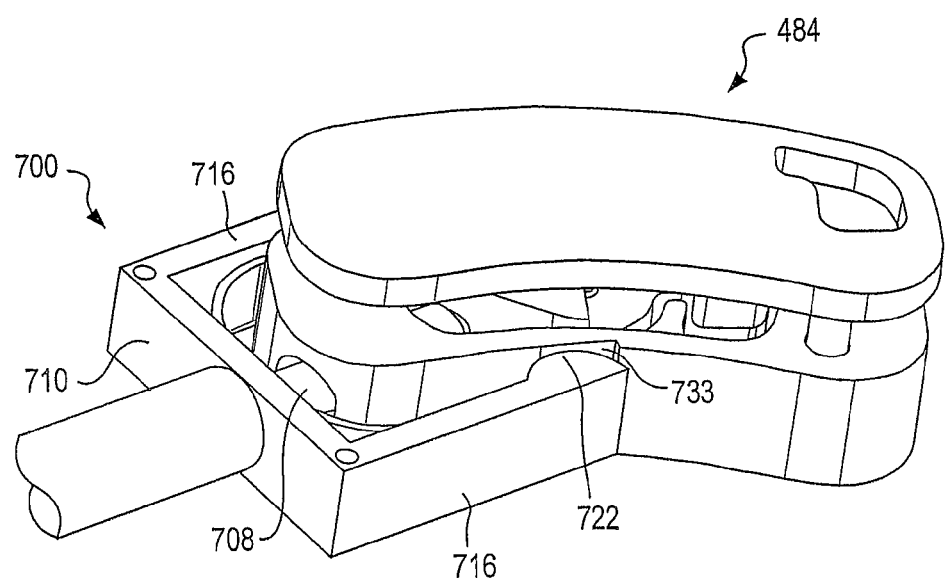
FIG. 38 is a perspective view of an expandable implant held by an instrument including a holding device and expansion driver.

FIG. 38 depicts implant 484 held by instrument 700 after driver 708 has been operated to expand the implant. When implant 484 is initially coupled to holding device 710, lobes 722 of holding arms 716 may engage in holding recesses 733 on either side of lower body 488. Engagement of lobes 722 in holding recesses 733 may help maintain a position of the implant during insertion and/or expansion of the implant. Engagement of lobes 722 within holding recesses 733 may place implant 484 in a desired alignment for insertion between the vertebrae and engagement with an expansion tool. The location of holding recesses 733 may be selected according to the approach to be used (e.g., TLIF, PLIF) and the location of an expansion member of the implant. For example, for a TLIF implant, holding recesses may, in some embodiments, be located near both longitudinal ends of the implant.

In some embodiments, driver head 726 may engage an insert (e.g., insert 472 depicted in FIG. 24D) of an implant. In other embodiments, driver head 726 may engage a set screw (e.g., advancing element 394 depicted in FIG. 21B) of an implant, which may in turn actuate (e.g., translate or rotate) an insert. Actuation of driver 708 may expand implant 484 to the expanded position shown in FIG. 38. After implant 484 has been expanded, instrument 700 may be pulled away from the surgical site with enough force to overcome the closing force of holding device 710, thereby spreading holding arms 716 apart to allow separation of instrument 700 from implant 484 and removal of the instrument from the site. In another embodiment, a release mechanism can be used to spread holding arms 716 apart.

In some embodiments, an inserter for a spacer may be used in combination with an implant holder and/or a driver for an expansion member. In some embodiments, an inserter may include a guide that engages a portion of an implant holder. The guide may be used to position the spacer near a desired location near the implant and/or to insert the spacer in the implant. Examples of guides include, but are not limited to, a fork, a hook, a ring, a spring clip, a tab, a rail, or a groove. In some embodiments, an inserter may be used to guide a spacer to a location near an implant, such as at a gap between an upper body and a lower body of the implant. In certain embodiments, an inserter may be advanced on a shaft to fully insert a spacer between upper and lower bodies of an implant.

FIG. 39 depicts instrument 736 including inserter 738 for holding spacer 470. Inserter 738 may include inserter shaft 740, inserter handle portion 742, spacer holding device 744, and guide fork 746. Guide fork 746 may engage outer shaft 706. Inserter handle portion 742 may include bend 748.

Bend 748 may allow a proximal portion of inserter handle portion 742 to be positioned close to handle 712 so inserter handle portion 742 may be manipulated in a relatively small incision.

In the embodiment shown in FIG. 39, inserter 738 may be easily separated from outer shaft 706. Thus, the surgeon could first insert and expand the implant, then introduce inserter 738 into the incision. In other embodiments, an inserter may be permanently coupled to the rest of an instrument.

Figure 41:
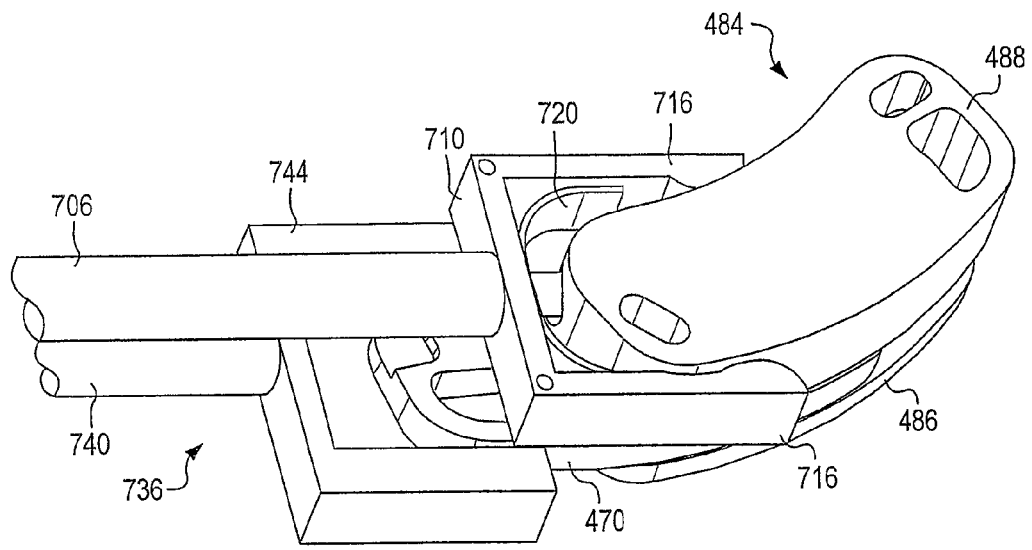
FIG. 41 is a perspective bottom view of an expandable implant with a partially inserted spacer.

FIG. 40 depicts a detail view of implant 484 held by instrument 736, as seen from the upper side of the implant. FIG. 41 depicts a detail view of implant 484 held by instrument 736, as seen from the lower side of the implant. In FIGS. 40 and 41, spacer 470 is partially inserted between upper body 486 and lower body 488 of implant 484.

Figure 42:
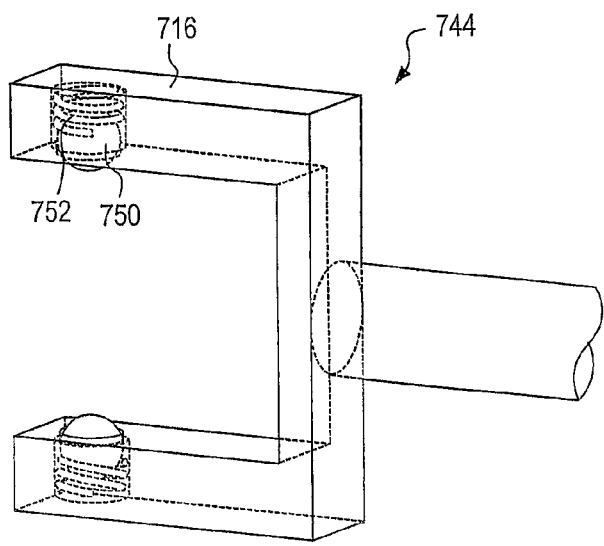
FIG. 42 is a perspective view of a holding device including opposing arms with ball detent mechanisms.

In the embodiment shown in FIG. 40, spacer holding device 744 includes holding arms 716 that are fixed with respect to base 718. Each of holding arms 716 may include ball detent mechanism 750. FIG. 42 depicts a detail view of ball detent mechanisms 750. Detent springs 752 may provide a desired amount of clamping force on spacer 470. In other embodiments, a spacer holding device may include hinged arms that are similar to those of holding device 710 shown in FIG. 36.

Referring again to FIG. 36, it is noted that spring clip 720 may serve as a biasing element to maintain a holding force on the implant. As used herein, a "biasing element" includes any element that biases a member of a device toward one position. A biasing element may be a separate element of a holding device or integral to another element of the device (e.g., a holding arm). Biasing elements include, but are not limited, resilient members such as metal springs or elastomeric bands. Additional embodiments of holding devices with biasing elements are described below.

Figure 43:
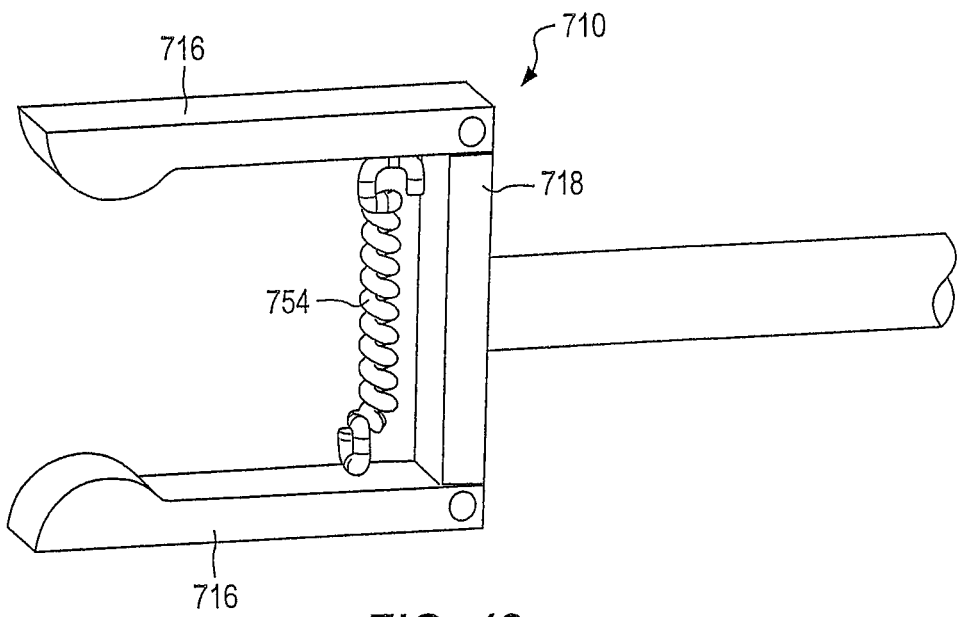
FIG. 43 is a perspective view of a holding device including opposing arms coupled by a coil spring.
Figure 44:
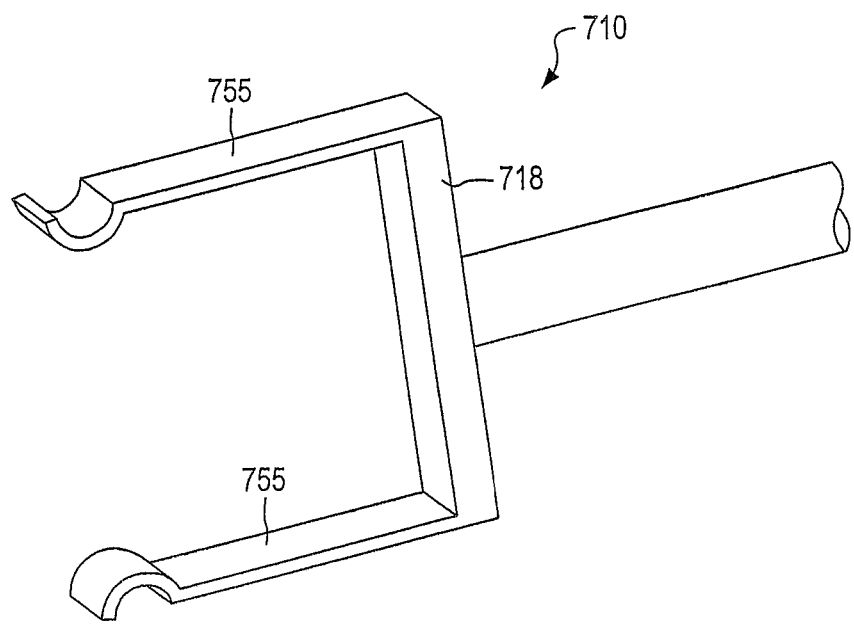
FIG. 44 is a perspective view of a holding device including opposing spring arms.

FIG. 43 depicts holding device 710 including holding arms 716 hinged to base 718 and connected by coil spring 754. In one embodiment, coil spring 754 is spot welded to the holding arms. FIG. 44 depicts an alternate embodiment of holding device 710 that includes spring arms 755. In certain embodiments, spring arms 755 may be made of 302, 314, or 316 stainless steel.

Figure 45:
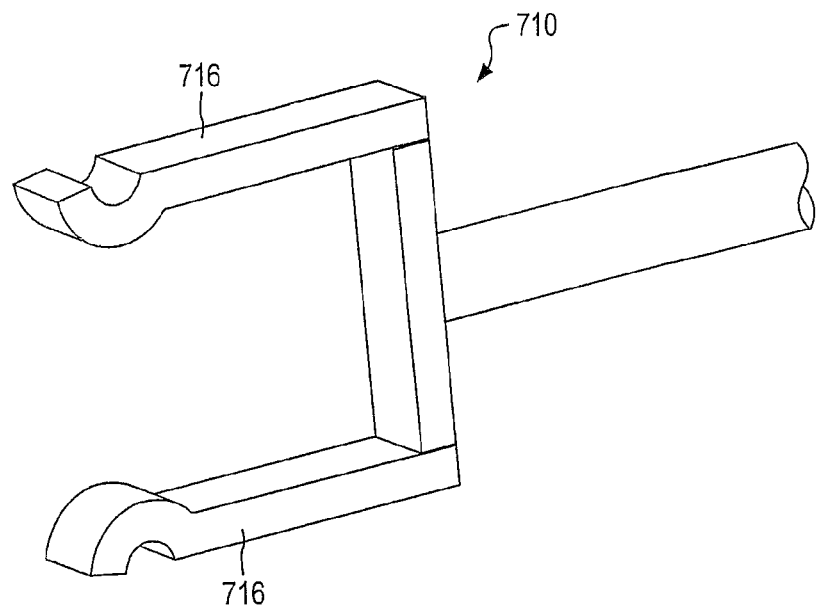
FIG. 45 is a perspective view of a holding device with shape memory alloy arms.

FIG. 45 depicts a holding device 710 having holding arms 716 made of a shape memory alloy. Holding arms 716 may be actuated by allowing the holding arms to reach a predetermined temperature. When holding arms 716 are actuated, the holding arms 716 may move outwardly from a closed position. Holding arms 716 may be actuated using body heat, insulated electrical current, or another heat source.

Figure 46:
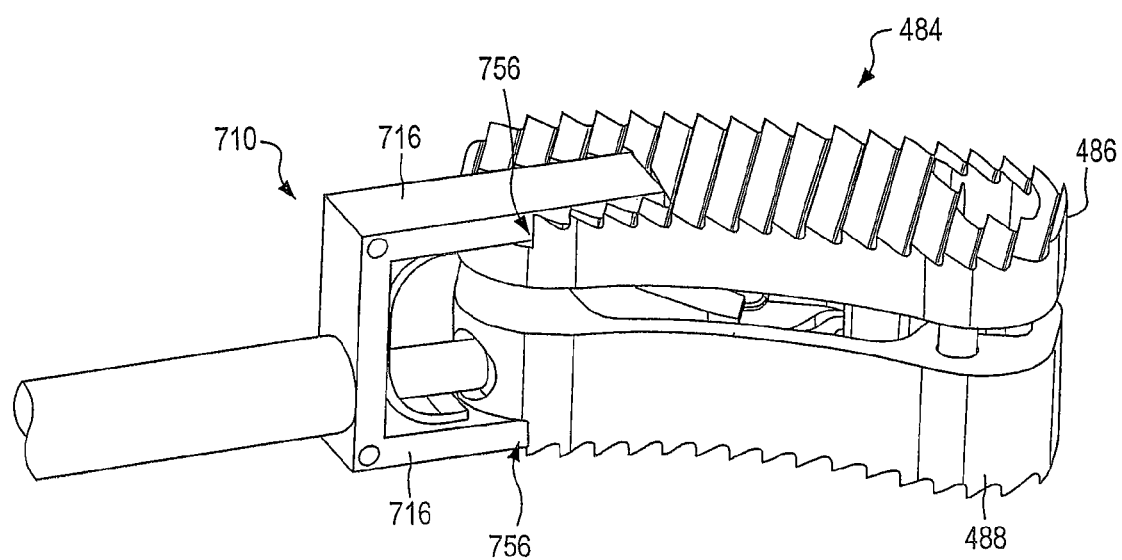
FIG. 46 is a perspective view of an implant held in a holding device including upper and lower holding arms.

FIG. 46 depicts an alternate embodiment of a holding device. Holding device 710 may engage a top surface of implant 484. Notches 756 in implant 484 may allow the outer surfaces of holding arms 716 to be flush with the outer surfaces of upper body 486 and lower body 488, facilitating insertion of implant 484 between the vertebrae. In another embodiment, a holding device may engage top and bottom surfaces of a spacer for an expandable implant.

Figure 47A:
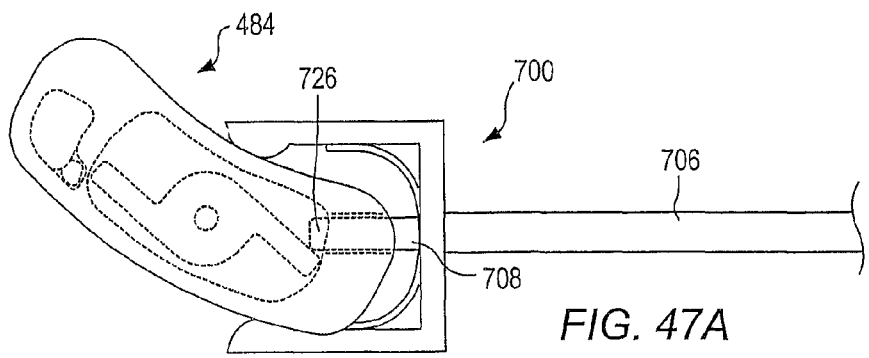
FIGS. 47A-47D illustrate use of an instrument to expand an implant and install a spacer.
Figure 47B:
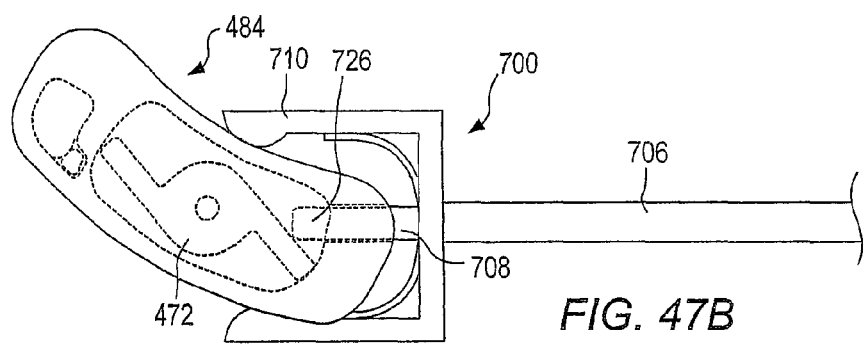

FIGS. 47A-47D depict a top view of an expandable implant during expansion of the implant and insertion of a spacer between upper and lower bodies of the implant. FIG. 47A depicts implant 484 on instrument 700 before expansion of implant 484. Driver head 726 of driver 708 may be advanced into a tapped through hole in lower body 488 of implant 484 until the tip of driver head 726 engages insert 472. Advancement of driver head 726 may rotate insert 472 to expand implant 484 between the vertebrae (see FIG. 47B). Holding device 710 may exert sufficient force on implant 484 to maintain the implant in a fixed position during actuation of driver 708.

Figure 47C:
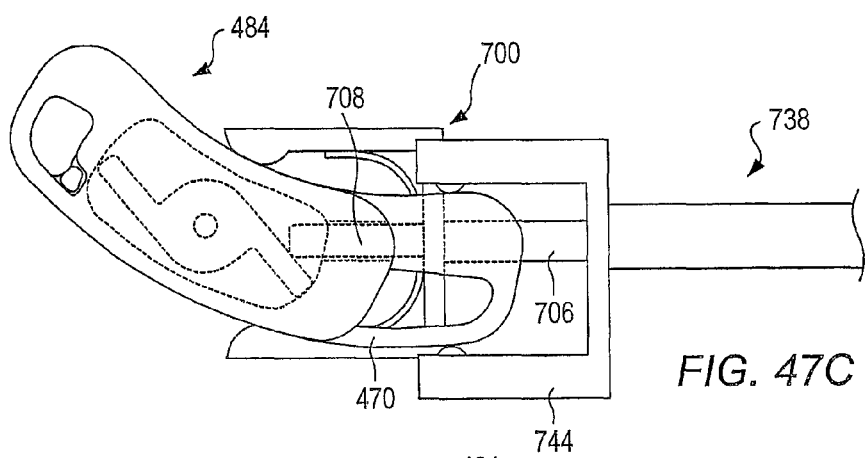
Figure 47D:
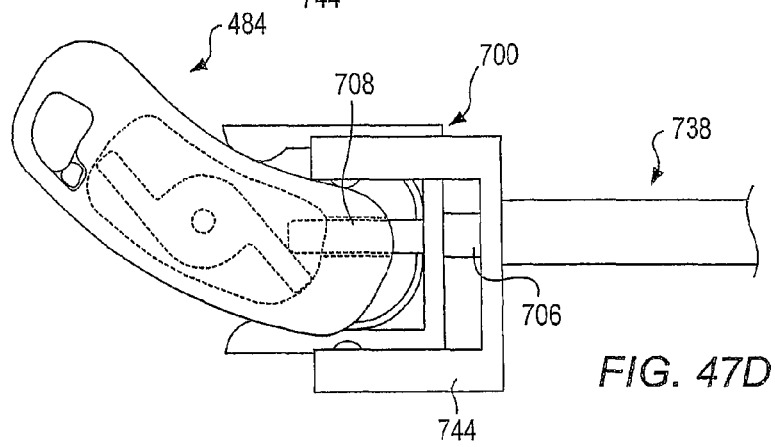

Guide fork 746 of inserter 738 (shown in FIG. 39) may be placed on outer shaft 706. Inserter 738 may be advanced on outer shaft 706 to move spacer 470 into position between the upper body and the lower body of implant 484 (FIG. 47C). Inserter 738 may be advanced until spacer 470 is fully installed between the upper and lower bodies of implant 484 (FIG. 47D). Once spacer 470 is fully installed, instrument 700 and inserter 738 may be withdrawn from the surgical site, either together or one at a time.

Figure 48:
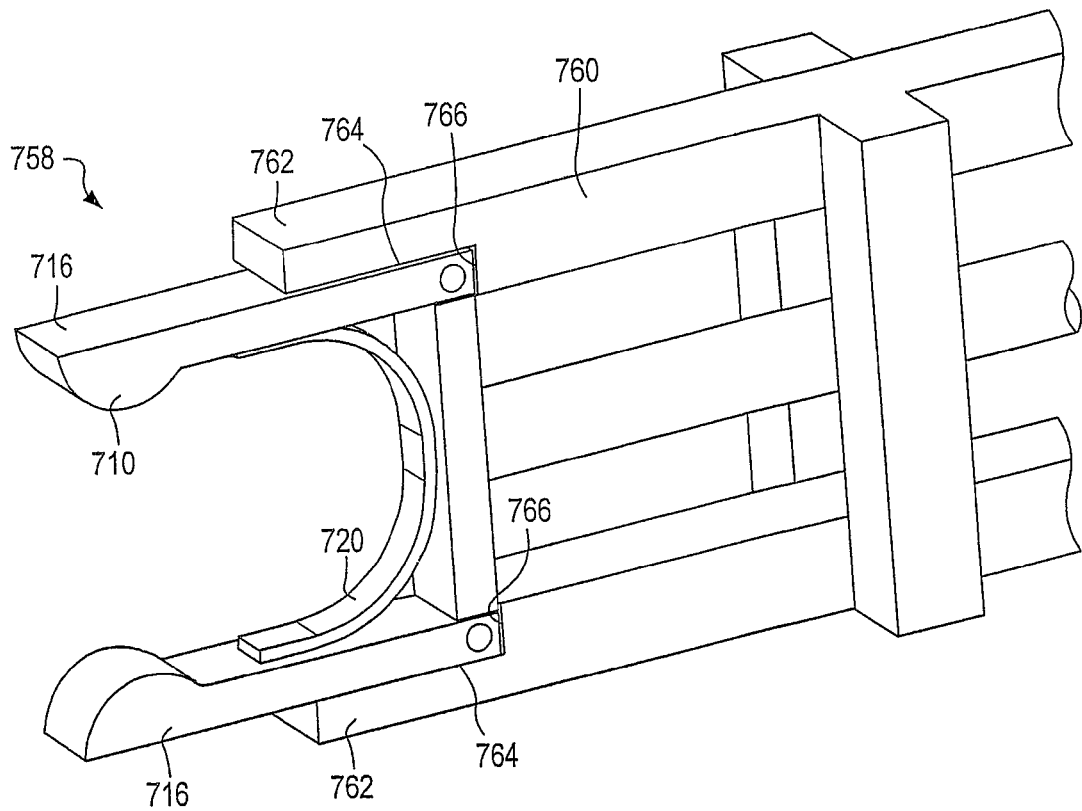
FIG. 48 is a perspective view of a distal end of an instrument including a holding device with a slide.

In certain embodiments, an instrument may include a movable element for maintaining a holding device in a closed position. FIG. 48 depicts a distal end of instrument 758 including slide 760. Slide 760 may include projections 762. Projections 762 may define notches 764 at a distal end of slide 760. Bottom surfaces 766 of notches 764 may act as stops against axial motion of holding device 710. Spring clip 720 may bias holding arms outwardly from the closed position shown in FIG. 48. When projections 762 are adjacent to holding arms 716 of holding device 710 (as shown in FIG. 48, for example), the projections may inhibit outward rotation of the holding arms, thereby keeping the holding device in a closed position. When slide 760 is retracted from holding arms 716 (e.g., by moving the slide proximally with respect to the holding device), the holding arms may move apart under the force of spring clip 720 to allow release of an implant from the instrument.

Other arrangements may be used to maintain a holding device in a closed position. For example, a slide may include a cylindrical sleeve that passes over the outer sides of a holding device. The inner wall of the sleeve may inhibit the holding arms from moving out of a closed position.

Figure 49:
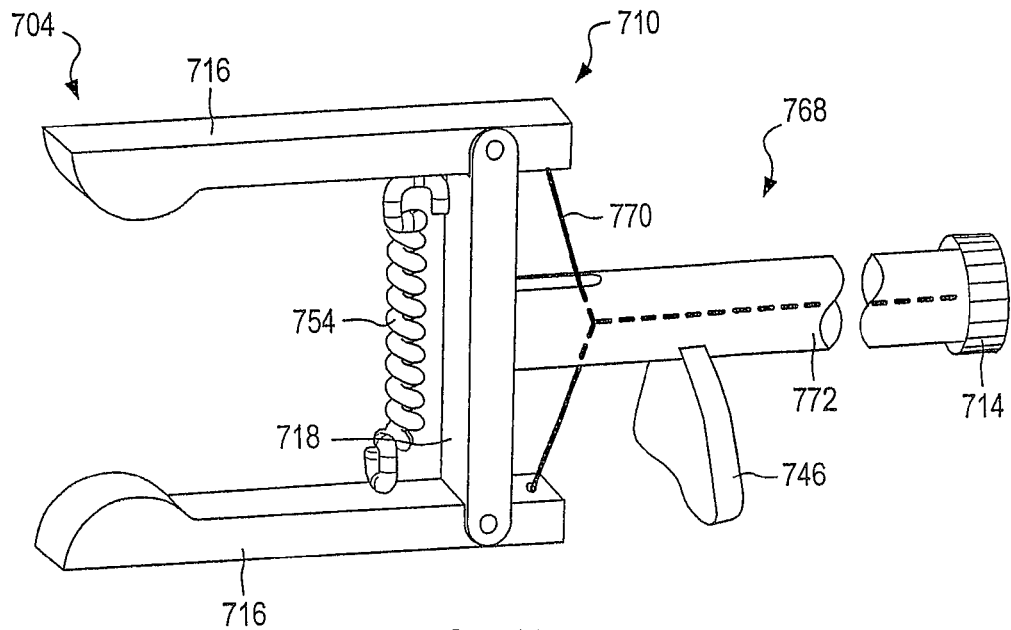
FIG. 49 is a perspective view of an instrument with a holding device coupled to a control member.

In some embodiments, a holding device for an implant or spacer may be coupled to a control member, such as a thumbwheel or lever. The control member may be operated to selectively hold and release the implant or spacer. FIG. 49 depicts a perspective view of inserter 768 including holding device 710. Holding arms 716 of holding device 710 may be coupled to coil spring 754 in a similar manner as described above relative to FIG. 43. Coil spring 754 may bias holding arms 716 into a closed position on a spacer. Cable 770 may extend between thumbwheel 714 and holding arms 716 through hollow shaft 772. Thumbwheel 714 may be operated to draw cable 770 away from distal end 704 of instrument 768. Cable 770 may act against the force of coil spring 754 to open holding arms 716, thereby allowing the spacer to be released from the holding device. Inserter 768 may include guide fork 746. Guide fork 746 may slidably engage a portion of an implant holder (e.g., the outer shaft shown in FIG. 35) to facilitate positioning of the spacer prior to release of the spacer. In another embodiment, a control member may be connected to a locking slide to selectively lock and release a holding device.

Figure 50A:
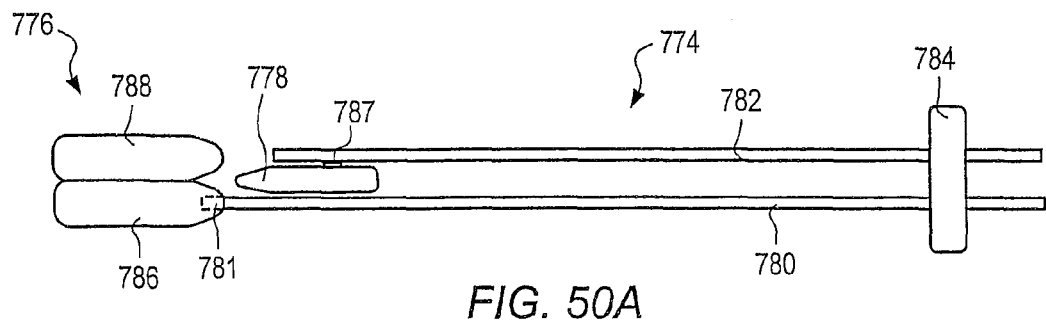
FIG. 50A is a side view of a dual rod instrument during guided advancement of a spacer.
Figure 50B:
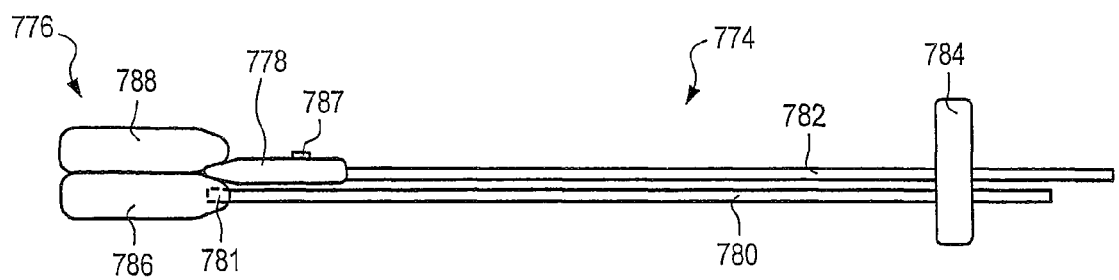
FIG. 50B is a side view of a dual rod instrument with one rod positioned to impact the spacer between upper and lower bodies of an implant.

FIGS. 50A and 50B depict instrument 774 including a pair of rods for inserting implant 776 having spacer 778. Bottom rod 780 and top rod 782 of instrument 774 may be commonly supported on base member 784. Bottom rod 780 may include threaded portion 781. Threaded portion 781 may engage in a tapped hole in lower body 786 of implant 776. In one embodiment, tab 787 on spacer 778 may engage a channel or groove in top rod 782 to help guide and/or align spacer 778. Top rod 782 may be used to guide spacer 778 to a gap between upper body 788 and lower body 786, as shown in FIG. 50A. Once spacer 778 is in position for insertion between upper body 788 and lower body 786 of implant 776, top rod 782 may be repositioned in base member 784 such that a distal end of top rod 782 is behind spacer 778, as shown in FIG. 50B. Top rod 782 can be used to advance spacer 778 between upper body 788 and lower body 786. In certain embodiments, top rod 782 may be used to impact spacer 778 between upper body 788 and lower body 786.

Figure 51:
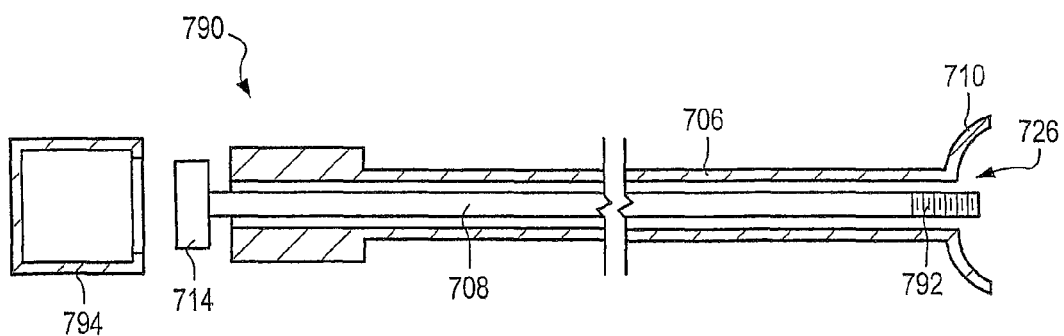
FIG. 51 is a cross-sectional view of an instrument including a driving portion that directly engages an insert for expanding an implant.

FIG. 51 depicts alternative embodiment of an instrument 790 including driver 708 with driver head 726. Driver head 726 may include threaded portion 792. In one embodiment, threaded portion 792 may be threaded into a tapped through opening in an upper or lower body of an implant. As threaded portion 792 of driver head 726 is advanced through the opening, a distal tip of driver head 726 may actuate (e.g., translate, rotate) an insert. Instrument 790 may include outer shaft 706 and holding device 710. In certain embodiments, holding device 710 of instrument 790 may be shaped to match a contour of an implant or a spacer. In one embodiment, holding device 710 may have an arcuate shape. Driver head 726 may be actuated by thumbwheel 714. Instrument 790 may include removable cover 794. Removable cover 794 may protect thumbwheel 714 from damage during use.

Figures 52A, 52B:
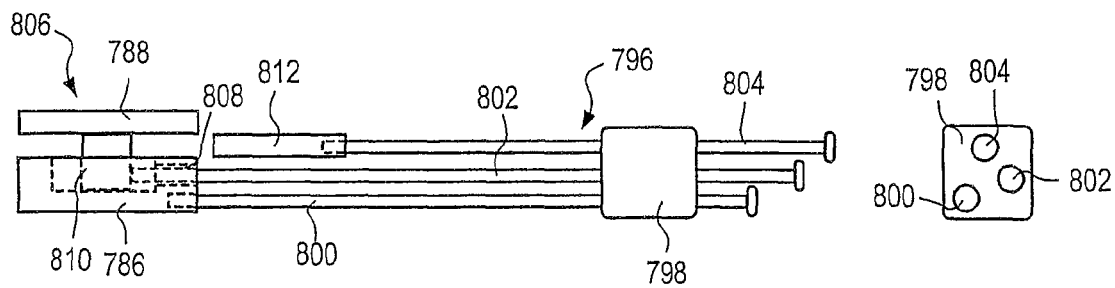
FIGS. 52A and 52B are side views of an instrument including multiple rods with threaded ends.

FIGS. 52A and 52B depict an alternate embodiment of an instrument for placing and expanding an implant and inserting a spacer. Instrument 796 may include base member 798. Base member 798 may carry holder rod 800, driver rod 802, and inserter rod 804. Holder rod 800 may threadably engage a tapped hole in lower body 786 to support implant 806. Driver rod 802 may threadably engage through hole 808 in lower body 786. Driver rod 802 may be advanced to actuate insert 810 to increase a separation distance between lower body 786 and upper body 788, thereby expanding implant 806. Spacer 812 may be threadably coupled to inserter rod 804. Inserter rod 804 may be guided on base member 798 to advance spacer 812 between lower body 786 and upper body 788. Holder rod 800, driver rod 802, and inserter rod 804 may be rotated to disengage the rods from implant 806. The rods may be removable from base member 798. In some embodiments, inserter rod 804 may be loaded into an open channel in base member 798.

It will be understood that any or all of the threaded tips on rods 800, 802, and 804 may be replaced by other holding devices including, but not limited to, the holding devices shown in FIGS. 36-44. It will be further understood that in other embodiments, an instrument may omit one or more of the implant holder, the expansion driver, or the spacer inserter. For example, an instrument may include only an implant holder and an expansion driver, or only an implant holder and a spacer inserter.

Figures 53, 54:
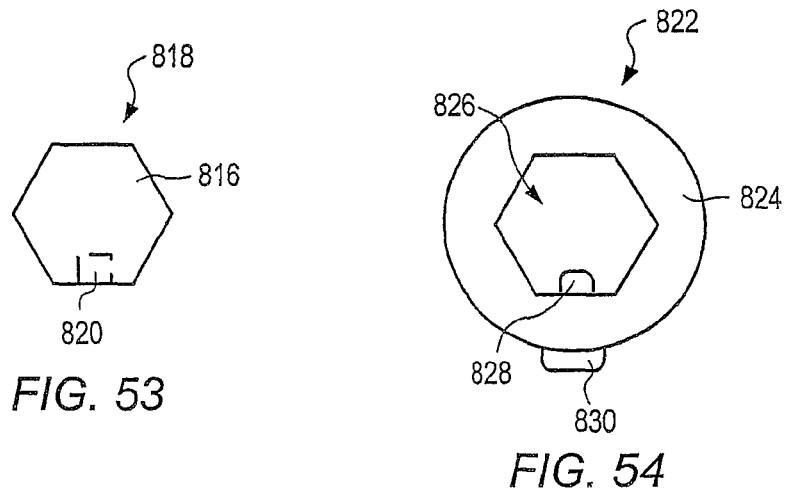
FIG. 53 is a schematic end view of a head of a fastener for a spinal system.
FIG. 54 is a schematic end view of a driver for a fastener of a spinal system.

In an embodiments, a driver for components of a spinal system may include a feature for locking with an element of a spinal system. FIG. 53 depicts a schematic view of a proximal end of head 816 on fastener 818 for a spinal system. Head 816 may include side hole 820. A fastener for a spinal system may include, but is not limited to, a set screw, a pedicle screw, or a threaded top for a polyaxial screw. FIG. 54 depicts a schematic view of a distal end of driver 822. Driver 822 may include sleeve 824 having socket 826. Driver 822 may include lock element 828. Lock element 828 may retractably extend into socket 826. Button 830 on sleeve may be manually operated to retract lock element 828 from socket 826. When sleeve 824 of driver 822 is placed on head 816 of fastener 818, lock element 828 of driver 822 may engage in side hole 820.

Engagement of lock element 828 in side hole 820 may inhibit axial separation of driver 822 from head 816 of fastener 818. A locking element may reduce a risk of a fastener disengaging from a tool during use. In certain embodiments, lock element 828 may be used to capture a break-off head of a top for a polyaxial screw. In certain embodiments, driver 822 may be coupled with a detachable handle. In some embodiments, driver 822 may be used with a power tool (e.g., a drill).

In an embodiment, an implant (e.g., for an expanse cage, dynamic cage) may be placed in a human spine using a posterior approach to a diseased lumbar disc. In some embodiments, the surgeon may use the same approach as is typically used in a microdiscectomy, TLIF, or minimally invasive posterior exposure. Such procedures involve removing some of the lamina and the medial facet joint. More bone, including the spinous process and the entire facet may be removed if indicated.

The vital structures involved with the posterior approach are the nerve roots. The exiting root is the root that leaves the spinal canal just cephalad (above) the disc, and the traversing root leaves the spinal canal just caudad (below) the disc. The thecal sac houses the other nerve roots that exit lower. The triangle between the exiting nerve root and the traversing nerve root (Pambin's or Cambin's triangle) is the extent of the access to the disc. The triangle may be enlarged by retracting the traversing nerve root medially. If retraction is done too vigorously, however, retraction injuries may occur and serious complications such as nerve root sleeve tear may result, causing spinal fluid leakage, nerve root injury, avulsion and even spinal cord injury.

After the lamina has been removed and the traversing root retracted medially, the posterior annulus may be exposed. While the root is retracted gently, the surgeon may create an annulotomy. Pituitary forceps may be used to remove disc material. Successively larger forceps may be used until an adequate amount of disc is removed. Care should be taken not to penetrate the anterior annulus and enter the retroperitoneal space. After adequate disc material has been removed, the end plates may be prepared using osteotomes to remove posterior ostephytes and cutting curettes to decorticate the end plates. The object of end plate preparation is to remove the cartilaginous tissue and score the cortical bone without completely removing the cortical strength.

Once the end plates have been prepared, a trial may be placed in the disc space. The trial should be snug without significantly distracting the end plates. An unexpanded implant of approximately the same size as the trial may then be inserted into the disc space. Once positioned anterior to the nerve roots, the implant may be expanded. In some embodiments, a spacer may be introduced following expansion of the implant. The spacer may include a protrusion, groove, or similar element that snaps or locks into place to provide a tactile sensation as the spacer reaches a fully inserted position. A tactile sensation may provide the surgeon with positive feedback that the spacer is in place. In certain embodiments, the implant may be further rotated within the space after the spacer is introduced, according to the preference of the surgeon.

An expandable implant (e.g., an expanse cage or dynamic device) may allow a larger device to be placed into the disc from a posterior approach without over distracting the nerve roots or the ligaments. In some embodiments, the implant may be expanded without any over distraction. This advantage may allow the surgeon to tension the annulus, avoid resection of the anterior longitudinal ligament, and decompress the nerve roots without requiring over distraction and the attendant possibility of injury to the nerves and ligaments. For reasons outlined above, many patients are not suitable candidates for an anterior approach. In one embodiment, an implant of less than about 12 mm in width is placed posteriorly without over distraction. In another embodiment, an implant of less than about 10 mm in width is placed posteriorly without overdistraction.

In an embodiment, an expandable implant may expand throughout its entire width. In some embodiments, an expandable implant may be used for posterior disc height restoration without increasing lordosis. In other embodiments, an expandable implant may be used for posterior disc height restoration with increasing lordosis. In certain embodiments, an implant may be placed using a TLIF approach. Although some of the description herein relates to a PLIF or TLIF approach, it will be understood that implants as described herein may be placed using an anterior approach.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. An intervertebral implant for a human spine, comprising:
    an upper body comprising an inferior surface and a superior surface, wherein the superior surface of the upper body is configured to engage a first vertebra of the human spine;
    a lower body comprising a superior surface and an inferior surface, wherein the inferior surface of the lower body is configured to engage a second vertebra of the human spine; and
    an expansion member comprising elongated body portion with a substantially flat inferior surface substantially parallel to the inferior surface of the lower body and a first angled portion positioned at or towards an insertion end of the elongated body, wherein the expansion member is configured to be positioned between the upper body and the lower body and extend along substantially the entire length of the inferior surface of the upper and the superior surface of the lower body, wherein applying a force to a trailing most end of the elongated body opposite the insertion end of the elongated body advances the first angled portion in a substantially linear direction from a proximal end towards a distal end of the implant such that the first angled portion engages with a rigid second angled portion of the implant to increase a separation distance between the superior surface of the upper body and the inferior surface of the lower body at a proximal most end and a distal most end of the implant, wherein the rigid second angled portion is at an angle that is oblique to the substantially linear direction prior to the elongated body advancing in the substantially linear direction; and
    wherein the first angled portion advances between at least a portion of the inferior surface of the upper body and at least a portion of the superior surface of the lower body, after insertion of the upper and lower body in the spine.

2. The intervertebral implant of claim 1, wherein at least a portion of the expansion member further comprises a substantially flat inferior surface.

3. The intervertebral implant of claim 1, wherein at least a portion of the expansion member further comprises a substantially flat superior surface.

4. The intervertebral implant of claim 1, wherein increasing the separation distance between the superior surface of the upper body and the inferior surface of the lower body increases a height of the intervertebral implant.

5. The intervertebral implant of claim 1, further comprising an advancing element, wherein the advancing element is configured to be advanced in an anteroposterior direction or a posteroanterior direction to apply a force to the trailing end of the elongated body opposite the insertion end of the elongated body.

6. The intervertebral implant of claim 1, further comprising an advancing element, wherein the advancing element is configured to apply a force to the trailing end of the elongated body opposite the insertion end of the elongated body.

7. The intervertebral implant of claim 1, further comprising an advancing element, wherein the advancing element is configured to inhibit dislocation of the expansion member after increasing the separation distance between the superior surface of the upper body and the inferior surface of the lower body.

8. The intervertebral implant of claim 1, further comprising an advancing element, wherein the advancing element is configured to apply a force to the trailing end of the elongated body opposite the insertion end of the elongated body, wherein the advancing element is threaded.

9. The intervertebral implant of claim 1, wherein as the separation distance increases between the superior surface of the upper body and the inferior surface of the lower body the superior surface of the upper body and the inferior surface of the lower body remain at substantially the same angle relative to one another.

10. The intervertebral implant of claim 1, wherein increasing the separation distance between the superior surface of the upper body and the inferior surface of the lower body increases a distance between the first vertebra and the second vertebra at least at a posterior side and at an anterior side of the first and the second vertebra.

11. The intervertebral implant of claim 1, wherein the force applied to the trailing end of the elongated body is a pushing force.

12. The intervertebral implant of claim 1, wherein increasing the separation distance between the superior surface of the upper body and the inferior surface of the lower body increases a distance between the superior surface of the upper body and the inferior surface of the lower body a substantially equivalent distance at the proximal end and the distal end of the implant.

13. The intervertebral implant of claim 1, wherein at least a majority of the superior surface of the upper body and at least a majority of the inferior surface of the lower body are moved when separation occurs.

14. The intervertebral implant of claim 1, wherein the shape of the rigid second angled portion does not vary as the separation distance increases.

15. The intervertebral implant of claim 1, wherein the rigid second angled portion is a solid ramp.

16. The intervertebral implant of claim 1, wherein the rigid second angled portion is a ramped surface.

17. The intervertebral implant of claim 1, wherein the first angled portion is a ramped surface.

18. The intervertebral implant of claim 1, wherein the first angled portion is a ramped surface, wherein the rigid second angled portion is a ramped surface, wherein the ramped surface of the first angled portion engages the ramped surface of the rigid second angled portion and the ramped portion of the first or the second angled portion is coupled to the superior surface of the lower body or the inferior surface of the upper body.

19. The intervertebral implant of claim 1, wherein the rigid second angled portion is coupled to the upper body, and wherein when the first angled portion engages with the rigid second angled portion the rigid second angled portion and the upper body move to increase the separation distance.

20. The intervertebral implant of claim 1, wherein the rigid second angled portion is coupled to the lower body, and wherein when the first angled portion engages with the rigid second angled portion the rigid second angled portion and the lower body move to increase the separation distance.

21. The intervertebral implant of claim 1, wherein the upper body, lower body, and expansion member are configured to inhibit dislolcation of the upper body from the lower body.

22. The intervertebral implant of claim 21, wherein at least one of the lower body or expansion member includes generally upwardly projecting extensions and at least one of the upper body or expansion member includes recesses configured to accept the extensions, wherein the extensions when positioned in the recesses are configured to inhibit disclocation of the upper body from the lower body.

23. An intervertebral implant for a human spine, comprising:
an upper body comprising an inferior surface and a superior surface, wherein the superior surface of the upper body is configured to engage a first vertebra of the human spine;
a lower body comprising a superior surface and an inferior surface, wherein the inferior surface of the lower body is configured to engage a second vertebra of the human spine;
an expansion member comprising elongated body portion with a substantially flat inferior surface substantially parallel to the inferior surface of the lower body and a first angled portion positioned at or towards an insertion end of the elongated body, wherein the expansion member is configured to be positioned between the upper body and the lower body and extend along substantially the entire length of the inferior surface of the upper and the superior surface of the lower body, wherein applying a force to a trailing most end of the elongated body opposite the insertion end of the elongated body advances the first angled portion in a substantially linear direction from a proximal end towards a distal end of the implant such that the first angled portion engages with a rigid second angled portion of the implant to expand the intervertebral implant at a proximal most end and a distal most end of the implant, wherein the rigid second angled portion is at an angle that is oblique to the substantially linear direction prior to the elongated body advancing in the substantially linear direction, and wherein the first angled portion advances between at least a portion of the inferior surface of the upper body and at least a portion of the superior surface of the lower body, after insertion of the upper and lower body in the spine; and
an advancing element, wherein the advancing element is configured to apply a force to the trailing end of the elongated body opposite the insertion end of the elongated body.

24. The intervertebral implant of claim 23, wherein the advancing element is configured to be advanced in an anteroposterior direction or a posteroanterior direction to apply a force to the trailing end of the elongated body opposite the insertion end of the elongated body.

25. The intervertebral implant of claim 23, wherein the advancing element is configured to inhibit dislocation of the expansion member after expanding the intervertebral implant.

26. The intervertebral implant of claim 23, wherein the advancing element is threaded.

27. The intervertebral implant of claim 23, wherein at least a portion of the expansion member further comprises a substantially flat inferior surface.

28. The intervertebral implant of claim 23, wherein at least a portion of the expansion member further comprises a substantially flat superior surface.

29. The intervertebral implant of claim 23, wherein expanding the intervertebral implant increases a height of the intervertebral implant.

30. The intervertebral implant of claim 23, wherein as the separation distance increases between the superior surface of the upper body and the inferior surface of the lower body the superior surface of the upper body and the inferior surface of the lower body remain at substantially the same angle relative to one another.

31. The intervertebral implant of claim 23, wherein increasing the separation distance between the superior surface of the upper body and the inferior surface of the lower body increases a distance between the first vertebra and the second vertebra at least at a posterior side and at an anterior side of the first and the second vertebra.

32. The intervertebral implant of claim 23, wherein the force applied to the trailing end of the elongated body is a pushing force.

33. The intervertebral implant of claim 23, wherein increasing the separation distance between the superior surface of the upper body and the inferior surface of the lower body increases a distance between the superior surface of the upper body and the inferior surface of the lower body a substantially equivalent distance at the proximal end and the distal end of the implant.

34. The intervertebral implant of claim 23, wherein at least a majority of the superior surface of the upper body and at least a majority of the inferior surface of the lower body are moved when separation occurs.

35. The intervertebral implant of claim 23, wherein the shape of the rigid second angled portion does not vary as the separation distance increases.

36. The intervertebral implant of claim 23, wherein the rigid second angled portion is a solid ramp.

37. The intervertebral implant of claim 23, wherein the rigid second angled portion is a ramped surface.

38. The intervertebral implant of claim 23, wherein the first angled portion is a ramped surface.

39. The intervertebral implant of claim 23, wherein the first angled portion is a ramped surface, wherein the rigid second angled portion is a ramped surface, wherein the ramped surface of the first angled portion engages the ramped surface of the rigid second angled portion and the ramped portion of the first or the second angled portion is coupled to the superior surface of the lower body or the inferior surface of the upper body.

40. The intervertebral implant of claim 23, wherein the rigid second angled portion is coupled to the upper body, and wherein when the first angled portion engages with the rigid second angled portion the rigid second angled portion and the upper body move to increase the separation distance.

41. The intervertebral implant of claim 23, wherein the rigid second angled portion is coupled to the lower body, and wherein when the first angled portion engages with the rigid second angled portion the rigid second angled portion and the lower body move to increase the separation distance.

42. The intervertebral implant of claim 23, wherein the upper body, lower body, and expansion member are configured to inhibit dislolcation of the upper body from the lower body.

43. The intervertebral implant of claim 42, wherein at least one of the lower body or expansion member includes generally upwardly projecting extensions and at least one of the upper body or expansion member includes recesses configured to accept the extensions, wherein the extensions when positioned in the recesses are configured to inhibit discloation of the upper body from the lower body.

44. An intervertebral implant for a human spine, comprising:
an upper body comprising an inferior surface and a superior surface, wherein the superior surface of the upper body is configured to engage a first vertebra of the human spine;
a lower body comprising a superior surface and an inferior surface, wherein the inferior surface of the lower body is configured to engage a second vertebra of the human spine;
an expansion member comprising elongated body portion with a substantially flat inferior surface substantially parallel to the inferior surface of the lower body and a first angled portion positioned at or towards an insertion end of the elongated body, wherein the expansion member is configured to be positioned between the upper body and the lower body and extend along substantially the entire length of the inferior surface of the upper and the superior surface of the lower body, wherein applying a force to a trailing most end of the elongated body opposite the insertion end of the elongated body advances the first angled portion in a substantially linear direction from a proximal end towards a distal end of the implant such that the first angled portion engages with a rigid second angled portion of the implant to increase a separation distance between the superior surface of the upper body and the inferior surface of the lower body at a proximal most end and a distal most end of the implant, wherein the rigid second angled portion is at an angle that is oblique to the substantially linear direction prior to the elongated body advancing in the substantially linear direction, and wherein the first angled portion advances between at least a portion of the inferior surface of the upper body and at least a portion of the superior surface of the lower body, after insertion of the upper and lower body in the spine; and
an advancing element, wherein the advancing element is configured to apply a force to the trailing end of the elongated body opposite the insertion end of the elongated body, wherein the advancing element is configured to inhibit dislocation of the expansion member after increasing the separation distance between the superior surface of the upper body and the inferior surface of the lower body.

45. The intervertebral implant of claim 44, wherein increasing the separation distance between the superior surface of the upper body and the inferior surface of the lower body increases a height of the intervertebral implant.

46. The intervertebral implant of claim 44, wherein the advancing element is configured to be advanced in an anteroposterior direction or a posteroanterior direction to apply a force to the trailing end of the elongated body opposite the insertion end of the elongated body.

47. The intervertebral implant of claim 44, wherein the advancing element is threaded.

48. The intervertebral implant of claim 44, wherein at least a portion of the expansion member further comprises a substantially flat inferior surface.

49. The intervertebral implant of claim 44, wherein at least a portion of the expansion member further comprises a substantially flat superior surface.

50. The intervertebral implant of claim 44, wherein as the separation distance increases between the superior surface of the upper body and the inferior surface of the lower body the superior surface of the upper body and the inferior surface of the lower body remain at substantially the same angle relative to one another.

51. The intervertebral implant of claim 44, wherein increasing the separation distance between the superior surface of the upper body and the inferior surface of the lower body increases a distance between the first vertebra and the second vertebra at least at a posterior side and at an anterior side of the first and the second vertebra.

52. The intervertebral implant of claim 44, wherein the force applied to the trailing end of the elongated body is a pushing force.

53. The intervertebral implant of claim 44, wherein increasing the separation distance between the superior surface of the upper body and the inferior surface of the lower body increases a distance between the superior surface of the upper body and the inferior surface of the lower body a substantially equivalent distance at the proximal end and the distal end of the implant.

54. The intervertebral implant of claim 44, wherein at least a majority of the superior surface of the upper body and at least a majority of the inferior surface of the lower body are moved when separation occurs.

55. The intervertebral implant of claim 44, wherein the shape of the rigid second angled portion does not vary as the separation distance increases.

56. The intervertebral implant of claim 44, wherein the rigid second angled portion is a solid ramp.

57. The intervertebral implant of claim 44, wherein the rigid second angled portion is a ramped surface.

58. The intervertebral implant of claim 44, wherein the first angled portion is a ramped surface.

59. The intervertebral implant of claim 44, wherein the first angled portion is a ramped surface, wherein the rigid second angled portion is a ramped surface, wherein the ramped surface of the first angled portion engages the ramped surface of the rigid second angled portion and the ramped portion of the first or the second angled portion is coupled to the superior surface of the lower body or the inferior surface of the upper body.

60. The intervertebral implant of claim 44, wherein the rigid second angled portion is coupled to the upper body, and wherein when the first angled portion engages with the rigid second angled portion the rigid second angled portion and the upper body move to increase the separation distance.

61. The intervertebral implant of claim 44, wherein the rigid second angled portion is coupled to the lower body, and wherein when the first angled portion engages with the rigid second angled portion the rigid second angled portion and the lower body move to increase the separation distance.

62. The intervertebral implant of claim 44, wherein the upper body, lower body, and expansion member are configured to inhibit dislocation of the upper body from the lower body.

63. The intervertebral implant of claim 62, wherein at least one of the lower body or expansion member includes generally upwardly projecting extensions and at least one of the upper body or expansion member includes recesses configured to accept the extensions, wherein the extensions when positioned in the recesses are configured to inhibit discloation of the upper body from the lower body.

64. An intervertebral implant for a human spine, comprising:
an upper body comprising an inferior surface and a superior surface, wherein the superior surface of the upper body is configured to engage a first vertebra of the human spine;
a lower body comprising a superior surface and an inferior surface, wherein the inferior surface of the lower body is configured to engage a second vertebra of the human spine; and
an expansion member comprising elongated body portion with a substantially flat inferior surface substantially parallel to the inferior surface of the lower body and a first angled portion positioned at or towards an insertion end of the elongated body, wherein the expansion member is configured to be positioned between the upper body and the lower body and extend along substantially the entire length of the inferior surface of the upper and the superior surface of the lower body, wherein applying a pushing force to a trailing most end of the elongated body opposite the insertion end of the elongated body advances the first angled portion in a substantially linear direction from a proximal end towards a distal end of the implant such that the first angled portion engages with a rigid second angled portion of the implant to increase a separation distance between the superior surface of the upper body and the inferior surface of the lower body at a proximal most end and a distal most end of the implant, wherein the rigid second angled portion is at an angle that is oblique to the substantially linear direction prior to the elongated body advancing in the substantially linear direction,
wherein the first angled portion advances between at least a portion of the inferior surface of the upper body and at least a portion of the superior surface of the lower body, after insertion of the upper and lower body in the spine, and
wherein increasing the separation distance between the superior surface of the upper body and the inferior surface of the lower body increases a distance between the superior surface of the upper body and the inferior surface of the lower body at at least the proximal end and the distal end of the implant.

65. The intervertebral implant of claim 64, wherein increasing the separation distance further increases a distance between the superior surface of the upper body and the inferior surface of the lower body a substantially equivalent distance between the proximal end and the distal end of the implant.

66. The intervertebral implant of claim 64, wherein the upper body, lower body, and expansion member are configured to inhibit dislolcation of the upper body from the lower body.

67. The intervertebral implant of claim 66, wherein at least one of the lower body or expansion member includes generally upwardly projecting extensions and at least one of the upper body or expansion member includes recesses configured to accept the extensions, wherein the extensions when positioned in the recesses are configured to inhibit discloation of the upper body from the lower body.

* * * * *